United States Patent [19]

Di Malta et al.

[11] Patent Number: 5,726,322

[45] Date of Patent: Mar. 10, 1998

[54] 1-BENZENESULFONYL-1,3-DIHYDROINDOL-2-ONE DERIVATIVES, THEIR PREPARATION AND PHARMACEUTICAL COMPOSITIONS IN WHICH THEY ARE PRESENT

[75] Inventors: Alain Di Malta, Saint Clément de Rivière; Loïc Foulon, Pinsaguel; Georges Garcia, Saint Gély du Fesc; Dino Nisato, Saint Georges d'Orques; Richard Roux, Vailhaiques; Claudine Serradeil-Legal, Escalquens; Gérard Valette, Lacroix-Sasgarde; Jean Wagnon, Montpellier, all of France

[73] Assignee: Sanofi, Paris, France

[21] Appl. No.: 824,305

[22] Filed: Mar. 26, 1997

Related U.S. Application Data

[62] Division of Ser. No. 473,302, Jun. 7, 1995, which is a division of Ser. No. 323,921, Oct. 17, 1994, which is a continuation-in-part of Ser. No. 129,310, Sep. 30, 1993, abandoned, which is a continuation-in-part of PCT/FR93/00093, Jan. 28, 1993.

[30] Foreign Application Priority Data

| Jan. 30, 1992 | [FR] | France | 92 01034 |
| Jul. 30, 1993 | [FR] | France | 93 09404 |
| Jul. 28, 1994 | [EP] | European Pat. Off. | 94 401 737 |

[51] Int. Cl.$^6$ ................................ C07D 491/10

[52] U.S. Cl. ................................ 548/410

[58] Field of Search ................................ 548/410

[56] References Cited

PUBLICATIONS

Nishio Helvitia Chimica Acta 73 1719, 1990.

*Primary Examiner*—Robert Gerstl
*Attorney, Agent, or Firm*—Bacon & Thomas

[57] ABSTRACT

The invention relates to 1-Benzenesulfonyl-1,3-dihydroindol-2-one derivatives of the formula

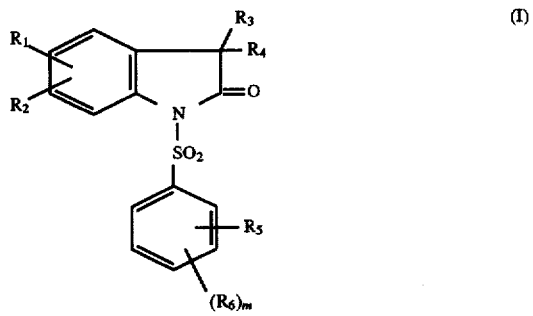

and their salts, where appropriate, to their preparation and to pharmaceutical compositions in which they are present. These compounds have an affinity for the vasopressin and/or ocytocin receptors.

3 Claims, No Drawings

1-BENZENESULFONYL-1,3-DIHYDROINDOL-2-ONE DERIVATIVES, THEIR PREPARATION AND PHARMACEUTICAL COMPOSITIONS IN WHICH THEY ARE PRESENT

This application is a Division of application Ser. No. 08/473,302, filed Jun. 7, 1995, which is a Divisional of application Ser. No. 08/323,921, filed Oct. 17, 1994, which is a Continuation-In-Part of application Ser. No. 08/129,310, filed Sep. 30, 1993, abandoned, which is a Continuation-in-Part of International application Ser. No. PCT/FR93/00093, filed Jan. 28, 1993.

The present invention relates to 1-benzenesulfonyl-1,3-dihydroindol-2-one derivatives, to their preparation and to the pharmaceutical compositions in which they are present.

International patent application WO 91/01306 describes 2-oxoindole derivatives which are useful for the treatment of senile dementia. These compounds have the formula

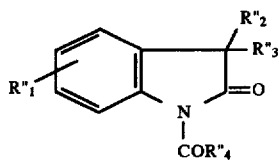

in which

R"$_1$ is a hydrogen, a halogen, an alkyl or an alkoxy;

R"$_2$ is hydrogen or a lower alkyl;

R"$_3$ is an alkyl, a cycloalkylmethyl, a benzodioxanylmethyl or an optionally substituted benzyl; and R"$_4$ is a 1-propylbutyl, a pyridyl or an optionally substituted phenyl.

Several patent applications have recently described families of compounds of non-peptide structure which are active on the vasopressin and/or ocytocin receptors. There may be mentioned European patent applications EP 382 185, EP 444 945, EP 514 667, EP 469 984 and EP 526 348, international patent applications WO 91/05 549 and WO 93/15 051, patent application JP 04/321 669 and, more particularly, patent application JP 03/127 732. This last patent application describes indole-3-propionic acid derivatives of the formula

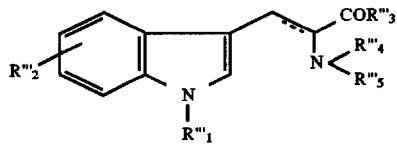

in which

R'''$_1$ is hydrogen, an alkyl, an alkenyl, a phenylalkyl, a tetrahydrofuryl, an alkoxycarbonyl, an alkoxycarbonylalkyl, a carboxyalkyl or an alkanoyl;

R'''$_2$ is hydrogen, a hydroxyl, an alkoxy, an alkyl, a phenylalkyl, a phenylalkoxy or a halogen;

R'''$_3$ is a hydrogen, an alkoxy, a free or substituted amino group or an amino acid residue;

R'''$_4$ is hydrogen, an alkyl or a phenylalkyl; and

R'''$_5$ is a benzoyl, a phenyl, an alkyl, a phenylalkenylcarbonyl, a thienylcarbonyl, a phenylsulfonyl, a pyridylcarbonyl or an imidazolylcarbonyl, it being possible for the phenyl and alkyl groups of the substituent R'''$_5$ to be substituted.

These compounds are vasopressin antagonists.

Patent U.S. Pat. No. 4,803,217 claims hapalindolinones obtained by fermentation which are vasopressin antagonists. These compounds have the following formula:

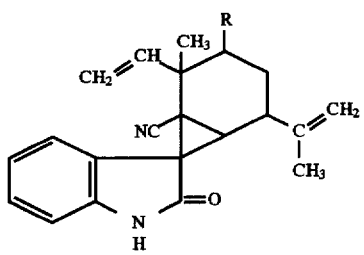

in which R is H or Cl.

Novel 1-benzenesulfonyl-1,3-dihydroindol-2-one derivatives have now been found which also have an affinity for the vasopressin and ocytocin receptors.

Vasopressin is a hormone known for its antidiuretic effect and its effect in the regulation of arterial pressure. It stimulates several types of receptors, namely $V_1$ ($V_{1a}$, $V_{1b}$) and $V_2$. These receptors are localized in the liver, vessels (coronary, renal, cerebral), platelets, kidney, uterus, adrenal glands, central nervous system and pituitary gland. Ocytocin has a peptide structure similar to that of vasopressin. The ocytocin receptors are also found on the smooth muscle of the uterus, as well as on myoepithelial cells of the mammary gland, in the central nervous system and in the kidney. The localization of the different receptors is described in: S. JARS et al., Vasopressin and ocytocin receptors: an overview, in Progress in Endocrinology; H. IMURA and K. SHIZURNE ed., Experta Medica, Amsterdam, 1988, 1183–1188, and in the following articles: Presse Médicale, 1987, 16 (10), 481–485; J. Lab. Clin. Med., 1989, 114 (6), 617–632; and Pharmacol. Rev., 1991, 43 (1), 73–108. Vasopressin thus exerts cardiovascular, hepatic, antidiuretic and aggregating effects and effects on the central and peripheral nervous system and in the uterine domain. Ocytocin is involved in parturition, lactation and sexual behavior.

The compounds according to the present invention make it possible selectively either to mimic the effects of the hormone (in the case of agonists) or to inhibit them (in the case of antagonists). Vasopressin receptor antagonists can affect the regulation of the central and peripheral circulation, especially the coronary, renal and gastric circulation, as well as the regulation of hydration and the release of adrenocorticotrophic hormone (ACTH). Vasopressin agonists can advantageously replace vasopressin or its analogs in the treatment of diabetes insipidus; they can also be used in the treatment of enuresis and in the regulation of hemostasis: treatment of hemophilia and von Willebrand's syndrome, antidote to platelet aggregating agents. F. A. LASZLO, Pharmacol. Rev., 1991, 43, 73–108; and Drug Investigation, 1990, Z (Suppl. 5), 1–47. The hormones themselves, namely vasopressin and ocytocin, and some of their peptide or non-peptide analogs are used in therapeutics and have been found to be effective. Several reviews and numerous literature articles may be mentioned: Vasopressin, P. GROSS et al. ed., John Libbey Eurotext, 1993, in particular 243–257 and 549–562; F. A. LASZLO and F. A. LASZLO Jr., Clinical perspectives for vasopressin antagonists, Drug News Perspect., 1993, 6 (8); W. G. NORTH, J. Clin. Endocrinol., 1991, 73, 1316–1320; J. J. LEGROS et al., Prog. Neuro-Pharmacol. Biol. Psychiat., 1988, 12, 571–586; K. E. ANDERSSON et al., Drugs Today, 1988, 24 (7), 509–528; D. L. STUMP et al., Drugs, 1990, 39, 38–53; S. CALTABIANO et al., Drugs Future, 1988, 13, 25–30; Y. MURA et al., Clin. Nephrol., 1993, 40, 60–61; and FASEB J., 1994, 8 (5), A 587: 3398.

Thus the compounds according to the invention are useful especially in the treatment of complaints of the central and peripheral nervous system, the cardiovascular system, the renal domain and the gastric domain and in disorders of sexual behavior, in man and animals.

The present invention relates to compounds of the formula

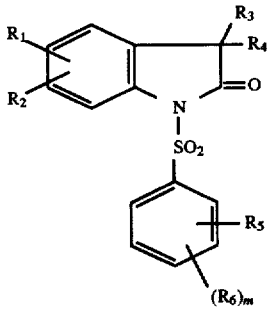

in which $R_1$ and $R_2$ are each independently a hydrogen; a hydroxyl; an ω-halogeno-$C_1$-$C_7$-alkoxy; a halogen; a $C_1$-$C_7$-alkyl; a trtfluoromethyl; a $C_1$-$C_7$-alkoxy; a Polyhalogeno-$C_1$-$C_7$-alkoxy; an ω-hydroxy-$C_2$-$C_7$-alkoxy; an ω-methoxyalkoxy in which the alkyl is $C_2$-$C_7$; an ω-amino-$C_2$-$C_7$-alkoxy which is free or substituted by one or two $C_1$-$C_7$-alkyls; a $C_3$-$C_7$-cycloalkoxy; a cycloalkylmethoxy in which the cycloalkyl is $C_3$-$C_7$; a phenoxy; a benzyloxy; a $C_1$-$C_7$-alkylthio; a phenylthio; a nitro; an amino which is free or substituted by one or two $C_1$-$C_7$-alkyls; a cyano; a $C_1$-$C_7$-acyl; a $C_1$-$C_7$-acyloxy; a $C_1$-$C_7$-alkylsulfonamido; a phenylsulfonamido; a benzylsulfonamido; a $C_1$-$C_7$-alkylamido; a $C_1$-$C_7$-alkoxycarbonylamino; a ureido which is unsubstituted or substituted by a phenyl, a benzyl or one or two $C_1$-$C_7$-alkyls; or a thioureido which is unsubstituted or substituted by a phenyl, a benzyl or one or two $C_1$-$C_7$-alkyls;

$R_3$ and $R_4$ are each independently a $C_1$-$C_7$-alkyl; a $C_3$-$C_7$-cycloalkyl; a phenyl; a benzyl; a cycloalkylmethyl in which the cycloalkyl is $C_3$-$C_7$; or an ω-hydroxy-$C_2$-$C_7$-alkyl in which the hydroxyl is free or substituted by a group selected from $C_1$-$C_4$-alkyl groups, $C_1$-$C_5$-alkoxyalkyl groups in which the alkyl is $C_1$-$C_4$, phenylalkoxyalkyl groups in which the alkoxy is $C_1$-$C_2$ and the alkyl is $C_1$-$C_4$; and tetrahydrofuranyl and tetrahydropyranyl groups; or $R_3$ and $R_4$ together form a group —$(CH_2)_pX(CH_2)_q$—; or $R_3$ and $R_4$, together with the carbon to which they are bonded, form an optionally fused, saturated or unsaturated $C_3$-$C_{12}$ hydrocarbon ring which is unsubstituted or substituted by one or more $C_1$-$C_7$-alkyl groups, by an oxo group, by a $C_3$-$C_5$-spirocycloalkyl or by one or two hydroxyls which are free or substituted by a group selected from $C_1$-$C_4$-alkyl groups, $C_1$-$C_5$-alkoxyalkyl groups in which the alkyl is $C_1$-$C_4$, ω-hydroxyalkyl groups in which the alkyl is $C_1$-$C_4$, triphenylmethoxyalkyl groups in which the alkyl is $C_1$-$C_4$, phenylalkoxyalkyl groups in which the alkoxy is $C_1$-$C_2$ and the alkyl is $C_1$-$C_4$, and tetrahydrofuranyl, tetrahydropyranyl, and $C_1$-$C_7$-acyl groups; or else $R_1$ and $R_4$ each have one of the meanings indicated above and $R_2$ is located in the 4-position of the indole and forms a group $(CH_2)_3$ with $R_3$;

$R_5$ and $R_6$ are each independently a hydrogen; a halogen; a $C_1$-$C_7$-alkyl; a trifluoromethyl; a cyano; a nitro; an amino which is free or substituted by one or two $C_1$-$C_7$-alkyls; a hydroxyamino; a hydroxyl; a carboxyl; a guanidino which is unsubstituted or monosubstituted or disubstituted by a $C_1$-$C_7$-alkyl, a phenyl or a benzyl; a group —$OR_7$; a group —$SR_7$; a $C_1$-$C_7$-acyl; a $C_1$-$C_7$-alkoxycarbonyl; a phenoxycarbonyl; a benzyloxycarbonyl; a carbamoyl substituted by groups $R'_6$ and $R''_6$; a thiocarbamoyl which is free or substituted by one or two $C_1$-$C_7$-alkyls; a sulfamoyl; an alkylsulfamoyl or dialkylsulfamoyl in which the alkyl is $C_1$-$C_7$; a group —$SO_2R'_7$; an alkylsulfonamido in which the alkyl is $C_1$-$C_7$; a phenylsulfonamido; a benzylsulfonamido; a group —$COR'_7$; a group —$NR_8R_9$; or a group —CO—NH—$CR_{10}R'_{10}$—$COR_{12}$; if appropriate, the phenyl group forming part of the substituent $R_5$ and/or $R_6$ can be unsubstituted or monosubstituted or polysubstituted by a $C_1$-$C_7$-alkyl, a trifluoromethyl, a $C_1$-$C_7$-alkoxy, a halogen, a sulfamoyl, an alkylsulfamoyl in which the alkyl is $C_1$-$C_7$, a carboxyl, an alkoxycarbonyl in which the alkyl is $C_1$-$C_7$, a $C_1$-$C_7$-acyloxy or an imidazolyl;

$R'_6$ and $R''_6$ are each independently hydrogen; a $C_1$-$C_7$-alkyl which is unsubstituted or substituted by one or more halogens or $R'''_6$; a $C_3$-$C_7$-cycloalkyl which is unsubstituted or substituted by a $C_1$-$C_4$-alkyl; a phenyl; a pyridyl; a methylpyridyl; a piperidin-4-yl; a methylpiperidin-4-yl; or a pyrrolidin-1-yl; or $R'_6$ and $R''_6$, with the nitrogen atom to which they are bonded, form a pyrrolidino group substituted by a hydroxymethyl or by a carbamoyl which is free or substituted by one or two $C_1$-$C_7$-alkyls;

$R'''_6$ is a hydroxyl; a $C_1$-$C_7$-alkoxy; an amino which is free or substituted by one or two $C_1$-$C_7$-alkyls; a carbamoyl which is free or substituted by one or two $C_1$-$C_7$-alkyls or in which the two substituents, together with the nitrogen atom to which they are bonded, form a pyrrolidino, a piperidino or a perhydroazepino; a cyano; a carboxyl which is free or esterified by a $C_1$-$C_7$-alkyl or by a benzyl; a phenyl; a $C_3$-$C_7$-cycloalkyl; an adamantyl; or a heterocyclic radical selected from pyridyl, methylpyridyl, furanyl, tetrahydrofuranyl, thienyl, methylthienyl, pyrrolidino, piperidino and perhydroazepino groups;

$R_7$ is a $C_1$-$C_7$-alkyl; a phenyl; a benzyl; a $C_3$-$C_7$-cycloalkyl; a $C_2$-$C_7$-alkenyl; an ω-halogeno-$C_2$-$C_7$-alkyl; a polyhalogeno-$C_1$-$C_7$-alkyl; an ω-hydroxy-$C_2$-$C_7$-alkyl; a $C_1$-$C_7$-acyl; an ω-carboxy-$C_1$-$C_7$-alkyl which is free or esterified by a $C_1$-$C_7$-alkyl or a benzyl; an ω-amino-$C_2$-$C_7$-alkyl in which the amino group is free, substituted by one or two $C_1$-$C_7$-alkyls or in the form of an ammonium ion; or an ω-carbamoyl-$C_1$-$C_7$-alkyl which is free or substituted by one or two $C_1$-$C_7$-alkyls;

$R'_7$ is a piperazin-1-yl group which is unsubstituted or substituted in the 4-position by a group $R'''_7$; a piperidino group which is unsubstituted or substituted in the 4-position by a group $R'''_7$; an azetidin-1-yl group which is unsubstituted or substituted in the 3-position by a group $R'''_7$; a pyridyl group which is unsubstituted or substituted by a methyl; or a pyrrolidino group which is unsubstituted or substituted by a group $R''''_7$;

$R''_7$ is a $C_1$-$C_7$-alkyl; a phenyl; a benzyl or a $C_1$-$C_7$-acyl; $R'''_7$ is $R''_7$; or an amino which is free or carries a protecting group;

$R''''_7$ is $R'''_7$; or a carboxyl group which is free or esterified by a $C_1$-$C_7$-alkyl;

$R_8$ and $R_9$ are each independently a hydrogen; a $C_1$-$C_7$-alkyl; a benzyl; or a phenyl; $R_9$ can also be a $C_3$-$C_8$-alkene, in which the double bond may be in the $C_3$-$C_4$-position; a $C_1$-$C_7$-acyl; a $C_1$-$C_7$-thioacyl; a cycloalkylcarbonyl in which the cycloalkyl is $C_3$-$C_7$; a cycloalkylthiocarbonyl in which the cycloalkyl is $C_3$-$C_7$; an ω-amino-$C_1$-$C_7$-acyl; an ω-hydroxy-$C_1$-$C_7$-acyl; an ω-benzyloxy-$C_1$-$C_7$-acyl; a phenoxycarbonyl; a phenoxythiocarbonyl; a thienocarbonyl; a pyridylcarbonyl; a methylpyridylcarbonyl; a $C_1$–$C_7$-alkoxycarbonyl; a benzoyl; a phenacetyl; a group —CO—$CR_{10}R'_{10}$—$NR_{11}R'_{11}$; a group —$CR_{10}R'_{10}COR_{12}$; a group —$(CH_2)_tCOR_{12}$; a group —$CO(CH_2)_tCOR_{12}$; a carbamoyl which is unsubstituted or substituted by $R_{14}$ and $R'_{14}$; a thiocarbamoyl which is unsubstituted or substituted by $R_{14}$ and $R'_{14}$; or a heterocyclic radical selected from pyrazolyl, imidazolyl, triazolyl, tetrazolyl, pyridinyl, pyridazinyl, pyrimidinyl, pyridyl and thiazolyl groups; or $R_8$ and $R_9$, together with the nitrogen atom to which they are bonded, form hydantoin; N-methylhydantoin; or a heterocycle selected from pyrrol-1-yl, dihydropyrrol-1-yl, Δ3-pyrrolin-1-yl, pyrrolidin-1-yl and isoindolin-2-yl in which the benzene ring can be unsubstituted or substituted by a halogen, a $C_1$–$C_7$-alkyl, a trifluoromethyl or a methoxy;

$R_{10}$ and $R'_{10}$ are each independently hydrogen; a $C_1$–$C_7$-alkyl; or a benzyl; or $R_{10}$ and $R'_{10}$, together with the carbon atom to which they are bonded, form a $C_3$–$C_7$-cycloalkyl;

$R_{11}$ and $R'_{11}$ are each independently hydrogen; or a $C_1$–$C_7$-alkyl;

$R_{12}$ is a hydroxyl; a $C_1$–$C_7$-alkoxy; or an amino which is unsubstituted or substituted by one or two $C_1$–$C_7$-alkyls;

$R_{13}$ is hydrogen; a $C_1$–$C_7$-alkyl; a phenyl; a benzyl; a $C_1$–$C_7$-acyl; a $C_1$–$C_7$-alkoxycarbonyl; or a carbamoyl which is unsubstituted or substituted by one or 2 $C_1$–$C_7$-alkyls;

$R_{14}$ and $R'_{14}$ are each independently a $C_1$–$C_7$-alkyl which is unsubstituted or substituted by $R_{15}$; a phenyl which is unsubstituted or substituted by $R'_{15}$; a $C_3$–$C_7$-cycloalkyl; or an adamantyl; or $R_{14}$ and $R'_{14}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, by a phenyl or by an amino group which is free or carries a protecting group;

$R_{15}$ is a phenyl; a pyridyl; a hydroxyl; a $C_1$–$C_7$-alkoxy; an amino which is free or substituted by one or two $C_1$–$C_7$-alkyls; or a carboxyl which is free or esterified by a $C_1$–$C_7$-alkyl;

$R'_{15}$ is a hydroxyl; or an amino which is free or substituted by one or two $C_1$–$C_7$-alkyls;

m is 1 or, if $R_6$ is a halogen, a $C_1$–$C_7$-alkyl or a $C_1$–$C_7$-alkoxy, m can also be 2, 3 or 4, or else $(R_6)_m$ can be m substituents having different meanings selected from halogen, $C_1$–$C_7$-alkyl and $C_1$–$C_7$-alkoxy;

p and q are each an integer, it being possible for their sum to vary from 3 to 6;

t is an integer which can vary from 2 to 5;

t' is an integer which can vary from 0 to 5, preferably 0 to 3;

X is oxygen; a group $S(O)_n$; a group $NR_{13}$; or a group $N(O)R_{13}$; and n is 0, 1 or 2;

and their salts where appropriate.

If a compound according to the invention has one or more asymmetric carbons, the invention includes all the optical isomers of this compound.

If a compound according to the invention exhibits conformational isomerism of the axial-equatorial type, the invention includes all the conformational isomers of this compound.

The salts of the compounds of formula (I) according to the present invention include those with mineral or organic acids which permit a suitable separation or crystallization of the compounds of formula (I), such as picric acid, oxalic acid or an optically active acid, for example a mandelic acid or a camphosulfonic acid, and mineral or organic acids which form physiologically acceptable salts such as the hydrochloride, hydrobromide, sulfate, hydrogensulfate, dihydrogenphosphate, maleate, fumarate or naphthalene-2-sulfonate.

The salts of the compounds of formula (I) also include the salts with organic or mineral bases, for example the salts of alkali metals or alkaline earth metals, such as the sodium, potassium and calcium salts, the sodium and potassium salts being preferred, or with an amine such as trometamol, or else the salts of arginine, lysine or any physiologically acceptable amine.

According to the present invention, halogen is understood as meaning an atom selected from fluorine, chlorine, bromine and iodine, preferably fluorine or chlorine. Amine-protecting group is understood as meaning a group such as, for example, a $C_1$–$C_4$-alkyl, such as methyl or tert-butyl.; benzhydryl; trityl; benzoyl; a $C_1$–$C_4$-alkylcarbonyl, such as tert-butoxycarbonyl, benzyloxycarbonyl; benzyl or substituted benzyl such as p-nitrobenzyl, p-chlorobenzyl or p-methoxybenzyl.

According to the present invention, $C_1$–$C_4$-, $C_1$–$C_6$- or $C_1$–$C_7$-alkyl is understood as meaning a linear or branched alkyl.

According to the present invention, optionally fused, saturated or unsaturated $C_3$–$C_{12}$ hydrocarbon ring is understood as meaning various hydrocarbon rings of monocyclic, bicyclic or tricyclic structure, for example a cyclobutane, a cyclopentane, a cyclohexane, a cycloheptane, a cyclooctane, an indane, a hexahydro indane, an adamantane, a norbornane, a norbornene, a dihydrophenalene, a tricyclo[5.2.1.0$^{2,6}$]decane, a tricyclo[5.2.1.0$^{2,6}$]dec-8-ene, a bicyclo[2.2.1]heptane or a bicyclo[3.3.1]nonane.

According to the present invention, $C_1$–$C_7$-acyl is understood as comprising $C_1$–$C_6$-alkylcarbonyl and formyl;

$C_1$–$C_7$-acyloxy is understood as comprising $C_1$–$C_6$-alkylcarbonyloxy and formyloxy;

$C_1$–$C_7$-thioacyl is understood as meaning $C_1$–$C_6$-alkylthiocarbonyl;

ω-amino- or ω-hydroxy-$C_1$–$C_7$-acyl is understood as meaning ω-amino- or ω-hydroxy-$C_1$–$C_6$-alkylcarbonyl;

ω-benzyloxy-$C_1$–$C_7$-acyl is understood as meaning ω-benzyloxy-$C_1$–$C_6$-alkylcarbonyl.

According to the present invention, if $R_3$ and $R_4$, together with the carbon to which they are bonded, form an optionally fused, saturated or unsaturated $C_3$–$C_{12}$ hydrocarbon ring substituted by a hydroxyl, the preferred groups for substituting said hydroxyl are the methyl, ethyl, methoxymethyl, methoxyethyl, phenylmethoxymethyl, tetrahydro furanyl and tetrahydropyranyl groups.

The compounds of formula (I) in which $R_1$ is in the 5-position of the indol-2-one and $R_2$ is hydrogen are preferred compounds.

The compounds of formula (I) in which $R_1$ is a chlorine or fluorine atom or an ethoxy group in the 5-position of the indol-2-one and $R_2$ is hydrogen are preferred compounds.

The compounds of formula (I) in which $R_3$ and $R_4$, together with the carbon to which they are bonded, form a $C_3$–$C_{12}$ hydrocarbon ring are preferred compounds; particularly preferred compounds are those in which $R_3$ and $R_4$, together with the carbon to which they are bonded, form a cycloheptane, an adamantane, a tricyclo[5.2.1.0$^{2,6}$]dec-8-ene, a tricyclo[5.2.1.0$^{2,6}$]decane, a bicyclo[2.2.1]heptane, a bicyclo[3.3.1]nonane or a cyclohexane which is unsubstituted or substituted by a $C_3$–$C_5$-spirocycloalkyl or by one or two $C_1$–$C_7$-alkyl groups.

More particularly preferred compounds are those in which $R_3$ and $R_4$, together with the carbon to which they are bonded, form a cyclohexane substituted by a group selected from methoxy, ethoxy and 2-methoxyethoxy.

The compounds of formula (I) in which $R_3$ and $R_4$, together with the carbon to which they are bonded, form a piperidine-4 or N-methylpiperidine-4 ring are also preferred.

The compounds of formula (I) in which the substituents $R_5$ and $R_6$ are in the 2,4-position of the phenyl ring are preferred compounds.

The compounds of formula (I) in which $R_5$ and $R_6$ are each a methoxy are preferred compounds. Likewise, the compounds in which $R_5$ in the 2-position is a methoxy and $R_6$ in the 4-position is a $C_1$–$C_7$-acylamino, a $C_1$–$C_4$-dialkylureido or an alkoxycarbonylalkyl carbamoyl in which the alkyl groups are $C_1$–$C_7$ are preferred compounds.

The compounds of formula (I) in which $R_5$ is an orthomethoxy group and $R_6$ in the para-position is a group selected from:
(piperidin-1-yl)carboxamido,
(2-cyanoprop-2-yl)carbonyl,
pyrrolidin-1-yl,
3,3-diethylguanidino and
N',N'-diethylthioureido
are preferred compounds.

The following abbreviations are used in the description and in the Examples:
DCM: dichloromethane
ether: ethyl ether
iso ether: isopropyl ether
Boc: tert-butoxycarbonyl
Me, MeO: methyl, methoxy
Et, EtO: ethyl, ethoxy
Pr, iPr, nPr: propyl, isopropyl, n-propyl
Bu, iBu, tBu: butyl, isobutyl, tert-butyl
Ph: phenyl
Bz: benzyl
Ts: tosyl
Ac: acetyl
AcOEt: ethyl acetate
AcOH: acetic acid
HCl: hydrochloric acid
MeOH: methanol
EtOH: ethanol
DMF: dimethylformamide
THF: tetrahydrofuran
DMSO: dimethyl sulfoxide
DIPEA: diisopropylethylamine
NaOH: sodium hydroxide
$NaHCO_3$: sodium hydrogencarbonate
TEA: triethylamine
TFA: trifluoroacetic acid
TMEDA: tetramethylethylenediamine
Lawesson's reagent: 2,4-bis(4-methoxyphenyl)-1,3-dithia-2,4-diphosphetane 2,4-disulfide
M.p.: melting point
saline solution: saturated aqueous sodium chloride solution
TLC: thin layer chromatography
HPLC: high pressure liquid chromatography aqueous hydrochloric acid: dilute hydrochloric acid, about 1N
RT: room temperature
B.p.: boiling point
NMR: nuclear magnetic resonance
s: singlet bs: broad singlet
d: doublet
t: triplet
q: quadruplet
m: unresolved signals
mt: multipier The present invention further relates to a process for the preparation of the compounds according to the invention, and their salts, which comprises:

1/ reacting a benzenesulfonyl halide of the formula

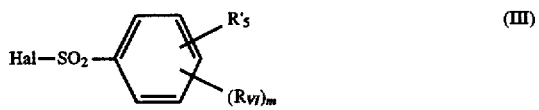

in which Hal is a halogen atom, preferably chlorine, and $R'_5$ and $R_{VI}$ are respectively either $R_5$ and $R_6$ as defined above for (I), or precursor groups of $R_5$ and $R_6$, with a 1,3-dihydroindol-2-one disubstituted in the 3-position of the formula

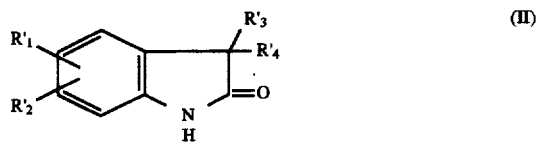

in which $R'_1$, $R'_2$, $R'_3$ and $R'_4$ are respectively either $R_1$, $R_2$, $R_3$ and $R_4$ as defined for (I), or precursor groups of $R_1$, $R_2$, $R_3$ and $R_4$; and 2/ either, if $R'_1=R_1$, $R'_2=R_2$, $R'_3=R_3$, $R'_4=R_4$, $R'_5=R_5$ and $R_{VI}=R_6$, isolating the resulting compound of formula (I);

3/ or, if any one of the groups $R'_1$, $R'_2$, $R'_3$, $R'_4$, $R'_5$ and/or $R_{VI}$ is respectively a precursor group of $R_1$, $R_2$, $R_3$, $R_4$, $R_5$ and/or $R_6$, subjecting the compound obtained, hereafter called the compound of formula (I'), to a subsequent treatment in order to prepare the compound of formula (I) by converting any one of the groups $R'_1$, $R'_2$, $R'_3$, $R'_4$, $R'_5$ and/or $R_{VI}$ to $R_1$, $R_2$, $R_3$, $R_4$, $R_5$ and/or $R_6$ respectively; and 4/ if desired, converting the resulting compound of formula (I) to one of its salts.

The reaction of step 1/ is carried out in an anhydrous solvent such as DMF or THF, in the presence of a metal hydride such as, for example, sodium hydride, or in the presence of an alcoholate such as potassium tert-butylate.

The 1,3-dihydroindol-2-ones (II) are known or can be prepared by known methods using different procedures.

Compounds (II) in which $R'_1$ and/or $R'_2$ are a halogen and $R'_3$ and $R'_4$, together with the carbon to which they are bonded, form a spirocyclobutane, a spirocyclohexane or a spirocycloheptane are known, for example from D. W. Robertson et al., J. Med. Chem., 1987, 30 (5), 824–829. Also, 5-chloro-3-spirocyclopentaneindol-2-one is described in patent U.S. Pat. No. 3,947,451.

To prepare the compounds (II) in the case where $R'_3$ and $R'_4$ together are a hydrocarbon group, it is possible to use the Brunner reaction described by R. F. Moore and S. G. P. Plant in J. Chem. Soc., 1951, 3475–3478, which leads to the preparation of compounds (II) in which $CR'_3R'_4$ is a cyclopentane or a cyclohexane.

This reaction is carried out by cyclizing a phenylhydrazide derivative of the formula

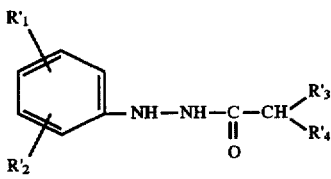

(IV)

in which R'$_1$, R'$_2$, R'$_3$ and R'$_4$ are as defined above for (II), for example by heating in quinoline in the presence of calcium oxide.

According to the same authors, the phenylhydrazide derivative (IV) is obtained by reacting a hydrazine derivative of the formula

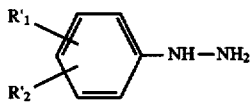

(V)

in which R'$_1$ and R'$_2$ are as defined above for (II), with an acid halide of the formula

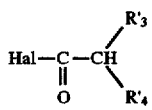

(VI)

in which R'$_3$ and R'$_4$ are as defined above for (II).

In one particular embodiment, if R'$_3$ and R'$_4$, together with the carbon to which they are bonded, form a polycondensed hydrocarbon ring, for example a norbornane or a norbornene, the reaction is carried out by the method described by J. Wolff et al., Tetrahadron, 1986, 42 (15), 4267–4272: First of all, a lithium salt of the compound (IV) is prepared by reaction with a lithium reagent such as n-butyllithium, in an inert solvent such as THF, at low temperature, and then the cyclization is effected by heating in a solvent such as naphthalene or prehnitene (1,2,3,4-tetramethylbenzene).

The compounds (II) in which R'$_1$=R'$_2$=H and CR'$_3$R'$_4$ is adamantane are described in I. Fleming et al., J. Chem. Soc., Perkin Trans. I, 1991, 3, 617–626. The compounds (II) in which R'$_3$ and R'$_4$, together with the carbon atom to which they are bonded, form an adamantane and R'$_1$ and R'$_2$ are other than hydrogen are novel and form part of the invention. They can be prepared by the method described above.

The hydrazine derivatives (V) are known or are prepared by known methods. The same applies to the acid halides (VI).

A 1,3-dihydroindol-2-one disubstituted in the 3-position (II) can also be prepared from a 1,3-dihydroindol-2-one of the formula

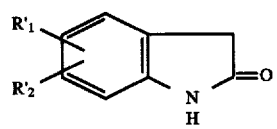

(VII)

in which R'$_1$ and R'$_2$ are as defined above for (II), by using various processes.

For example, the method described by A. S. Kende and J. C. Hodges in Synth. Commun., 1982, 12 (1), 1–10, involves the addition of an alkylating agent in an appropriate solvent. Thus, to prepare a compound (II) in which R'$_3$=R'$_4$, the reaction is carried out in THF at −75° C., in the presence of TMEDA, by the addition of an alkyllithium such as butyllithium, followed by reaction with a halide of the formula R'$_3$Hal; if R'$_3$ and R'$_4$ are different, the alkylation reaction can be performed in 2 steps with 2 different alkyl halides of the formulae R'$_3$Hal and R'$_4$Hal. To prepare a compound (II) in which R'$_3$ and R'$_4$ together form a group of the formula —(CH$_2$)$_n$—, where n varies from 3 to 12, the reagent used is a compound of the formula Z(CH$_2$)$_n$Z, in which Z is an electrophilic group such as a halogen, preferably bromine or iodine, a tosyloxy group or a mesyloxy group. In one variant of this process, the reaction can also be carried out by the addition of an alkali metal alcoholate, such as potassium tert-butylate, onto a compound of formula (VII), in THF at −40° C., followed by the addition of a compound of the formula Z—(CH$_2$)$_n$Z as defined above.

The compounds (II) in which R'$_3$ and R'$_4$, together with the carbon to which they are bonded, form a C$_4$–C$_8$ hydrocarbon ring substituted by one or more C$_1$–C$_7$-alkyl groups or by a C$_3$–C$_5$-spirocycloalkyl are prepared in the same way. These compounds are novel and form part of the invention.

The compounds of formula (II) in which R'$_3$ and R'$_4$ are each independently an alkyl or a phenyl are known. For example, patent DE 3 300 522 describes 5-alkoxy-3,3-dimethylindol-2-ones.

If R'$_3$ and R'$_4$ together form a group —(CH$_2$)$_p$X —(CH$_2$)$_q$—, in which p, q and X are as defined above for (I), a 1,3-dihydroindol-2-one disubstituted in the 3-position of formula (II) can be prepared from a 1,3-dihydroindol-2-one unsubstituted in the 3-position (VII) by reaction with a compound of the formula Z—(CH$_2$)$_p$—X—(CH$_2$)$_q$—Z   (VIII)

in which Z is as defined above and X, p and q are as defined above for (I). The reaction is carried out in the presence of an alcoholate, for example potassium tert-butylate, in an anhydrous solvent such as, for example, THF.

If X is a nitrogen atom substituted by a C$_1$–C$_7$-acyl, a C$_1$–C$_7$-alkoxycarbonyl or a C$_1$–C$_7$-alkylcarbamoyl, the substitution on X can be effected either on the 1,3-dihydroindol-2-one derivative (II) or on the final compound (I) starting from a compound in which the nitrogen atom (X═NH) is unsubstituted.

The compounds (I) in which X═NH are preferred compounds according to the invention.

Thus, if X is a nitrogen atom substituted by a C$_1$–C$_7$-alkoxycarbonyl, the first step is to prepare a compound (II) or (I) in which X is NH, which is then reacted with the appropriate chloroformate to give the desired compound (II) or (I). In the same way, a C$_1$–C$_7$-alkyl isocyanate is reacted with a compound (II) or (I) in which X═NH to give a derivative (II) or a compound (I) in which X is a nitrogen atom substituted by an alkylcarbamoyl. An acid chloride or an anhydride is reacted with a compound (II) or a compound (I) in which X═NH in order to prepare a compound of formula (II) or (I) in which X is a nitrogen atom substituted by a C$_1$–C$_7$-acyl which is a C$_1$–C$_6$-alkylcarbonyl.

Formic acid in the presence of acetic anhydride is reacted with a compound (II) or (I) in which X═NH in order to prepare a compound of formula (II) or (I) in which X is a nitrogen atom substituted by a formyl.

If X is a sulfur atom or a nitrogen atom substituted by R$_{13}$, it is also possible firstly to prepare a compound of the formula

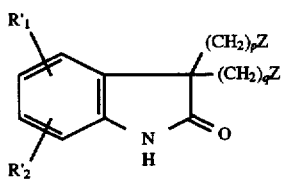
(II)' in which R'$_1$, R'$_2$, Z, p and q are as defined above, and to perform a nucleophilic substitution with a hydrogen sulfide salt or an amine of the formula H$_2$NR$_{13}$, in a solvent such as an alcohol, an ether, DMF or a mixture thereof, at a temperature between 5° C. and the reflux temperature.

The 1,3-dihydroindol-2-ones of formula (II)' are obtained from the corresponding diols, either as such or protected, for example by a tetrahydropyren-2-yl group. The reaction can be carried out with dibromotriphenylphosphorane according to J. Chem. Soc., Chem. Commun., 1989, 1619.

The compounds (II) in which R'$_3$ and R'$_4$, together with the carbon to which they are bonded, form a pyrrolidine, N-alkylpyrrolidine, piperidine or N-alkylpiperidine ring are described by M. J. Kornet in J. Med. Chem., 1976, 19 (7), 892–899.

In particular, horsfiline of the formula

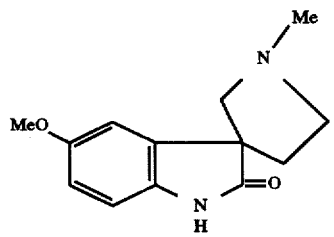

is an alkaloid described in A. Jossang et al., J. Org. Chem., 1991, 56 (23), 6527–6530.

The compounds (II) in which R'$_3$ and R'$_4$, together with the carbon to which they are bonded, form a group —(CH$_2$)$_p$X(CH$_2$)$_q$— in which p and q are integers whose sum can vary from 3 to 6 and X is oxygen, sulfur or a group NR$_{13}$, R$_{13}$ being a C$_1$–C$_4$-acyl, a benzyl, a C$_1$–C$_4$-alkoxy-carbonyl or a carbamoyl which is unsubstituted or substituted by one or 2 C$_1$–C$_4$-alkyls,
are novel and form part of the invention.

To prepare a compound of formula (II) in which R'$_3$ and R'$_4$, together with the carbon to which they are bonded, form a tricyclo[5.2.1.0$^{2,6}$]decane or a tricyclo[5.2.1.0$^{2,6}$]dec-8-ene, a compound (VII)' or, respectively, a compound (VII)" of the formulae

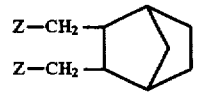
(VII)'

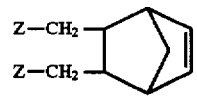
(VII)"

in which Z is as defined above, is reacted with a compound of formula (VII). Compounds (VII)' and (VII)" substituted by one or more C$_1$–C$_7$-alkyl groups are used to prepare compounds (II) in which said carbocycles are substituted.

A compound of formula (II) in which R'$_3$ and R'$_4$, together with the carbon to which they are bonded, form a tricyclo [5.2.1.0$^{2,6}$]decane can also be prepared by the catalytic hydrogenation of a compound of formula (II) in which R'$_3$ and R'$_4$, together with the carbon to which they are bonded, form a tricyclo[5.2.1.0$^{2,6}$]dec-8-ene, for example in the presence of palladium-on-charcoal or Raney® nickel.

The compounds (II) in which R'$_3$ and R'$_4$, together with the carbon to which they are bonded, form a tricyclo [5.2.1.0$^{2,6}$]decane, a tricyclo[5.2.1.0$^{2,6}$]dec-8-ene, an indane or a hexahydroindane which are unsubstituted or substituted by one or more C$_1$–C$_4$-alkyls are novel and form part of the invention.

A compound of formula (I) in which R$_3$ and R$_4$, together with the carbon to which they are bonded, form a tricyclo [5.2.1.0$^{2,6}$]decane can also be prepared by the catalytic hydrogenation of a compound of formula (I) in which R$_3$ and R$_4$, together with the carbon to which they are bonded, form a tricyclo[5.2.1.0$^{2,6}$]dec-8-ene, for example in the presence of palladium-on-charcoal or Raney® nickel.

To prepare a compound (II) in which R'$_3$ and R'$_4$, together with the carbon to which they are bonded, form an indane or a hexahydroindane, a compound (VIII)' or, respectively, a compound (VIII)" of the formulae

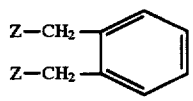
(VIII)'

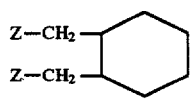
(VIII)"

in which Z is defined as indicated above for (VIII), is reacted with a compound (VII). Compounds (VIII)' and (VIII)" substituted by one or more C$_1$–C$_7$-alkyl groups are used to prepare compounds (II) in which the indane or hexahydroindane is substituted.

The method of A. S. Kende and J. C. Hodges described above or its variant described above can be used to prepare compounds of formula (II) in which the substituents R'$_3$ and R'$_4$, together with the carbon to which they are bonded, form an optionally fused, saturated or unsaturated C$_3$–C$_{12}$ hydrocarbon ring substituted by one or more C$_1$–C$_7$-alkyl groups or by a group selected from an oxo group protected under acetal form, a C$_3$–C$_5$-spirocycloalkyl, or one or two hydroxyls substituted by a C$_1$–C$_4$-alkyl, a (C$_1$–C$_5$) alkoxyalkyl in which the alkyl is C$_1$–C$_4$, a triphenyl-methoxyalkyl in which the alkyl is C$_1$–C$_4$, a phenylalkoxyalkyl in which the alkoxy is C$_1$–C$_2$ and the alkyl is C$_1$–C$_4$, a tetrahydrofuranyl or a tetrahydropyranyl. To obtain the compounds of formula (I) in which R$_3$ and R$_4$, together with the carbon to which they are bonded, form an optionally fused, saturated or unsaturated C$_3$–C$_{12}$ hydrocarbon ring substituted by one or two hydroxyls, the corresponding compounds of formula (I) in which the hydroxyl group or groups are substituted by a (C$_1$–C$_5$)alkoxyalkyl in which the alkyl is C$_1$–C$_4$, a tetrahydrofuranyl or a tetrahydropyranyl are deprotected. This deprotection is effected in an acid medium, for example in the presence of a mineral or organic acid, in an alcohol or ether solvent such as THF, at a temperature between 15° C. and the reflux temperature; the deprotection can be carried out for example in the presence of hydrochloric acid or pyridinium toluenesulfonate in an alcohol.

To obtain the compounds of formula (I) in which R$_3$ and R$_4$, together with the carbon to which they are bonded, form an optionally fused, saturated or unsaturated C$_3$–C$_{12}$ hydrocarbon ring substituted by one or two ω-hydroxy(C$_1$–C$_4$) alkoxy groups, the corresponding compounds of formula (I) in which R$_3$ and R$_4$, together with the carbon to which they are bonded, form an optionally fused, saturated or unsaturated $C_3$–$C_{12}$ hydrocarbon ring substituted by one or two ($C_1$–$C_5$)alkoxy($C_1$–$C_4$)alkoxy groups are deprotected. This deprotection is effected in an acid medium, for example trifluoroacetic acid, in a solvent such as DCM.

Compounds of formula (I) in which $R_3$ and $R_4$, together with the carbon to which they are bonded, form an optionally fused, saturated or unsaturated $C_3$–$C_{12}$ hydrocarbon ring substituted by one or two ($C_1$–$C_4$)-alkoxy groups or one or two ($C_1$–$C_5$)alkoxy($C_1$–$C_4$)alkoxy groups can also be prepared by alkylating compounds of formula (I) in which $R_3$ and $R_4$, together with the carbon to which they are bonded, form an optionally fused, saturated or unsaturated $C_3$–$C_{12}$ hydrocarbon ring substituted by one or two hydroxyls. This alkylation is carried out more particularly with powerful alkylating reagents such as alkyl trifluoromethanesulfonates, in solvents such as DCM or carbon tetrachloride, in the presence of a base such as 2,6-di-tert-butylpyridine, by the method described in Carbohydrate Research, 1975, 44, C5–C7. The alkyl trifluoromethanesulfonates can be obtained from the alkyl iodides by reaction with a trifluoromethanesulfonic acid salt such as the silver salt (Chemical Reviews, 1977, 77).

Compounds of formula (I) in which $R_3$ and $R_4$, together with the carbon to which they are bonded, form an optionally fused, saturated or unsaturated $C_3$–$C_{12}$ hydrocarbon ring substituted by one or two $C_1$–$C_7$-acyloxy groups can be prepared by reacting dimethyl sulfate in the presence of cesium carbonate or, respectively, by reacting an acid halide or an anhydride with a compound of formula (I) in which $R_3$ and $R_4$, together with the carbon to which they are bonded, form an optionally fused, saturated or unsaturated $C_3$–$C_{12}$ hydrocarbon ring substituted by one or two hydroxyls.

A compound of formula (I) in which $R_3$ and $R_4$, together with the carbon to which they are bonded, form a tricyclo[5.2.1.0$^{2,6}$]decane-8,9-diol can also be obtained from a compound of formula (I) in which $R_3$ and $R_4$, together with the carbon to which they are bonded, form a tricyclo[5.2.1.0$^{2,6}$]dec-8-ene, which is reacted with metachloroperbenzoic acid at room temperature, in a solvent such as DCM, to give an intermediate compound of formula (I) in which $R_3$ and $R_4$, together with the carbon to which they are bonded, form a tricyclo[5.2.1.0$^{2,6}$]decan-8,9-epoxy; the intermediate epoxide derivative is then hydrolyzed by refluxing in water in the presence of sulfuric acid or in a basic medium.

The compounds of formula (II) in which $R'_3$ and $R'_4$, together with the carbon to which they are bonded, form either an optionally fused, saturated or unsaturated $C_3$–$C_{12}$ hydrocarbon ring substituted by an oxo group, or a group —(CH$_2$)$_p$—X—(CH$_2$)$_q$— in which X is a group SO, SO$_2$ or N(O)R$_{13}$, are prepared by known oxidation reactions starting from the corresponding compounds of formula (II) in which $R'_3$ and $R'_4$, together with the carbon atom to which they are bonded, respectively form either an optionally fused, saturated or unsaturated $C_3$–$C_{12}$ hydrocarbon ring substituted by a hydroxyl, or a group —(CH$_2$)$_p$—X—(CH$_2$)$_q$— in which X is a sulfur atom or a group NR$_{13}$.

For example, the oxidation of secondary alcohols to ketones can be carried out in the presence of chromium oxide complexes such as pyridinium chlorochromate, in an inert solvent such as methylene chloride, or with oxidizing agents such as DMSO, by the methods described in Tetrahedron, 1978, 34, 1651.

The oxidation of the compounds (II) containing a sulfur or nitrogen atom (X=S, NR$_{13}$) can be effected in the presence of hydrogen peroxide or peracids such as peracetic or metachloroperbenzoic acid, in inert solvents such as ketones or acetic acid, at temperatures between 0° C. and 50° C.

If $R'_3$ and $R'_4$ are each a phenyl, the process described in Helv. Chim. Acta, 1946, 29, 415–432, can be used to prepare a compound (II).

The 1,3-dihydroindol-2-one derivatives (VII) are known or are prepared by known methods. An example which may be cited is J. V. RajanBabu in J. Org. Chem., 1986, 51, 1704–1712.

The compounds of formula (II) which carry certain substituents $R'_1$ and $R'_2$ on their benzene moiety are used as precursors for the preparation of compounds of formula (II) which carry other substituents $R'_1$ and $R'_2$. For example, the compounds (II) in which $R'_1$ and/or $R'_2$=H can be nitrated with the conventional reagents; they can also be acylated by reaction with an acid chloride of the formula RCOCl, in which R is a $C_1$–$C_7$-alkyl, in the presence of a Lewis acid such as aluminum chloride, in order to prepare a compound (II) in which $R'_1$ and/or $R'_2$=—COR. The compound (II) in which $R'_1$ is an amino group is prepared by the catalytic hydrogenation of a compound (II) in which $R'_1$ is a nitro group and $R'_2$ is hydrogen.

The compounds of the formula

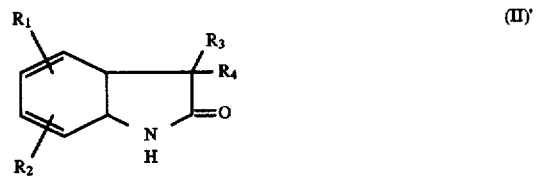

(II)' in which $R_1$ and $R_2$ are each independently a hydrogen, a hydroxy, a ω-halogeno-$C_1$–$C_4$-alkoxy, a halogen, a $C_1$–$C_4$-alkyl, a trifluoromethyl, a $C_1$–$C_7$-alkoxy, a $C_1$–$C_4$-polyhalogenoalkoxy, a ω-hydroxy-$C_2$–$C_4$-alkoxy, an ω-methoxyalkoxy in which the alkyl is $C_2$–$C_4$, an ω-amino-$C_2$–$C_4$-alkoxy which is free or substituted by one or two $C_1$–$C_4$-alkyls; a $C_3$–$C_7$-cycloalkoxy; a cycloalkylmethoxy in which the cycloalkyl is $C_3$–$C_7$; a phenoxy; a benzyloxy; a $C_1$–$C_4$-alkylthio; a phenylthio; a nitro; an amino which is free or substituted by one or two $C_1$–$C_4$-alkyls; a cyano; a $C_1$–$C_4$-acyl; a $C_1$–$C_4$-acyloxy; a $C_1$–$C_4$-alkylsulfonamido; a phenylsulfonamido; a $C_1$–$C_4$-alkylamido; a $C_1$–$C_4$-alkoxycarbonylamino or a ureido which is unsubstituted or substituted by a phenyl or by one or two $C_1$–$C_4$-alkyls; and $R_3$ and $R_4$, together with the carbon to which they are bonded, form an adamantane, an indane or a hexahydroindane which are unsubstituted or substituted oby one or more $C_1$–$C_7$-alkyl groups, a tricyclo[5.2.1.0$^{2,6}$]decane or a tricyclo[5.2.1.0$^{2,6}$]dec-8-ene which are unsubstituted or substituted by one or more $C_1$–$C_7$-alkyl groups, or a $C_4$–$C_8$ hydrocarbon ring substituted by one or more $C_1$–$C_7$-alkyl groups or by a $C_3$–$C_5$-spirocycloalkyl; or else $R_3$ and $R_4$ together form a group —(CH$_2$)$_p$—X(CH$_2$)$_q$— in which p and q are integers whose sum can vary from 3 to 6 and X is oxygen, sulfur or a group NR$_{13}$. $R_{13}$ being a phenyl, a benzyl, a $C_1$–$C_4$-acyl, a $C_1$–$C_4$-alkoxycarbonyl or a carbamoyl which is unsubstituted or substituted by one or two $C_1$–$C_4$-alkyls, with the limitation that if CR$_3$R$_4$ is adamantane, $R_1$ and $R_2$ are other than hydrogen, are novel and form part of the invention.

The compounds of the formula

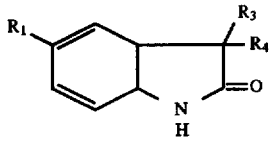

(II)″ in which

R$_1$ is a hydroxy, an ω-halogeno-C$_1$-C$_4$-alkoxy, a halogen, a C$_1$-C$_4$-alkyl, a trifluoromethyl, a C$_1$-C$_7$-alkoxy, a C$_1$-C$_4$-polyhalogenoalkoxy, an ω-hydroxy-C$_2$-C$_4$-alkoxy, an ω-methoxyalkoxy in which the alkyl is C$_2$-C$_4$, an ω-amino-C$_2$-C$_4$-alkoxy which is free or substituted by one or two C$_1$-C$_4$-alkyls; a C$_3$-C$_7$-cycloalkoxy; a cycloalkylmethoxy in which the cycloalkyl is C$_3$-C$_7$; a phenoxy; a benzyloxy; a C$_1$-C$_4$-alkylthio; a phenylthio; a nitro; an amino which is free or substituted by one or two C$_1$-C$_4$-alkyls; a cyano; a C$_1$-C$_4$-acyl; a C$_1$-C$_4$-acyloxy; a C$_1$-C$_4$-alkylsulfonamido; a phenylsulfonamido; a C$_1$-C$_4$-alkylamido; a C$_1$-C$_4$-alkoxycarbonylamino or a ureido which is unsubstituted or substituted by a phenyl or by one or two C$_1$-C$_4$-alkyls;

R$_3$ and R$_4$ together form a group —(CH$_2$)$_p$—X(CH$_2$)$_q$—; or

R$_3$ and R$_4$, together with the carbon to which they are bonded, form an optionally fused, saturated or unsaturated C$_3$-C$_{12}$ hydrocarbon ring which is unsubstituted or substituted by one or more C$_1$-C$_7$-alkyl groups or by a C$_3$-C$_5$-spirocycloalkyl;

p and q are each an integer, it being possible for their sum to vary from 3 to 6;

X is oxygen, sulfur or a group NR$_{13}$; and

R$_{13}$ is hydrogen, a C$_1$-C$_4$-alkyl, a phenyl, a benzyl, a C$_1$-C$_4$-acylo, a C$_1$-C$_4$-alkoxycarbonyl or a carbamoyl which is unsubstituted or substituted by one or 2 C$_1$-C$_4$-alkyls, with the limitation that if R$_1$ is methoxy, CR$_3$R$_4$ is other than a pyrrolidine-3 which is unsubstituted or N-substituted by a C$_1$-C$_4$-alkyl, and if R$_1$ is a halogen, CR$_3$R$_4$ is other than a pentane, are novel and form part of the invention.

2a,3,4,5-Tetrahydrobenz[c,d]indol-2(1H)-one of the formula

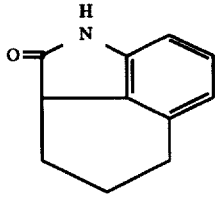

is commercially available; its derivatives are known or are prepared by known methods.

The benzenesulfonyl halides (III) are prepared by known methods. Thus, for example, 4-dimethylaminobenzenesulfonyl chloride is prepared according to C. N. Sukenik et al., J. Amer. Chem. Soc., 1977, 99, 851–858. More generally, the benzenesulfonyl halides (III) in which the substituent R'$_5$ is a dimethylamino group are known or are prepared by known methods; p-benzyloxybenzenesulfonyl chloride is prepared according to European patent application EP 229 566.

The alkoxybenzenesulfonyl chloride is prepared from the sodium alkoxybenzenesulfonate, which is itself prepared by reacting an alkyl halide with sodium hydroxybenzenesulfonate.

2,4-Dimethoxybenzenesulfonyl chloride is prepared according to J. Am. Chem. Soc., 1952, 74, 2008.

The halogenoalkoxybenzenesulfonyl chlorides can be prepared according to patent U.S. Pat. No. 2,540,057.

The benzenesulfonyl halides of the formula

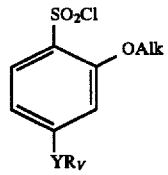

(III)' in which

Alk is a C$_1$-C$_7$-alkyl;

Y is O or S; and

R$_V$ is a C$_1$-C$_7$-alkyl, a C$_3$-C$_7$-cycloalkyl, a C$_2$-C$_7$-alkenyl, an ω-halogeno-C$_1$-C$_7$-alkyl, a polyhalogeno-C$_1$-C$_7$-alkyl, a benzyl, a C$_1$-C$_7$-acyl or an ω-carboxy-C$_1$-C$_7$-alkyl esterified by a C$_1$-C$_4$-alkyl or a benzyl, are novel and form part of the invention. These compounds are prepared according to D. Hofmann et al. in Liebigs Ann. Chem., 1982, 287–297.

Benzene compounds carrying the substituents YR$_V$ and OAlk in the 1- and 3-positions are reacted with trimethylsilyl chlorosulfonate in a solvent such as DCM, at RT. The method of R. Passerini et al. in Gazz. Chim. Ital., 1960, 90, 1277–89, is then applied and this is followed by neutralization, for example with alkali metal carbonate, and then by reaction with a halide such as POCl$_3$ to give the desired benzenesulfonyl halide.

The benzenesulfonyl halides (III) in which the substituent R'$_5$ is an alkoxycarbonyl, a phenoxycarbonyl, a benzyloxycarbonyl, an alkylthio, a phenylthio, a benzylthio or a group —SR$_7$, R$_7$ being as defined for (I), are prepared according to Col. Czechoslov. Chem. Commun., 1984, 49, 1184, from an aniline derivative substituted by the same grouping R'$_5$, said aniline derivative itself being obtained from the corresponding nitro derivative.

The nitrobenzoic acid derivatives are known; the corresponding alkyl and phenyl esters are obtained by subjecting this acid to an appropriate esterification reaction.

The benzenedisulfonyl dihalides (III, R$_5$'=—SO$_2$Hal) are known or are prepared by known methods. For example, 2,4-dimethoxybenzene-1,5-disulfonyl dichloride is described in R. J. W. Cremlyn, J. Chem. Soc. C, 1969, 1344.

The halogenoalkoxybenzenesulfonyl chlorides (III, R'$_5$= ω-halogenoalkoxy) are used to prepare compounds according to the invention in which the substituent R$_5$ is an ω-aminoalkoxy which is unsubstituted or substituted by one or two alkyls, according to the following equation:

—O—Alk'—Hal+NHAA'→—O—Alk'—NAA' in which Alk' is a C$_2$-C$_7$-alkyl and A and A' are independently hydrogen or a C$_1$-C$_7$-alkyl.

For certain meanings of the substituents R$_1$, R$_2$, R$_5$ and/or R$_6$, the compounds (I) according to the invention can be prepared from a precursor of formula (I') substituted by a group R'$_1$, R'$_2$, R'$_5$ and/or R$_{V'}$, called a precursor group of R$_1$, R$_2$, R$_5$ and/or R$_6$, by using methods known to those skilled in the art.

The description which follows relates to the preparation of the compounds of formula (I) carrying substituents R$_1$ and/or $R_5$; the same methods apply to the preparation of the compounds in which the substituents $R_2$ and/or $R_6$ have the meanings indicated for $R_1$ and $R_5$.

The compounds (I) in which $R_1$ and/or $R_5$ are a hydroxyl can be obtained by the catalytic hydrogenation of a compound of formula (I') in which $R'_1$ and/or $R'_5$ are a benzyloxy, for example in the presence of palladium-on-charcoal. These compounds can also be prepared from analogous compounds of formula (I') in which $R'_1$ and/or $R'_5$ are an amino group by using the method described in J. Org. Chem., 1977, 42, 2053.

The compounds of formula (I) in which $R_1$ and/or $R_5$ are a $C_1$–$C_7$-alkoxy can be prepared directly by the process according to the invention starting from the correctly substituted compounds of formulae (II) and (III).

The compounds (I') in which $R'_1$ and/or $R'_5$ are a hydroxyl can also be used to prepare compounds (I) in which $R_1$ and/or $R_5$ are a $C_1$–$C_7$-alkoxy by reaction with a $C_1$–$C_7$-alkyl halide in the presence of a base such as a metal hydride or an alkali metal or alkaline earth metal carbonate like $K_2CO_3$ or $Cs2CO_3$, in a solvent such as THF or DMF. Likewise, the compounds of formula (I) in which $R_1$ and/or $R_5$ are an ω-aminoalkoxy are prepared by reacting an ω-chloroalkylamine with the compounds in which $R'_1$ and/or $R'_5$=OH; similarly, the compounds in which $R_1$ and/or $R_5$ are an ω-hydroxyalkoxy are prepared by reaction with a chloroalkyl alcohol; in the particular case of the preparation of a compound (I) in which $R_1$ and/or $R_5$=—O(CH$_2$)$_2$OH, it is also possible to react ethylene carbonate with a compound (I') in which $R'_1$ and/or $R'_5$=OH.

The compounds of formula (I) in which $R_1$ and/or $R_5$ are a $C_1$–$C_7$-acyloxy which is a $C_1$–$C_6$-alkylcarbonyloxy are obtained by reacting an acid halide or an anhydride with a compound (I') in which $R'_1$ and/or $R'_5$ are a hydroxyl.

The compounds of formula (I) in which $R_1$ and/or $R_5$ are a formyloxy are obtained for example by reacting formic acid in the presence of dicyclohexylcarbodiimide with a compound (I') in which $R'_1$ and/or $R'_5$ are a hydroxyl (J. HUANG et al. J. Chem. Res.(S), 1991, 292–293).

The compounds of formula (I) in which $R_5$ is a group —$OR_7$, $R_7$ being an ω-carbamoyl-$C_1$–$C_7$-alkyl which is free or substituted by one or two $C_1$–$C_7$-alkyls, can be prepared from a compound (I') in which $R'_5$ is a group —$OR_V$, $R_V$ being an ω-carboxy-$C_1$–$C_7$-alkyl esterified by a $C_1$–$C_7$-alkyl. This preparation is carried out by reaction with a correctly chosen amine in a manner conventional to those skilled in the art.

To prepare compounds of formula (I) in which $R_1$ and/or $R_5$ are a $C_1$–$C_7$-monoalkylamino, a compound of formula (I') in which $R'_1$ and/or $R'_5$ are an amino group is reacted with an aldehyde or ketone in an acid medium, in the presence of a reducing agent such as sodium cyanoborohydride; the compounds (I) in which $R_1$ and/or $R_5$ are a dialkylamino are prepared by an identical reaction.

The compounds of formula (I) in which $R_5$ is an amino group substituted by a benzyl, which is itself optionally substituted, or by a $C_3$–$C_8$-alkene in which the double bond may be in the $C_3$–$C_4$ position, can be prepared by reacting a benzyl chloride or a $C_3$–$C_8$-chloroalkene with a compound of formula (I') in which $R'_5$ is an amino or alkylamino group.

The compounds of formula (I) in which $R_5$ is a Δ3-pyrrolin-1-yl group are prepared by reacting cis-1,4-dichlorobut-2-ene with the compounds of formula (I') in which $R'_5$ is an amino group, in the presence of a base such as triethylamine, under an inert atmosphere. The compounds of formula (I) in which $R_5$ is a pyrrolidin-1-yl group are then prepared by hydrogenation. The reaction of cis-1,4-dichlorobut-2-ene with the compounds (I') in which $R'_5$ is an amino group can also be carried out in air, in the presence of a base such as sodium carbonate, under which conditions it results in the formation of a mixture of a compound of formula (I) in which $R_5$ is a Δ3-pyrrolin-1-yl and a compound of formula (I) in which $R_5$ is a pyrrol-1-yl group, which can be separated by chromatography.

The compounds of formula (I) in which $R_5$ is an isoindolin-2-yl group are prepared by reacting α,α'-dibromo-o-xylene with the compounds of formula (I') in which $R'_5$ is an amino group, in the presence of a base such as triethylamine, and in a solvent such as dimethylformamide, under reflux.

The compounds of formula (I) in which $R_5$ is a 1-methyl-2,4-dioxoimidazolin-3-yl group ($NR_8R_9$=N-methylhydantoin) are prepared in two steps: Sarcosine is reacted with a compound of formula (I') in which $R'_5$ is a phenoxycarboxamido, in the presence of a base such as triethylamine, to give a compound of formula (I') in which $R'_5$ is an N'-carboxymethyl-N'-methylureido; the previously obtained product then cyclizes on heating at 100° C. under vacuum the compounds of formula (I) in which $R_5$ is a 2,4-dioxoimidazolin-3-yl group ($NR_8R_9$=hydantoin) are prepared in the same manner by reacting glycine with a compound of formula (I') as defined above.

If $R'_1$ and/or $R'_5$ are an amino, it is also possible to perform a nitrosation, for example in the presence of nitrous acid or sodium nitrite, in order to prepare a compound (I') in which $R'_1$ and/or $R'_5$ are a diazonium salt; reactions known to those skilled in the art then afford the compounds (I) according to the invention in which $R_1$ and/or $R_5$ are a cyano, a halogeno or a $C_1$–$C_7$-thioalkyl. Finally, compounds (I) in which $R_1$ and/or $R_5$ are a group of the formula RCONH—, ROCONH—, RNHCONH— or RSO$_2$NH—, in which R is a $C_1$–$C_7$-alkyl, a phenyl or a benzyl, can be prepared by conventional reactions starting from compounds (I') in which $R'_1$ and/or $R'_5$=NH$_2$.

The compounds of formula (I) in which $R_5$ is a $C_1$–$C_7$-alkoxycarbonyl can be prepared directly by the process according to the invention. Using methods known to those skilled in the art, they make it possible to obtain the compounds of formula (I) in which $R_5$ is a carboxyl group.

The compounds of formula (I') in which $R'_5$ is a benzyloxycarbonyl can also be used to obtain the compounds (I) in which $R_5$ is a carboxyl by catalytic hydrogenation. Reaction with a thionyl halide gives the compounds of formula (I') in which $R'_5$ is a halogenocarbonyl. Such compounds are used to prepare compounds of formula (I) in which $R_5$ is a carbamoyl substituted by $R'_6$ and $R"_6$ by reaction with a compound HNR'$_6$R"$_6$. The compounds of formula (I') in which the substituent $R'_5$ is a phenoxycarbonyl can also be used to obtain the compounds (I) in which $R_5$ is a phenylcarbamoyl or a $C_1$–$C_7$-alkylcarbamoyl by reaction with an aniline or a $C_1$–$C_7$-alkylamine. An aniline substituted on the phenyl or an alkylamine substituted on the alkyl can be used to obtain compounds of formula (I) in which $R_5$ is a phenylcarbamoyl substituted on the phenyl or, respectively, an alkylcarbamoyl substituted on the alkyl by $R_6"$.

In the same way, the compounds of formula (I) in which $R_5$ is a group —CONHCR$_{10}$R'$_{10}$COR$_{12}$ are prepared from compounds of formula (I') in which $R'_5$ is either a group —COCl or a phanoxycarbonyl group by reaction with H$_2$NCR$_{10}$R'$_{10}$COR$_{12}$.

The compounds of formula (I) in which $R_5$ is a group —COR'$_7$ are prepared from corresponding compounds (I') in which $R'_5$ is a phenoxycarbonyl by reaction with R'$_7$H.

The compounds of formula (I) in which $R_5$ is a group $COR_7$, are prepared from corresponding compounds (I') in which $R'_5$ is a phenoxycarbonyl by reaction with a substituted piperazine or azetidine.

A compound (I') in which $R'_5$ is a nitro group makes it possible to obtain a compound (I) in which $R_5$ is an amino group by catalytic hydrogenation, for example in the presence of platinum oxide, Raney® nickel or palladium-on-charcoal, or by chemical reduction, for example in the presence of tin or iron in an acid medium; other compounds in which the amino group is substituted can then be prepared using reactions well known to those skilled in the art.

For example, if it is desired to obtain a compound (I) according to the invention in which $R_5$ is a group $-NR_8R_9$, $R_9$ being an optionally substituted benzoyl, benzoyl chloride in which the phenyl carries the appropriate substituent is reacted with a compound (I') in which $R'_5$ is an amino group, in the presence of an amine such as triethylamine. For example, 4-chlorosulfonylbenzoyl chloride can be reacted in order to prepare a compound (I') in which $R'_5$ is a 4-chlorosulfonylbenzamido group, after which a compound (I) in which the substituent $R_5$ is a 4-sulfamoylbenzamido group or a 4-alkylsulfamoylbenzamido group is obtained by reaction with ammonia or a $C_1-C_4$-alkylamine respectively. In the same way, the acid chloride $R_{11}R'_{11}NCR_{10}R'_{10}COCl$ is reacted with a compound of formula (I') in which $R'_5$ is a group $-NHR_8$ in order to prepare a compound of formula (I) in which $R_5$ is an $-NR_8$ substituted by $-COCR_{10}R'_{10}NR_{11}R'_{11}$.

If it is desired to prepare a compound (I) in which $R_5$ is a group $-NR_8R_9$, $R_9$ being a $C_1-C_7$-acyl which is a $C_1-C_6$-alkylcarbonyl, the appropriate anhydride or the appropriate acid chloride is reacted with a compound (I') in which $R'_5$ is an amino group, in the presence of an amine such as triethylamine. To prepare a compound (I) in which $R_5$ is a group $-NR_8R_9$, $R_9$ being a formyl, formic acid is reacted with a compound (I') in which $R'_5$ is an amino group, in the presence of acetic anhydride and of an amine such as triethylamine.

In another preparatory example, a compound (I) in which $R_5$ is an alkylsulfonamido group is obtained by reacting an alkylsulfonyl halide with a compound (I') in which $R'_5$ is an amino group.

The compounds of formula (I') in which $R'_5$ is an amino group are also useful for the preparation of compounds in which this amino group is substituted by a group $-(CH_2)_{t'}-COR_{12}$. In this case, a compound of the formula Hal—$(CH_2)_{t'}$—COOAlk, in which Hal is a halogen, for example bromine, and Alk is a $C_1-C_7$-alkyl, is reacted with (I') in the presence of cuprous chloride; if required, the resulting ester is converted to the acid or an amide.

A compound (I) in which $R_5=-NHCO-(CH_2)_{t'}-CO_2H$, where t'=2 or 3, can be prepared by reacting an anhydride, such as succinic anhydride or glutaric anhydride, with a compound (I') in which $R'_5$ is an amino. If required, the resulting acid is converted to an ester or an amide.

A compound (I) in which $R_5=-NHCOCO_2Et$ or $-NHCOCH_2CO_2Et$ can be prepared by reacting ethyloxalyl chloride, or, respectively, ethylmalonylchloride, with a compound (I') in which $R'_5$ is an amino.

In the same way, the compounds of formula (I) in which $R_5$ is an amino group substituted by a group $-CR_{10}R'_{10}COR_{12}$ are prepared by reacting a compound of the formula Hal—$CR_{10}R'_{10}COR_{12}$ with the corresponding compounds (I') in which the substituent $R'_5$ is an amino.

A compound (I) in which $R_5$ is an amino group substituted by a $C_1-C_7$-alkoxycarbonyl or a phenoxycarbonyl is prepared by reacting a $C_1-C_7$-alkyl or phenyl chloroformate with a compound (I') in which the substituent $R'_5$ is an amino.

Likewise, a compound of formula (I) in which $R_5$ is a phenoxythiocarbonylamino is obtained by reacting a phenoxythiocarbonyl chloride with a compound of formula (I') in which $R'_5$ is an amino group.

A compound of formula (I) in which $R_5$ is a ureido or a thioureido is prepared by reacting ammonia with a compound of formula (I') in which $R'_5$ is an amino group substituted by a phenoxycarbonyl or a phenoxythiocarbonyl; such a compound of formula (I') is reacted with a correctly substituted aniline or a correctly substituted $C_1-C_7$-monoalkylamine or -dialkylamine in order to prepare a compound of formula (I) in which $R_5$ is a correctly substituted N'-phenylureido or a correctly substituted N'-alkylureido or N',N'-dialkylureido in which the alkyl is $C_1-C_7$.

It is also possible to prepare a compound (I) in which $R_5$ is a ureido ($-NHCONR_{14}R'_{14}$) or a thioureido ($-NHCSNR_{14}R'_{14}$) by reacting a compound $NHR_{14}R'_{14}$ with a compound of formula (I') in which $R'_5$ is a phenoxycarbonylamino or, respectively, phenoxythiocarbonylamino group.

It is also possible to prepare a compound (I) in which $R_5$ is a ureido ($-NHCONR_{14}R'_{14}$) or a thioureido by reacting a carbamoyl chloride ($ClCONR_{14}R'_{14}$) or, respectively, a thiocarbomoyl chloride with a compound of formula (I') in which $R'_5$ is an amino group.

A further possibility is to prepare a compound (I) in which $R_5$ is a thioureido by reacting Lawesson's reagent with a compound (I') in which $R'_5$ is the corresponding ureido.

The compounds (I) in which $R_5$ is a guanidino group which is unsubstituted or monosubstituted or disubstituted by a $C_1-C_7$-alkyl, a phenyl or a benzyl can be prepared from the compounds (I') in which $R'_5$ is a phenoxyamido group by reaction with cyanamide or a derivative thereof correctly substituted on the nitrogen.

A compound (I) in which $R_5$ is a carbamoyl which is unsubstituted or substituted by one or 2 $C_1-C_7$-alkyl groups is prepared by reacting an appropriate amine with a compound (I') in which the substituent $R'_5$ is an amino, in the presence of phosgene.

It is also possible to prepare a compound (I) in which $R_5$ is an amino group substituted by an alkylcarbamoyl or a phenylcarbamoyl by reacting an alkyl or phenyl isocyanate with a compound (I') in which the substituent $R'_5$ is an amino.

Furthermore, a compound (I) in which $R_5$ is a sulfamoyl group which is unsubstituted or substituted by a $C_1-C_7$-alkyl is prepared by reacting ammonia or a $C_1-C_7$-alkylamine with a compound (I') in which $R'_5$ is a halogenosulfonyl group.

The compounds of formula (I)' which are useful as precursors for the preparation of compounds of formula (I) are included in formula (I) and form part of the invention.

Among the compounds of formula (I), the compounds of formulae (IX), (X), (XII) and (XIII) below, which are useful for the preparation of other compounds of formula (I), are preferred compounds according to the invention.

Thus one subject of the present invention consists of the compounds of the formula

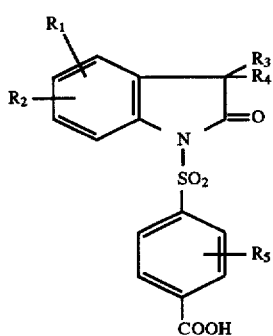

in which $R_1$, $R_2$, $R_3$, $R_4$ and $R_5$ are defined as indicated above for (I), and their functional derivatives such as their esters.

Another subject of the present invention consists of the compounds of the formula

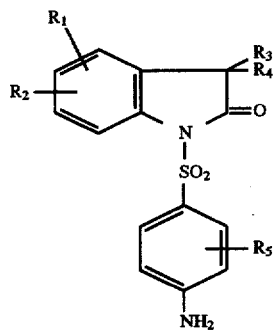

in which $R_1$, $R_2$, $R_3$, $R_4$ and $R_5$ are defined as indicated above for (I), and their salts where appropriate.

Yet another subject of the present invention consists of compounds of the formula

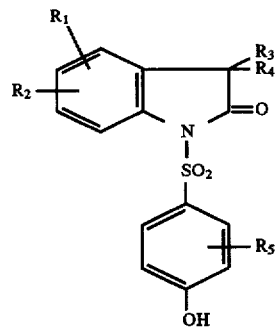

in which $R_1$, $R_2$, $R_3$, $R_4$ and $R_5$ are defined as indicated above for (I).

Another subject of the present invention consists of compounds of the formula

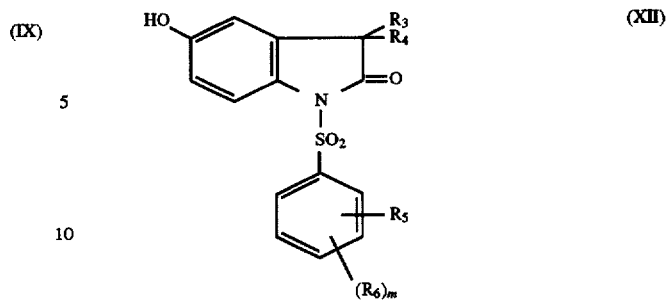

in which $R_3$, $R_4$, $R_5$, $R_6$ and m are defined as indicated above for (I).

Yet another subject of the present invention consists of the compounds of the formula

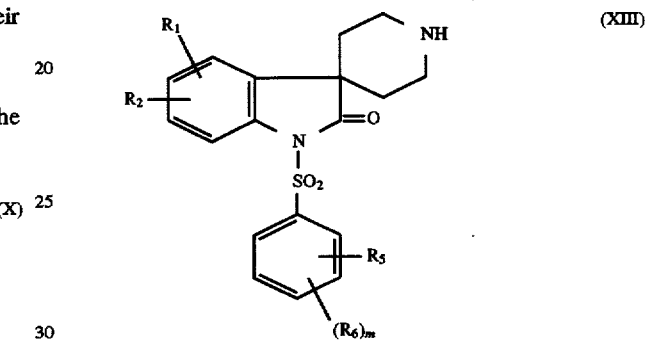

in which $R_1$, $R_2$, $R_5$, $R_6$ and m are defined as indicated above for (I).

The affinity of the compounds according to the invention for the vasopressin receptors was determined in vitro using the method described in C. J. Lynch et al., J. Biol. Chem., 1985, 260 (5), 2844–2851. This method consists in studying the displacement of tritiated vasopressin bound to the $V_1$ sites of rat liver membranes. The concentrations of the compounds according to the invention which cause a 50% inhibition of the binding of tritiated vasopressin ($IC_{50}$) are low, ranging down to $10^{-7}$M.

The affinity of the compounds (I) according to the invention for the $V_2$ receptors was measured on a bovine kidney membrane preparation by a method adapted from P. Crause et al., Molecular and Cellular Endocrinology, 1982, 28, 529–541, and F. L. Stassen et al., J. Pharmacol. Exp. Ther., 1982, 223, 50–54. The compounds according to the invention inhibit the binding of tritiated arginine vasopressin to the receptors of the membrane preparation. The $IC_{50}$ values of the compounds according to the invention are low, ranging down to $10^{-9}$M.

The antagonistic activite of the compounds according to the invention towards the $V_2$ receptors was demonstrated by the adenylate cyclase activity assay performed by a method adapted from M. Laburthe et al., Molecular Pharmacol., 1986, 39, 23–27. A bovine kidney membrane preparation is used and each product is incubated for 10 minutes at 37° C., either by itself or in the presence of AVP (arginine vasopressin) at a concentration of $3.10^{-8}$M. The cyclic AMP (cyclic adenosine monophosphate) produced is measured by radioimmunoassay. The concentration which causes a 50% inhibition ($IC_{50}$) of the stimulation of adenylate cyclase induced by $3.10^{-8}$M AVP is determined. The $IC_{50}$ values determined are of the order of $10^{-7}$M, ranging down to $10^{-8}$M.

The agonistic or antagonistic activity of the compounds according to the invention, administered orally, towards the vasopressin receptors is evaluated in hyperhydrated rats (OFA, Sprague-Dawley strain) treated with vasopressin. The antagonistic activity of the compounds according to the invention was also evaluated in normally hydrated rats (OFA strain or Sprague-Dawley strain) by the technique described in Br. J. Pharmacol., 1992, 105, 787–791. The diuretic effect was observed for some of the compounds at a dose of 10 mg/kg.

Likewise, the affinity of the compounds (I) according to the invention for the ocytocin receptors was determined in vitro by the displacement of a radioiodinated ocytocin analog bound to the receptors of a gestating rat mammary gland membrane preparation by a technique similar to that described by J. Eland et al. in Eur. J. Pharmacol., 1987, 147, 197–207. The $IC_{50}$ values of the compounds according to the invention reach $10^{-8}M$.

The compounds according to the invention are active after administration by different routes, especially orally.

No signs of toxicity are observed with these compounds at the pharmacologically active doses.

Thus the compounds according to the invention can be used in the treatment or prevention of various vasopressin-dependent or ocytocin-dependent complaints, cardiovascular complaints such as hypertension, pulmonary hypertension, cardiac insufficiency, nyccardial infarction or coronary vasospasm, in particular in smokers, unstable angina and PTCA (percutaneous transluminal coronary angioplasty), cardiac ischemia, hemostatic disorders, especially hemophilia, and von Willebrand's syndrome, complaints of the central nervous system, for example migraine, cerebral vasospasm, cerebral hemorrhage, cerebral edemas, depression, anxiety, psychotic states and memory disorders, complaints of the renal system, such as edemas, renal vasospasm, necrosis of the renal cortex, hyponatremia, hypokalemia end Schwartz Bartter's syndrome, complaints of the gastric system, such as gastric vasospasm, hepatccirrhosis, ulcers, the pathology of vomiting, for example nausea, including nausea due to chemotherapy, travel sickness or else the syndrome of inappropriate secretion of antidiuretic hormone (SIADH), diabetes insipidus and enuresis. The compounds according to the invention can also be used in the treatment of disorders of sexual behavior; in women, the compounds according to the invention can be used for treating dysmenorrhea or premature labor. The compounds according to the invention can also be used in the treatment of small cell lung cancer, hyponatremic encephalopathy, Raynaud's disease, pulmonary syndrome and glaucoma and in postoperative treatments, especially after abdominal surgery.

The present invention further relates to pharmaceutical compositions containing an effective dose of a compound according to the invention, or a pharmaceutically acceptable salt, and suitable excipients.

Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or their salts where appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight and per day.

Each unit dose can contain from 0.5 to 1000 mg, preferably from 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

If a solid composition is prepared in the form of tablets, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient together with a sweetener, which is preferably calorie-free, methylparaben and propylparaben as antiseptics, a flavoring and an appropriate color.

The water-dispersible powders or granules can contain the active ingredient mixed with dispersants or wetting agents, or suspension agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, if appropriate with one or more carriers or additives.

In addition to the products of formula (I) above or one of the pharmaceutically acceptable salts, the compositions of the present invention can contain other active principles which may be useful in the treatment of the disorders or diseases indicated above.

Thus the present invention further relates to pharmaceutical compositions in which several active principles are present in association, one of them being a compound according to the invention.

Thus, according to the present invention, it is possible to prepare pharmaceutical compositions in which a compound according to the invention is present in association with a compound which acts on the renin-angiotensin system, such as a converting enzyme inhibitor, an angiotensin II antagonist or a renin inhibitor. A compound according to the invention can also be associated for example with a peripheral vasodilator, a calcium inhibitor, a beta-blocker, an alpha-1- blocker or a diuretic. Such compositions will be useful in particular in the treatment of hypertension or heart failure.

It is also possible to associate two compounds according to the invention, namely a specific $V_1$ receptor antagonist with a specific $V_2$ receptor antagonist, or else a specific $V_1$ receptor antagonist with a specific ocytocin antagonist.

These associations will make it possible to reinforce the therapeutic activities of the compounds according to the invention.

Preparation of the 1,3-dihydroindol-2-ones

Preparation 1:

1,3-Dihydro-4,6-dimethyl-3-spirocyclohexaneindol-2-one

This compound is prepared according to Moore and Plant in J. Chem. Soc., 1951, 3475.

A mixture containing 15 ml of quinoline and 10 g of calcium oxide is refluxed under an inert atmosphere and 5 g of the 3,5-dimethylphenylhydrazide of cyclohexanecarboxylic acid (IV, R'$_1$, R'$_2$=CH$_3$, CR'$_3$R'$_4$=cyclohexane) are added over 30 minutes. The reaction medium is cooled and then poured into an ice/hydrochloric acid mixture. Extraction is carried out with ethyl acetate and the extract is washed with normal hydrochloric acid and with water until the washings are neutral, and then dried and concentrated under vacuum to give a brown solid. Trituration in iso ether gives the expected compound. M.p.=223° C.

The 1,3-dihydroindol-2-one derivatives described in Table 1 below are obtained by following the same procedure and varying the starting hydrazide.

These compounds are purified by chromatography on a silica column using DCM as the eluent or by chromatography on an alumina column using DCM or iso ether as the eluent.

TABLE 1

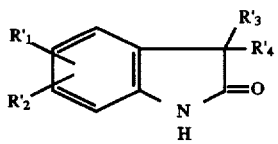

| R'$_1$ | R'$_2$ | CR'$_3$R'$_4$ | M.p. °C. |
|---|---|---|---|
| Cl-5 | H | cyclobutane | 191 |
| Cl-5 | H | cyclopentane | 189 |
| Cl-5 | H | cyclohexane | 186 |
| H | H | cyclohexane | 123–124 |
| CH$_3$-5 | H | cyclohexane | 164 |
| CH$_3$O-5 | H | cyclohexane | 226 |
| Cl-6 | H | cyclohexane | 168 |
| CF$_3$O-5 | H | cyclohexane | 164 |
| C$_6$H$_5$O-5 | H | cyclohexane | 160 |

Preparation 2:

The 1,3-dihydro-3-spirocyclohexaneindol-2-one described in Table 1 above can also be obtained by alkylation of the indol-2-one using the process according to A. S. Kende and J. C. Hodges or a variant described below.

A solution of 30 g of 1,3-dihydroindol-2-one in 900 ml of THF is kept at −40° C. under a nitrogen atmosphere and 101 g of potassium tert-butylate are added. The temperature is allowed to rise to 0° C. over 1 hour, the mixture is then cooled to −60° C. and a solution of 52 g of 1,5-dibromopentane in 50 ml of THF is added dropwise. After 30 minutes at −60° C., the temperature is allowed to rise to RT, 30 ml of water are then added and the solvent is evaporated off under reduced pressure. The residue is taken up with 500 ml of DCM and 200 ml of water, the insoluble material is then filtered off and the organic phase is separated off, washed with 100 ml of water, dried over magnesium sulfate and evaporated under vacuum. The residue is chromatographed on silica using a cyclohexane/ether mixture as the eluent to give the expected compound, which is recrystallized from heptane. m=34 g. M.p.=123°–124° C.

A similar procedure can be applied starting from other 1,3-dihydroindol-2-ones and other alkylating agents.

By way of example, among the starting compounds of formula (VII), 5-chloro-1,3-dihydroindol-2-one is described by Wright in J. Am. Chem. Soc., 1956, 78, 221, and by RajanBabu in J. Org. Chem., 1986, 51, 1704. 4-Chloro-1,3-dihydroindol-2-one can be prepared from 2-chloro-6-nitrotoluene by the method described in J. Am. Chem. Soc., 1956, 78, 221.

1,3-Dihydro-5-methoxyindol-2-one is prepared from 4-methoxyaniline by the method described in J. Am. Chem. Soc., 1974, 96, 5512. In the same way, various 1,3-dihydroindol-2-ones are prepared from the appropriate aniline derivative.

Preparation 3:

5-Ethoxy-1,3-dihydroindol-2-one

A—3-Methylthio-5-ethoxy-1,3-dihydroindol-2-one 23.6 g of ethyl methylthioacetate in 60 ml of DCM are added to a solution, cooled to about −70° C., of 12.5 g of chlorine in 400 ml of DCM. After stirring for 5 minutes at the same temperature, a solution of 4-ethoxyaniline (48.3 g) in 120 ml of DCM is added. The mixture is stirred for one hour at about −70° C., 39.3 ml of triethylamine are added and the resulting mixture is allowed to warm up to room temperature. 200 ml of water are added and the organic phase is decanted, dried over magnesium sulfate and evaporated under reduced pressure. The residue is taken up with 500 ml of isopropanol and 20 ml of concentrated hydrochloric acid. The mixture is stirred for about 16 hours at room temperature and filtered and the precipitate is separated off. The filtrate is concentrated under reduced pressure to give the expected product.

B—5-Ethoxy-1,3-dihydroindol-2-one

The above solid, in 1500 ml of isopropanol, is dethiomethylated in the presence of 100 g of Raney® nickel (80 to 100 m$^2$ per g), under reflux, for 3 hours, under a nitrogen atmosphere. The mixture is filtered on talc, the material on the filter is rinsed with 1000 ml of isopropanol and the filtrate is concentrated under reduced pressure. 16 g of the expected product are isolated after recrystallization from toluene. M.p.=156° C.

The following are isolated in the same manner starting from the corresponding anilines:

| | |
|---|---|
| 5-benzyloxy-1,3-dihydroindol-2-one | m.p. = 152° C. |
| 5-n-propyl-1,3-dihydroindol-2-one | m.p. = 136° C. |
| 5-ethyl-1,3-dihydroindol-2-one | m.p. = 152° C. |
| 5-(2,2,2-trifluoroethoxy)-1,3-dihydroindol-2-one | m.p. = 145° C. |
| 5-trifluoromethyl-1,3-dihydroindol-2-one | m.p. = 193° C. |
| 5-fluoro-1,3-dihydroindol-2-one | m.p. = 143° C. |

The compounds of formula (II) described below are obtained by following the technique described in Preparation 2 and varying the starting 1,3-dihydroindol-2-one derivative and the alkylating reagent.

TABLE 2

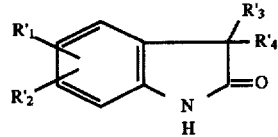
(II)

| R'$_1$ | R'$_2$ | CR'$_3$R'$_4$ | M.p. °C. | alkylating reagent |
|---|---|---|---|---|
| 5-Cl | H | cylohexane | 186–189 | Br(CH$_2$)$_5$Br |
| 5-Cl | H | cycloheptane | 202 | Br(CH$_2$)$_6$Br |
| 5-Cl | H | 4,4-dimethyl cyclohexane | 180 | TsO(CH$_2$)$_2$C(CH$_3$)$_2$—(CH$_2$)$_2$OTs |
| 5-Cl | H | 2-hexahydroindane | 223 | cis-1,2-diiodomethyl-cyclohexane |
| 5-OCH$_3$ | H | 4,4-dimethyl cyclohexane | 202 | TsO(CH$_2$)$_2$C(CH$_3$)$_2$—(CH$_2$)$_2$—OTs |
| 5-Cl | H | 2-indane | 228 | α,α'-dibromomethyl orthoxylene |
| 5-Cl | H | C(CH$_3$)$_2$ | 160 | CH$_3$I |
| 5-Cl | H | C(CH$_2$CH$_3$)$_2$ | 156 | CH$_3$CH$_2$I |
| 5-Cl | H | C(n Pr)$_2$ | 158 | nPrI |
| 5-Cl | H | C(iBu)$_2$ | 164 | iBuI |
| 5-Cl | H | N-methyl-4-piperidine | 260 | Cl(CH$_2$)$_2$N(CH$_3$)—(CH$_2$)$_2$Cl |
| 5-Cl | H | 4-tetrahydropyran | 223 | I(CH$_2$)$_2$O(CH$_2$)$_2$I |
| 4-Cl | H | cyclohexane | 215 | Br(CH$_2$)$_5$Br |
| 5-OBz | H | cyclohexane | 162 | Br(CH$_2$)$_5$Br |
| H | H | C(CH$_2$C$_6$H$_5$)$_2$ | 206 | C$_6$H$_5$CH$_2$Br |
| 5-Cl | H | C(n-pentyl)$_2$ | 142 | CH$_3$(CH$_2$)$_4$Br |
| 5-Cl | H | 2,3-dihydro phenalene-2 | — | 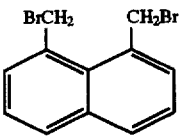 |
| 5-OBz | H | 4,4-dimethyl cyclohexane | 154 | TsO(CH$_2$)$_2$C(CH$_3$)$_2$—(CH$_2$)$_2$OTs |
| 5-Cl | H | 4-spirocyclopentane cyclohexane | 202 | 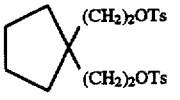 |
| 5-nPr | H | cyclohexane | 151 | Br(CH$_2$)$_5$Br |
| 5-OEt | H | N-tBu-4 piperidine | — | 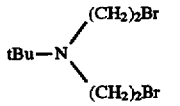 |
| 5-Cl | H | N—Bz-4 piperidine | 165 | 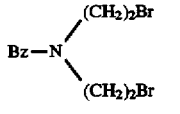 |
| 5-Cl | H | N-phenyl-4 piperidine | 188 | 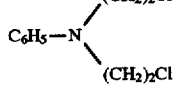 |
| 5-Cl | H | 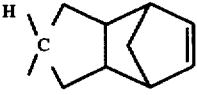 | 300 | 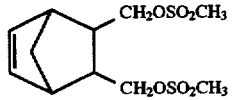 |
| 5-OEt | H | 4,4-diethyl cyclohexane | 132 | TsO(CH$_2$)$_2$C(C$_2$H$_5$)$_2$—(CH$_2$)$_2$OTs |
| 5-OEt | H | cyclohexane | 163 | Br(CH$_2$)$_5$Br |
| 5-OEt | H | 4,4-dimethyl cyclohexane | 178 | TsO(CH$_2$)$_2$C(CH$_3$)$_2$—(CH$_2$)$_2$OTs |
| 5-OEt | H | cycloheptane | 139 | Br(CH$_2$)$_6$Br |
| 5-Et | H | 4,4-dimethyl cyclohexane | 160 | TsO(CH$_2$)$_2$C(CH$_3$)$_2$—(CH$_2$)$_2$OTs |

TABLE 2-continued

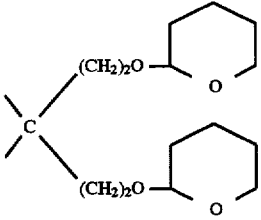 (II)

| R'₁ | R'₂ | CR'₃R'₄ | M.p. °C. | alkylating reagent |
|---|---|---|---|---|
| 5-OCH₂CF₃ | H | 4,4-dimethyl cyclohexane | 164 | idem |
| H | H | 4,4-dimethyl cyclohexane | 169 | idem |
| 5-CF₃ | H | 4,4-dimethyl cyclohexane | 211 | idem |
| 5-F | H | 4,4-dimethyl cyclohexane | 171 | idem |
| 5-Cl | H | 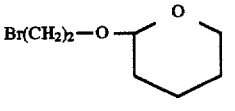 | 120 | Br(CH₂)₂—O—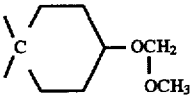 |
| 5-OEt | H | 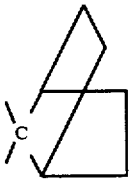 | NMR** | TsO(CH₂)₂—CH—(CH₂)₂OTs<br>                OCH₂OCH₃ |
| 5-OEt | H | 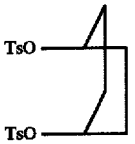 | 208 | 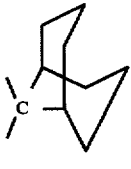 |
| 5-OEt | H | 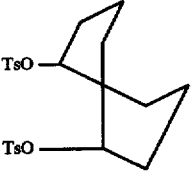 | 214 | 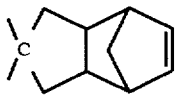 |
| 5-OEt | H | 4-tetrahydro-pyran | 146 | I(CH₂)₂O(CH₂)₂I |
| 5-OEt | H | 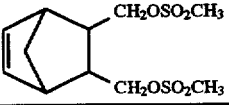 | 255 | CH₂OSO₂CH₃ / CH₂OSO₂CH₃ (on bicyclic alkene) |

**NMR spectrum at 200 MHz in CDCl₃:
8.3 ppm:s:1H
7.1 ppm:d:1H
6.7 ppm:m:2H
4.7 ppm:s:2H
3.9 ppm:q:2H
3.8 ppm:m:1H
3.4 ppm:s:3H
2.2 ppm:m:2H
1.8 ppm:m:6H
1.4 ppm:t:3H Preparation 4:

1,3-Dihydro-3-spiroadamantaneindol-2-one

This compound is prepared according to I. Fleming et al., Tetrahedron Letters, 1982, 2053–2056, starting from 2-bromoaniline and adamantan-2-one.

Preparation 5:

5-Chloro-1,3-dihydro-3,3-diphenylindol-2-one

This compound is prepared by the method described in Helv. Chim. Acta, 1946, 29, 415–431, by the reaction of benzene with 5-chloroisatin in the presence of aluminum chloride. M.p.=281° C.

Preparation 6:

1,3-Dihydro-5-nitro-3-spirocyclohexaneindol-2-one

This compound is prepared by the method described in J. Am. Chem. Soc., 1945, 67, 499, by the nitration of 1,3-dihydro-3-spirocyclohexaneindol-2-one. M.p.=192° C.

1,3-Dihydro-5-nitro-3-spiroadamantaneindol-2-one is prepared in the same manner starting from 1,3-dihydro-3-spiroadamantaneindol-2-one. M.p.>260° C.

1,3-Dihydro-5-nitro-3-spiro(4,4-dimethylcyclohexane)indol-2-one is also prepared. M.p.=195° C.

Preparation 7:

5-Amino-1,3-dihydro-3-spirocyclohexaneindol-2-one

This compound is prepared by the method described in J. Chem. Soc., 1951, 3475, by the reduction of 1,3-dihydro-5-nitro-3-spirocyclohexane indol-2-one, prepared above. M.p.=176° C.

5-Amino-1,3-dihydro-3-spiroadamantaneindol-2-one is prepared in the same manner. M.p.$_c$=245° C.

Preparation 8:

5-Fluoro-1,3-dihydro-3-spirocyclohexaneindol-2-one

A—5-Diazonium-i,3-dihydro-3-spirocyclohexaneindol-2-one tetrafluoroborate

A solution containing 4 g of 5-amino-1,3-dihydro-3-spirocyclohexaneindol-2-one in 9.2 ml of 6N hydrochloric acid is cooled to 0° C. and 2.27 g of sodium nitrite in 2.6 ml of water are added, followed by 2.54 g of sodium tetrafluoroborate in 9 ml of water. After stirring for 5 minutes, the precipitate is filtered off and washed with a 5% solution of tetrafluoroborate, with 3 ml of methanol cooled to about 0° C. and then with 5 ml of ether. The salt obtained is dried under vacuum at RT in the presence of phosphorus pentoxide.

B—5-Fluoro-1,3-dihydro-3-spirocyclohexeneindol-2-one.

1 g of the compound obtained in step A is placed in 5 ml of xylene and heated at about 115° C. for 2 hours. The mixture is cooled to RT, the precipitate is filtered off and rinsed with toluene and 0.1 g of active charcoal is added to the filtrate. After filtration, the solvent is evaporated off under reduced pressure to give 0.45 g of the expected compound, which is recrystallized from pentane. M.p.=114° C.

Preparation 9:

5-Cyano-1,3-dihydro-3-spirocyclohexaneindol-2-one 4.78 g of potassium cyanide and 4.95 g of cuprous cyanide are dissolved at RT in 40 ml of DMSO. The solution is cooled to about 15° C. and 4.15 g of the diazonium salt obtained in step A of the previous preparation are added.

After stirring for 30 minutes at RT, 100 ml of water and 100 ml of ether are added and the organic phase is then separated off, dried over magnesium sulfate and evaporated under reduced pressure. The residue is chromatographed on silica using a cyclohexane/ether mixture as the eluent to give the expected compound, which is recrystallized from heptane.

m=1.4 g. M.p.=216° C.

Preparation 10:

5-Chloro-1,3-dihydro-3-spiroadamantaneindol-2-one 1 g of the p-chlorophenylhydrazide of adamantane-2-carboxylic acid is dissolved in THF and 2.5 ml of a solution of n-butyllithium (1.6M in hexane) are added at −40° C. After stirring for 5 minutes, the mixture is concentrated under vacuum, the temperature being kept below 30° C. 30 ml of 1,2,3,4-tetramethylbenzene are added and the mixture is refluxed for 1 hour. It is concentrated under reduced pressure, the residue is taken up with normal hydrochloric acid, extraction is carried out with ether and the extract is washed, dried and concentrated under vacuum. The oil obtained is chromatographed on a silica column using DCM as the eluent to give 0.3 g of the expected product in the form of a wax, which is crystallized from iso ether. M.p.=249° C.

Preparation 11:

5-Chloro-3-cyclohexyl-1,3-dihydro-3-methylindol-2-one

The method described in Synth. Commun., 1982, 12 (1), 1–10, is used to prepare 5-chloro-3-cyclohexyl-1,3-dihydroindol-2-one as an intermediate, and the expected compound is then obtained by reaction with methyl iodide.

Preparation 12:

5-Acetyl-1,3-dihydro-3-spirocyclohexaneindol-2-one 2.56 g of acetyl chloride and than 8.25 g of anhydrous aluminum chloride are added to a solution, cooled to 5° C., of 4 g of 1,3-dihydro-3-spirocyclohexaneindol-2-one in 35 ml of 1,2-dichloroethane. The mixture is refluxed for 2 hours, the solvent is evaporated off under reduced pressure and the medium is hydrolyzed with 50 g of ice and extracted with ethyl acetate.

The organic phase is washed with water, dried over magnesium sulfate and than evaporated under reduced pressure. The residue is chromatographed on a silica column using a mixture of heptane and ethyl ether as the eluent to give 3.6 g of the expected product. M.p.=192° C.

Preparation 13:

5-Chloro-1,3-dihydro-3-spiro(tetrahydrothiopyran-4-yl)indol-2-one

A—5-Chloro-1,3-dihydro-3,3-di(2-bromoethyl)-indol-2-one 7.66 g of bromine are added slowly to a mixture, cooled to about 0° C., of 12.4 g of triphenylphosphine in 70 ml of DCM, and 4.58 g of 5-chloro-1,3-dihydro-3,3-di[2-(tetrahydropyran-2-yloxy)ethyl]indol-2-one, described in Table 2, are then added. After 16 hours at RT, 60 ml of water are added and the organic phase is separated off, washed with 60 ml of water and then dried over magnesium sulfate and evaporated under vacuum. The residue is chromatographed on a silica column using DCM as the eluent to give 3.12 g of the expected product. M.p.=215° C.

B—5-Chloro-1,3-dihydro-3-spiro(tetrahydro thiopyran-4-yl)indol-2-one

Under an inert atmosphere, 3 g of the product prepared in step A are added to 3.2 ml of DMF and 2 g of sodium sulfide monohydrate and the mixture is heated for 2 hours at 50° C. It is cooled to RT, 6 ml of water are added and the mixture is extracted with DCM. The organic phase is washed with water, dried over magnesium sulfate and evaporated under reduced pressure. The oily residue obtained is purified by chromatography on silica using DCM as the eluent to give 2.02 g of the expected compound.

NMR spectrum at 200 MHz in $CDCl_3$:

8.12 ppm: s: 1H
7.2 ppm: m: 2H
6.8 ppm: d: 1H
3.25 ppm: m: 2H
2.65 ppm: m: 2H 2 ppm: m: 4H Preparation 14:

5-Ethoxy-1,3-dihydro-3-spiro[4-(methoxymethoxy)-cyclohexane]indol-2-one

A—3-(Methoxymethoxy)pentane-1,5-diol 270 ml of a 1M solution of lithium aluminum hydride in THF, diluted in 540 ml of anhydrous THF, is cooled to 0° C. and a solution of 63 g of diethyl 3-(methoxymethoxy) glutarate (prepared according to J. L. Gras in Synthesis, 1985, 74) in 400 ml of THF is added. The mixture is stirred for 16 hours at RT and then cooled to 0° C. and 9 ml of water, 30 ml of a 15% solution of NaOH and 9 ml of water are added successively. The mineral salts are filtered off and the filtrate is evaporated under vacuum to give 24 g of the expected product after distillation under reduced pressure. B.p.=125° C. under 1.2 Pa.

B—3-(Methoxtnnethoxy)-1,5-ditosyloxypentane

A solution of 46 g of p-toluenesulfonyl chloride and 38 ml of triethylamine in 80 ml of THF is cooled to 0° C., a solution of 18 g of the compound obtained in the previous step in 100 ml of THF is added and the mixture is stirred for 16 hours at RT. 150 ml of water are added to the reaction mixture, the solvent is evaporated off under vacuum, the residue is extracted with AcOEt and the latter is evaporated off under vacuum. The oil obtained is taken up with 250 ml of ether and 200 ml of 2N NaOH and the mixture is stirred for 16 hours at RT. After decantation, the organic phase is dried over magnesium sulfate and the solvent is evaporated off under vacuum to give 45 g of the expected product after crystallization from cyclohexane. M.p.<50° C.

C—5-Ethoxy-1,3-dihydro-3-spiro[4-(methoxymethoxy)cyclohexane]indol-2-one

This compound is prepared by the procedure described in Preparation 2 starting from 5-ethoxy-1,3-dihydroindol-2-one and the compound obtained in the previous step. The expected product is obtained in the form of a mixture of isomers. M.p.=98° C.

Preparation 15:

5-Ethoxy-1,3-dihydro-3-spiro[4-tricyclo[5.2.1.0$^{2,6}$]decane]indol-2-one

A mixture of 3 g of 5-ethoxy-1,3-dihydro-3-spiro[4-tricyclo[5.2.1.0$^{2,6}$]dec-8-ene]indol-2-one, described in Table 2, and 1.5 g of 10% palladium-on-charcoal in 160 ml of MeOH is hydrogenated for 16 hours at 40° C. under a pressure of 20 bar. The catalyst is filtered off on Celite® and washed with MeOH and the filtrate is evaporated under vacuum to give 2.95 g of the expected product. M.p.=236° C.

Preparations 16 and 17:

5-Ethoxy-1,3-dihydro-3-spiro(4-methoxycyclohexane) indol-2-one, the less polar isomer and the more polar isomer A—3-Methoxypentane-1,5-diol 25 ml of methyl trifluoromethylsulfonate are added to a solution of 30 g of diethyl 3-hydroxyglutarate and S3 ml of 2,6-di-tert-butylpyridine in 500 ml of DCM and the mixture is refluxod for 6 hours. After cooling, 500 ml of a 0.5N solution of HCl are added, the organic phase is decanted and dried over magnesium sulfate and the solvent is evaporated off under vacuum. The residue obtained is taken up with 200 ml of anhydrous THF, the mixture is filtered and the filtrate is then cooled to −5° C. 160 ml of a 1M solution of lithium aluminum hydride in THF are then added slowly and the mixture is stirred for 18 hours, the temperature being allowed to rise to RT. The reaction mixture is cooled to 0° C. and 5.5 ml of water, 18 ml of a 15% solution of NaOH and 5.5 ml of water are added successively. The mineral salts are filtered off and the filtrate is evaporated under vacuum to give the expected product after distillation under reduced pressure. B.p.=104° C. under 1.5 Pa.

B—3-Methoxy-1,5-ditosyloxypentane

A solution of 31 g of p-toluenesulfonyl chloride and 26 ml of triethylamine in 120 ml of THF is cooled to 0° C., 10 g of the compound obtained in the previous step are added and the mixture is stirred for 24 hours at RT. 120 ml of water are added to the reaction mixture, the solvent is evaporated off under vacuum, the residue is extracted with AcOEt and dried over magnesium sulfate and the solvent is evaporated off under vacuum. The oil obtained is taken up with 200 ml of ether and 200 ml of 2N NaOH and the mixture is stirred for 16 hours at RT. After decantation, the organic phase is dried over magnesium sulfate and the solvent is evaporated off under vacuum to give 26 g of the expected product after crystallization from cyclohexane. M.p.=58° C.

C — 5-Ethoxy-1,3-dihydro-3-spiro(4-methoxycyclohexane)indol-2-one, the less polar isomer and the more polar isomer These compounds are prepared by the procedure described in Preparation 2 starting from 11.85 g of 5-ethoxy-1,3-dihydroindol-2-one, 34 g of potassium tert-butylate and 26 g of the compound obtained in the previous step. They are chromatographed on silica using a cyclohexane/AcOEt mixture (80/20; v/v) as the eluent. The two isomers are separated into the less polar isomer: compound of Preparation 16, m.p.=173° C.;

the more polar isomer: compound of Preparation 17, m.p.=186° C.

In addition, the benzenesulfonyl chlorides described in the Table below were prepared using the procedure described in the general section.

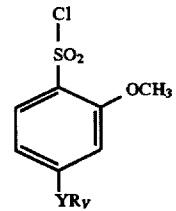

| Y | R$_V$ | M.p. °C. |
|---|---|---|
| S | CH$_3$ | 85 |
| O | CH$_2$Bz | 95 |
| O | CH$_2$CO$_2$Et | 89 |
| O | (CH$_2$)$_3$Br | 106–108 |

Starting from the various 1,3-dihydroindol-2-ones described above and appropriate benzenesulfonyl chlorides, the compounds according to the invention were prepared using the procedures reported in the Examples below.

EXAMPLE 1

5-Chloro-1,3-dihydro-1-(2-methoxy-4-nitrobenzenesulfonyl)-3-spirocyclohexaneindol-2-one A mixture containing 0.7 g of 5-chloro-1,3-dihydro-3-spirocyclohexaneindol-2-one and 70 mg of sodium hydride in 7 ml of THF is stirred under nitrogen at RT for 30 minutes. 0.7 g of 2-methoxy-4-nitrobenzenesulfonyl chloride is introduced and stirring is maintained at RT for 20 hours. The mixture is concentrated under vacuum, the residue is taken up in 30 ml of water, extraction is carried out with ethyl acetate and the extract is washed with water and then dried and concentrated to give 1.1 g of the expected compound, which crystallizes from iso ether.

M.p.=188° C.

EXAMPLE 2

1-(4-Amino-2-methoxybenzenesulfonyl)-5-chloro-1,3-dihydro-3-spirocyclohexaneindol-2-one 0.8 g of the compound obtained in the previous Example is reduced with hydrogen under normal pressure at RT for 20 hours in 10 ml of acetic acid, in the presence of 30 mg of platinum oxide. The reaction medium is filtered, the filtrate is concentrated, the residue is taken up in a water/ethyl acetate mixture and the organic phase is washed with water, dried and concentrated. The yellow foam obtained chromatographed on alumina using DCM as the eluent to give 0.2 g of the expected product.

M.p.=173° C.

EXAMPLE 3

5-Chloro-1,3-dihydro-1-[4-(2-methylphenylcarboxamido)-2-methoxybenzenesulfonyl]-3-spirocyclohexaneindol-2-one A mixture containing 0.2 g of the compound prepared in the previous Example, 0.5 ml of triethylamine, 5 ml of DCM and 0.1 g of orthotoluoyl chloride is stirred at RT for 48 hours. It is concentrated under vacuum, the residue is taken up in a water/ether mixture and left to decant and the organic phase is washed with a saturated solution of sodium hydrogen carbonate and then with water, dried and concentrated under vacuum to give 250 mg of a solid, which is chromatographed on silica using DCM as the eluent to give 0.1 g of the expected product.

M.p.=192° C.

EXAMPLE 4

6-Chloro-1,3-dihydro-1-(2,4-dimethoxybenzenesulfonyl)-3-spirocyclohexaneindol-2-one A mixture containing 0.15 g of 6-chloro-1,3-dihydro-3-spirocyclohexaneindol-2-one and 16 mg of Sodium hydride in 2 ml of THF is stirred for 30 minutes at RT under nitrogen; 0.15 g of 2,4-dimethoxybenzenesulfonyl chloride is introduced and stirring is maintained at RT for 20 hours at 20° C. The mixture is concentrated under vacuum, the residue is taken up in 30 ml of water and extracted with ethyl acetate and the extract is washed with water, dried and concentrated under vacuum. The product obtained is recrystallized from iso ether.

M.p.=147° C.

EXAMPLE 5

Acid fumarate of 5-chloro-1,3-dihydro-1-[4-(3-dimethylaminopropoxy)benzenesulfonyl]-3-spirocyclohexaneindol-2-one A) 4-(3-Bromopropoxy)benzenesulfonyl chloride A mixture containing 23 g of sodium 4-hydroxybenzenesulfonate dihydrate, 7 g of potassium hydroxide pellets (85%), 30 ml of water, 50 ml of absolute ethanol, 40 g of 1,3-dibromopropane and 3.4 g of tetrabutylammonium hydrogen sulfate is refluxed for 3 hours. The reaction medium is concentrated under vacuum, taken up in ethanol and concentrated once again. The residue is taken up in hot methanol. The insoluble material is filtered off, the filtrate is concentrated and the residue is triturated in ether to give 22.5 g of a white solid. 120 ml of phosphorus oxychloride and 16 g of phosphorus pentachloride are added to this solid and the mixture is stirred for 20 hours at RT and then refluxed for 1 hour. The reaction medium is taken up in an ether/water mixture and the organic phase is decanted and washed with a saturated solution of sodium hydrogen carbonate. After drying and concentration, the expected product is obtained in the form of a yellow oil.

B) 1-[4-(3-Bromopropoxy)benzenesulfonyl]-5-chloro-3-spirocyclohexaneindol-2-one

A mixture containing 1.2 g of 5-chloro-3-spirocyclohexaneindol-2-one and 0.16 g of sodium hydride in 6 ml of THF is stirred at RT for 30 minutes under nitrogen. 1.6 g of 4-(3-bromopropoxy)benzenesulfonyl chloride are then added.

After 20 hours at RT, the reaction medium is concentrated under vacuum, the residue is taken up in a water/ethyl ether mixture and decanted and the organic phase is washed with water, dried and concentrated. The oil obtained is purified by chromatography on silica using iso ether as the eluent. The expected product is obtained in the form of an oil, which crystallizes from iso ether.

m=1 g.

M.p.=123° C.

C) Acid fumarate of 5-chloro-1,3-dihydro-1-[4-(3-dimethylaminopropoxy)phenylsulfonyl]-3-spirocyclohexaneindol-2-one A mixture containing 0.5 g of the product obtained in the above step, 0.5 g of potassium iodide and 20 ml of a 33% solution of dimethylamine in methanol is stirred at RT for 20 hours. The reaction medium is concentrated and taken up in 10 ml of water and, after trituration, the insoluble material is separated off and treated with 10 ml of 3N hydrochloric acid. A gum is formed which is dissolved in 30 ml of warm water, and the solution is filtered on paper and then rendered alkaline by the addition of 12N sodium hydroxide. The insoluble material is extracted with ether and the extract is washed, dried and then concentrated to give a yellow oil. This is dissolved in 10 ml of acetone, and 0.1 g of fumaric acid is added to the hot solution.

The expected product precipitates at 20° C.

m=240 mg.

M.p.=168° C.

EXAMPLE 6

5-Chloro-1,3-dihydro-1-(2,4-dimethoxyphenylsulfonyl)-3-spiroadamantaneindol-2-one A mixture containing 0.2 g of 5-chloro-3-spiro adamantaneindol-2-one and 20 mg of sodium hydride in 3 ml of THF is stirred for 30 minutes at RT under a nitrogen atmosphere. 0.18 g of 2,4-dimethoxybenzenesulfonyl chloride is added and stirring is maintained at RT for 20 hours. The reaction medium is concentrated under vacuum, the residue is taken up in 30 ml of water and extracted with ether and the extract is washed with water, dried and concentrated under vacuum. The wax obtained crystallizes from 15 ml of iso ether.

m=240 mg.

M.p.=152°–154° C.

EXAMPLE 7

5-Chloro-1,3-dihydro-1-(2,4-dimethoxybenzenesulfonyl)-3-spirocycloheptaneindol-2-one A solution containing 0.156 g of potassium tert-butylate and 0.33 g of 5-chloro-1,3-dihydro-3-spirocycloheptaneindol-2-one in 15 ml of THF is cooled to −40° C. under an inert atmosphere. The temperature is allowed to rise to about 10° C. over 1 hour, the solution is then cooled to about −40° C., a solution of 0.335 g of 2,4-dimethoxybenzenesulfonyl chloride in 15 ml of THF is added dropwise and the mixture is stirred at RT for 2 hours. The solvent is evaporated off under reduced pressure and the residue is then taken up in 30 ml of DCM and 30 ml of water. The organic phase is separated off, washed with 15 ml of water, dried over magnesium sulfate and evaporated under vacuum. The oil obtained is chromatographed on silica using a cyclohexane/DCM mixture as the eluent to give the expected compound, which recrystallizes from heptane.

m=0.51 g.
M.p.=135° C.

EXAMPLE 8

2,4-Dimethoxy-1,3-dihydro-1-benzenesulfonyl-2a-methyl-2a,3,4,5-tetrahydrobenz[c,d]indol-2-one (I: $R_1=R_4=H$, $-R_2-R_3=-(CH_2)_3$, $R_5=R_6=OCH_3$)

2a,3,4,5-Tetrahydrobenz[c,d]indol-2-one is commercially available. With the temperature maintained at −40° C. and under a nitrogen atmosphere, a solution containing 0.7 g of this compound and 1.36 g of potassium tert-butylate in 40 ml of anhydrous THF is prepared. The temperature is allowed to rise to about 0° C., the solution is then cooled to −60° C. and a solution of 0.57 g of methyl iodide in 20 ml of THF is added; the medium is maintained at −10° C. for 30 minutes, with stirring, and then cooled to about −40° C. and a solution of 0.96 g of 2,4-dimethoxybenzenesulfonyl chloride in 10 ml of THF is added. After stirring for 16 hours at RT, the solvent is evaporated off under reduced pressure and the residue is taken up in 30 ml of DCM and 30 ml of water; the organic phase is separated off and then dried over magnesium sulfate and evaporated. The oil obtained is purified by chromatography on silica using a cyclohexane/DCM mixture as the eluent to give the expected product, which is recrystallized from a cyclohexane/AcOEt mixture (95/5; v/v).

M.p.=160° C.

The compounds according to the invention collated in Table 3 below were prepared from the 1,3-dihydro-indol-2-ones described above by following the procedure described in the above Examples.

TABLE 3

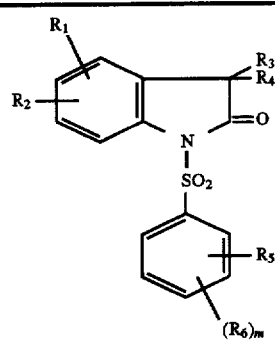

Unless indicated otherwise in the Table below (*), $R_2=H$ and m=1.

| Ex. | $R_1$ | $CR_3R_4$ | $R_5$ | $(R_6)$ m | M.p. °C. |
|---|---|---|---|---|---|
| 9 | 5-Cl | $C(C_6H_5)_2$ | 3-MeO | 4-MeO | 178 |
| 10 | 5-NO$_2$ | cyclohexane | 3-MeO | 4-MeO | 157 |
| 11 | 5-Cl | cyclohexane | 4-MeO | H | 112 |
| 12 | 5-Cl | $C(CH_3)_2$ | 3-MeO | 4-MeO | 110 |
| 13 | 5-NH$_2$ | cyclohexane | 3-MeO | 4-MeO | 171 |
| 14 | 5-CN | cyclohexane | 2-MeO | 4-MeO | 148 |
| 15 | 5-Cl | cyclohexane | 4-MeO | 2,3,6-triMe | 188 |
| 16 | 5-Cl | $C(Pr)_2$ | 2-MeO | 4-MeO | 186 |
| 17 | 5-Cl | indane-2 | 2-MeO | 4-MeO | 182 |
| 18 | 5-Cl | $C(iBu)_2$ | 2-MeO | 4-MeO | 184 |
| 19 | 5-Cl | N-methyl-4-piperidine | 2-MeO | 4-MeO | 142 |
| 20 | 5-Cl | $C(Et)_2$ | 2-MeO | 4-MeO | 190 |
| 21 | 5-F | cyclohexane | 2-MeO | 4-MeO | 149 |
| 22 | 5-Cl | 4-tetrahydropyran | 2-MeO | 4-MeO | 142 |
| 23 | 5-Cl | 4,4-dimethyl cyclohexane | 2-MeO | 4-MeO | 118 |
| 24 | 5-Cl | 2-hexahydro-indane | 2-MeO | 4-MeO | 89 |
| 25 | 4-Cl | cyclohexane | 2-MeO | 4-MeO | 150 |
| 26 | 5-Cl | cyclohexane | 3-MeO | 4-MeO | 152 |
| 27 | 5-Cl | cyclohexane | 4-Me | H | 150 |
| 28 | H | cyclohexane | 3-MeO | 4-MeO | 107 |
| 29 | 5-Me | cyclohexane | 3-MeO | 4-MeO | 171 |
| 30 | 5-MeO | cyclohexane | 3-MeO | 4-MeO | 124 |
| 31 | 5-Cl | cyclohexane | 2-MeO | 4-MeO | 149 |
| 32 | 5-Cl | cyclohexane | 4-Cl | H | 154 |
| 33 | 5-Cl | cyclobutane | 3-MeO | 4-MeO | 111 |
| 34 | 5-Cl | cyclopentane | 3-MeO | 4-MeO | 106 |
| 35 | 5-Cl | cyclohexane | 4-MeO | 2-Cl | 174 |
| 36 | 5-Cl | cyclohexane | 4-NO$_2$ | H | 172 |
| 37 | 5-Cl | cyclohexane | 4-CN | H | 198 |
| 38 | 5-Cl | cyclohexane | 4-MeO | 2-NO$_2$ | 147 |
| 39 | 5-Cl | cyclohexane | 4-CF$_3$ | H | 139 |
| 40 | 5-Cl | cyclohexane | 4-CF$_3$O | H | 134 |
| 41 | 5-Cl | cyclohexane | 4-MeO | 2-NH$_2$ | 150 |
| 42 | 4-CH$_3$ | cyclohexane | 4-MeO | 2-MeO | 165 |
| *43 | $R_2=6$-CH$_3$ 5-Cl | cyclohexane | 3-Me | 4-BzO | 127 |
| 44 | 5-Cl | cyclohexane | 4-iPr | 2,6-iPr | 172 |
| 45 | 5-Cl | cyclohexane | 2-CF$_3$ | H | 154 |

-continued

| Ex. | R₁ | CR₃R₄ | R₅ | (R₆) m | M.p. °C. |
|---|---|---|---|---|---|
| 46 | 5-Cl | cyclohexane | 2-MeO | 3,4-(CH₃)₂-phenyl-CO—NH₄ | 215 |
| 47 | 5-Cl | cyclohexane | 4-MeO | 2-CH₃-phenyl-CO—NH₄ | 193 |
| 48 | 5-Cl | cyclohexane | 2-MeO | 4-CH₃OCO | 120 |
| 49 | 5-Cl | 1-methylcyclohexane | 2-MeO | 4-MeO | 184 |
| 50 | H | adamantane | 2-MeO | 4-MeO | 172 |
| 51 | 5-MeO | 4,4-dimethyl cyclohexane | 2-MeO | 4-MeO | 152 |
| 52 | 5-Cl | cyclohexane | 2-MeO | 4-CH₃SO₂NH | 131 |
| 53 | 5-Cl | cyclohexane | 2-MeO | 3,5-diCl-phenyl-CONH-4 | 240 |
| 54 | 5-Cl | cyclohexane | 2-Me | 5-F | 153 |
| 55 | 5-Cl | cyclohexane | 2-CF₃—CH₂O | 5-CF₃CH₂O | 175 |
| 56 | 5-Cl | cyclohexane | 2-MeO | 2-CH₃-phenyl-NHCO-4 | 218 |
| 57 | 5-Cl | cyclohexane | 2-MeO | phenyl-O—CO-4 | 165 |
| 58 | 5-Cl | cyclohexane | 5-NH₂—SO₂ | 2,4-diMeO | 270 |
| 59 | 5-BzO | cyclohexane | 2-MeO | 4-MeO | 159 |
| 60 | 5-BzO | 4,4-dimethyl-cyclohexane | 2-MeO | 4-MeO | 142 |
| 61 | 5-Cl | cyclohexane | 2-MeO | 4-CH₃O-phenyl-C(O)—NH-4 | 192 |
| 62 | 5-Cl | cyclohexane | 2-MeO | 4-(CH₃N-piperazinyl)-C(O)-4 | 158 |
| 64 | H | C(CH₂C₆H₅)₂ | 3-MeO | 4-MeO | 146 |
| 65 | 5-CH₃CO | cyclohexane | 3-MeO | 4-MeO | 122 |
| 66 | 5-Cl | C(n-pentyl)₂ | 2-MeO | 4-MeO | 140 |
| 67 | 5-Cl | C(CH₂C₆H₅)₂ | 2-MeO | 4-MeO | 185 |
| 68 | 5-H₂N | cyclohexane | 2-MeO | 4-MeO | 230 |
| 69 | 5-Cl | 4-spirocyclo-pentane | 2-MeO | 4-MeO | 154 |
| 70 | 5-Cl | cyclohexane | 2-MeO | 5-MeO | 116 |
| 71 | 5-nPr | cyclohexane | 2-MeO | 4-MeO | 138 |
| 72 | 5-EtO | N-tBu-4-piperidine | 2-MeO | 4-MeO | 95 (0.25 |

-continued

| Ex. | R₁ | CR₃R₄ | R₅ | (R₆) m | M.p. °C. |
|---|---|---|---|---|---|
| 73 | 5-Cl | N-Bz-4-piperidine | 2-MeO | 4-MeO | 76 (0.5 H₂O) |
| 74 | 5-Cl | N-phenyl-4-piperidine | 2-MeO | 4-MeO | 163 |
| 75 | 5-Cl | cyclohexane | 2-EtO | 4-EtO | 123 |
| 76 | 5-Cl | 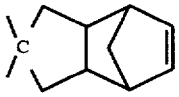 | 2-MeO | 4-MeO | 190 |
| 77 | 5-EtO | 4,4-diethyl-cyclohexane | 2-MeO | 4-MeO | 129 |
| 78 | 5-EtO | cycloheptane | 2-MeO | 4-MeO | 130 |
| 79 | 5-EtO | cyclohexane | 2-MeO | 4-MeO | 134 |
| 80 | 5-EtO | 4,4-dimethyl-cyclohexane | 2-MeO | 4-MeO | 160 |
| 81 | 5-Et | 4,4-dimethyl-cyclohexane | 2-MeO | 4-MeO | 166 |
| 82 | 5-EtO | 4,4-dimethyl-cyclohexane | 2-MeO | 4-NO₂ | 110 |
| 83 | 5-EtO | 4,4-dimethyl-cyclohexane | 2-MeO | 4-NH₂ | 230 |
| 84 | 5-NO₂ | 4,4-dimethyl-cyclohexane | 2-MeO | 4-MeO | 102 |
| 85 | 5-NH₂ | 4,4-dimethyl-cyclohexane | 2-MeO | 4-MeO | 180 |
| 86 | 5-CF₃CH₂O | 4,4-dimethyl-cyclohexane | 2-MeO | 4-MeO | 169 |

EXAMPLE 87

1-(2,4-Dimethoxybenzenesulfonyl)-3-(4,4-dimethylspirocyclohexane)-5-hydroxy-1,3-dihydro-indol-2-one 3.51 g of the compound obtained in Example 60 are stirred at 50° C. for 1 hour under hydrogen pressure, with 0.5 g of 10% palladium charcoal in 150 ml of ethanol. The catalyst is filtered off on talc, washed with DCM and the filtrate is evaporated under reduced pressure to give 2.8 g of the expected compound, which is recrystallized from a mixture of cyclohexane-AcOEt (90/10, v/v).

M.p.=220° C.

EXAMPLE 88

1-(2,4-dimethoxybenzenesulfonyl)-5-hydroxy-1,3-dihydro-3-spirocyclohexane-indol-2-one is prepared in the same manner starting from the 5-benzyloxy derivative disclosed in Example 59.

M.p.=196° C.

EXAMPLE 80 bis 1-(2,4-Dimethoxybenzenesulfonyl)-3-(4,4-dimethylspirocyclohexane)-5-ethoxy-1,3-dihydro-indol-2-one This compound, already disclosed in Example 80, may be prepared according to another method starting from the homologous 5-hydroxy compound. 0.6 g of the compound prepared in Example 87 is stirred at RT for 16 hours, under an inert atmosphere, with 0.19 g of anhydrous potassium carbonate and 0.315 g of ethyl iodide in 11 ml of DMF. The solvent is evaporated off under reduced pressure and 30 ml of AcOEt and 30 ml of water are added. The organic phase is washed with water, dried over magnesium sulfate, then concentrated under reduced pressure.

0.45 g of the expected compound is obtained by crystallization from cyclohexane.

M.p.=160° C.

The compounds disclosed in Table 4 below are prepared in the same manner.

TABLE 4

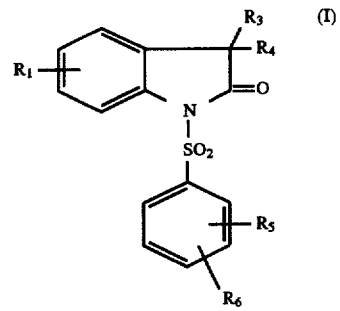

| Ex. | R₁ | CR₃R₄ | R₅ | R₆ | M.p. °C. |
|---|---|---|---|---|---|
| 89 | 5-nPrO | cyclohexane | 2-MeO | 4-MeO | 139 |
| 90 | 5-nPrO | 4,4-dimethyl-cyclohexane | 2-MeO | 4-MeO | 158 |
| 91 | 5-iPrO | 4,4-dimethyl-cyclohexane | 2-MeO | 4-MeO | 154 |
| 92 | 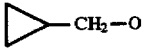 | cyclohexane | 2-MeO | 4-MeO | 155 |

EXAMPLE 93

5-Acetoxy-1,3-dihydro-1-(2,4-dimethoxybenzenesulfonyl)-3-spiro-cyclohexaneindol-2-one 0.5 g of the compound prepared in Example 88, 2.5 ml of isopropenyl acetate and 0.165 g of potassium carbonate in 2.5 ml of toluene and 0.3 ml of DMF are heated at about 65° C. for 15 hours. After cooling, 10 ml of water and 15 ml of ethyl acetate are added. The mixture is left to decant and the organic phase is washed with water, dried over magnesium sulfate and concentrated under reduced pressure. The gives 0.51 g of the expected product, containing 0.5 mole of cyclohexane, is isolated by crystallization from a cyclohexane/ethyl acetate M.p.=116° C.

EXAMPLE 94

1-(2,4-Dimethoxybenzenesulfonyl)-5-(2-hydroxyethoxy)-1,3-dihydro-3-spirooyclohexaneindol-2-one 0.5 g of the compound prepared in Example 88, 0.5 g of ethylene carbonate and 0.272 g of anhydrous potassium carbonate in 1.25 ml of DMF are heated at 70° C. for 40 hours. After cooling, 10 ml of water and 15 ml of ethyl acetate are added, the mixture is left to decant and the organic phase is washed with water, dried over magnesium sulfate and concentrated under reduced pressure. The oily residue is chromatographed on silica using a mixture of cyclohexane-AcOEt (70/30-v/v) as eluent, to give 0.5 g of the expected product, which is recrystallized from a heptane/DCM mixture.

M.p.=170° C.

EXAMPLE 95

5-(2-Dimethylaminoethoxy)-1,3-dihydro-1-(2,4-dimethoxy-benzenesulfonyl)-3-spirocyclohexaneindol-2-one 0.6 g of the compound prepared in Example 88 is heated around 40° C. for 16 hours, under an inert atmosphere, with 0.32 g of N,N-dimethyl-(2-chloroethylamine) and 1.76 g of cesium carbonate in 7.2 ml of acetone and 2.4 ml of DMF. The salts are filtered off and 20 ml of water and 20 ml of AcOEt are added to the filtrate.

The organic phase is decanted, washed with water, dried over magnesium sulfate and concentrated under reduced pressure. The residue is chromatographed on silica with a mixture of DCM-MeOH (9/1, v/v) as eluent to give 0.6 g of the expected product which is recrystallized from a cyclohexane/iso ether mixture.

M.p.=122° C.

EXAMPLE 96

5-Chloro-1,3-dihydro-1-(2,4-dimethoxybenzenesulfonyl)-3-(spiropiperidine-4)indol-2-one This reaction is carried out according to J. Org. Chem., 1984, 49, 2795-2799. 0.75 g of 1-chloroethyl chloroformate is added at 0° C. to a solution of 1.31 g of the compound disclosed in Example 73 and of 0.32 g of 1,8-bis-dimethylaminonaphthalene in 22 ml of 1,2-dichloroethane. The mixture is refluxed for about 20 minutes and concentrated under reduced pressure to a volume of about 10 ml, and 22 ml of methanol are then added. After refluxing for 50 minutes, the reaction mixture is concentrated under reduced pressure and the residue is chromatographed on a silica column using a mixture of DCM-MeOH (95/5, v/v) as eluent. 1.16 g of the expected product is obtained, which is recrystallized from a mixture of cyclohexane and ethyl acetate.

M.p.=172° C.

EXAMPLE 97

3-(N-Acetylspiropiperidine-4)-5-chloro-1,3-dihydro-1-(2,4-dimethoxybenzenesulfonyl)indol-2-one 0.086 ml of acetyl chloride are added to a solution, cooled to around 0° C., of 0.35 g of the compound prepared in the previous Example and 0.23 ml of triethylamine in 5 ml of DCM. The mixture is stirred for one hour at 20° C., 5 ml of water are added, the organic phase is decanted washed with water, dried over magnesium sulfate and concentrated under reduced pressure and the residue is chromatographed on a silica column using DCM/MeOH mixture (99/1, v/v) as the eluent. 0.29 g of the expected product is isolated in the form of the hemihydrate.

M.p.=107° C.

EXAMPLE 98

5-Chloro-1,3-dihydro-1-(2,4-dimethoxybenzenesulfonyl)-3-(N-methoxy-carbonylspiropiperidine-4)indol-2-one This compound is prepared from the compound obtained in Example 96 by reaction with methyl chloroformate.

M.p.=147° C.

EXAMPLE 99

1-(3,4-dimethoxybenzenesulfonyl)-5-propionamido-1,3-dihydro-3-spiro-cyclohexaneindol-2-one A solution of 0.144 g of propionyl chloride in 3 ml of DCM is added to a solution, cooled to about 0° C., of 0.5 g of the compound disclosed in Example 13 and 0.167 ml of triethylamine in 10 ml of DCM. The mixture is stirred for 2 hours at 20° C., 20 ml of water are then added and the organic phase is decanted, washed with water, dried over magnesium sulfate and concentrated under reduced pressure. 0.5 g of the expected product is isolated after recrystallization from a heptane/AcOEt mixture (95/5, v/v).

M.p.=158° C.

EXAMPLE 100

1-(3,4-dimethoxybenzenesulfonyl)-5-(N-methylureido)-1,3-dihydro-3-spirocyclohexaneindol-2-one 0.15 g of methyl isocyanate is added to a solution, cooled to about 0° C., of 0.5 g of the compound described in Example 13, in 10 ml of DCM. After stirring for about 16 hours at RT, 20 ml of water are added and the organic phase is decanted, washed with water, dried over magnesium sulfate and concentrated under reduced pressure. 0.5 g of the expected product is isolated after recrystallisation from a mixture of heptane and ethylacetate.

M.p.=214° C.

The compound disclosed in the following Example is prepared in the same manner.

EXAMPLE 101

1-(3,4-Dimethoxybenzenesulfonyl)-5-(N-phenylureido)1,3-dihydro-3-spirocyclohexaneindol-2-one M.p.=124° C.

EXAMPLE 102

5-Dimethylamino-1,3-dihydro-1-(2,4-dimethoxybenzenesulfonyl)-3-spirocyclohexaneindol-2-one A mixture of 0.5 g of the compound disclosed in Example 68 with 0.5 ml of a 35% solution of formaldehyde and 0.12 g of sodium cyanoborohydride in 10 ml of acetonitrile is stirred at RT, under a nitrogen atmosphere, and the pH is adjusted to around 6.5 with a few drops of acetic acid. After 48 hours at 20° C., the solvent is evaporated off under reduced pressure and 20 ml of a 2N aqueous solution of sodium hydroxide and 20 ml of DCM are added. The organic phase is decanted, washed with water and dried over magnesium sulfate and the solvent is evaporated off under reduced pressure. The residue is chromatographed on a silica column using a cyclohexane/ethyl acetate mixture (80/20, v/v) as the eluent. 0.27 g of the expected product is isolated.

M.p.=167° C.

EXAMPLE 103

1-(2,4-Dimethoxybenzenesulfonyl)-5-ethylthio-1,3-dihydro-3-spirocyclohexaneindol-2-one This compound is prepared according to J. Chem. Soc., Chem. Commun., 1980, 16, 756. A mixture of 2.95 g of diethyl disulfide and 0.386 g of isopentyl nitrite is heated to about 80° C. under an inert atmosphere, and 0.8 g of the compound prepared in Example 68 is added. The medium is stirred for one hour at 80° C. and then concentrated under reduced pressure. The residue is chromatographed on a silica column using DCM/cyclohexane mixture (80/20, v/v) as the eluent. The expected product is isolated after crystallization from cyclohexane.

M.p.=123° C.

EXAMPLE 104

5-Chloro-1,3-dihydro-1-[4-(dimethylaminomethylcarboxamido)-2-methoxybenzenesulfonyl]-3-spirocyclohexaneindol-2-one A) 5-Chloro-1,3-dihydro-1-[4-(chloromethylcarboxamido)-2-methoxybenzenesulfonyl]-3-spirocyclohexaneindol-2-one 0.2 g of the compound prepared in Example 2 is placed in 4 ml of DCM and 0.5 g of TEA at RT and 0.1 g of chloroacetyl chloride is added. After stirring for 20 hours at RT, the mixture is concentrated under vacuum. The concentrate is extracted with ethyl acetate, the extract is washed with water and a solution of sodium carbonate and the residue is then chromatographed on silica using a mixture of DCM and AcOEt as the eluent to give 0.15 of the expected product.

B) 5-Chloro-1,3-dihydro-1-([4-(dimethylaminomethylcarboxamido)-2-methoxybenzenesulfonyl]-3-spirocyclohexaneindol-2-one The compound obtained in the previous step (150 mg) is stirred at RT for 20 hours in 20 ml of a 33% solution of dimethylamine in ethanol. Extraction is carried out with AcOEt and the extract is washed with N sodium hydroxide, and then water. The residue is chromatographed on silica using AcOEt as the eluent to give 0.025 g of the expected product.

M.p.=173° C.

EXAMPLE 105

1-[4-(4-Sulfamoylphenylcarboxamido)-2-methoxybenzenesulfonyl]-5-chloro-1,3-dihydro-3-spirocyclohexaneindol-2-one 4-chlorosulfonylbenzoyl chloride is prepared according to Chem. Ber., 1941, 271.

0.2 g of the compound prepared in Example 2 is mixed with 0.5 g of TEA in 5 ml of DCM. 0.13 g of 4-chlorosulfonylbenzoyl chloride is added and the mixture is stirred for 20 hours at RT. It is concentrated under vacuum, the concentrate is taken up with THF, and 10 ml of aqueous ammonia are added. Stirring is continued for a further 20 hours at RT and the mixture is concentrated under vacuum. The residue is extracted with ether and the extract is washed with water, dried over sodium sulfate and then chromatographed on silica using AcOEt as the eluent to give the expected product.

M.p.=238°–242° C. after recrystallization from AcOEt.

EXAMPLE 106

1-[4-(3-Sulfamoylphenylcarboxamido)-2-methoxybenzenesulfonyl]-5-chloro-1,3-dihydro-3-spirocyclohexaneindol-2-one A) 3-chlorosulfonylbenzoyl chloride This compound is prepared according to patent U.S. Pat. No. 3,290,370. 11 g of chlorosulfonic acid are heated to 60° C. and 8 g of phenylchloroform are added dropwise. After heating for 2 hours at 130° C., the mixture is distilled to give 1 g of the expected product.

B.p.=120°–125° C. under 0.5 mmHg.

B) 1-4-(3-Sulfamoylphenylcarboxamido)-2-methoxybenzenesulfonyl]-5-chloro-1,3-dihydro-3-spirocyclohexaneindol-2-one 210 mg of the compound prepared in Example 2 are placed in 10 ml of DCM with 220 mg of the compound obtained in the previous step and 200 mg of TEA, the mixture is stirred overnight and the solvents are then evaporated off under vacuum. The residue is taken up with 20 ml of THF and 20 ml of aqueous ammonia. The mixture is stirred for 6 hours at RT. The solvents are evaporated off under vacuum and the residue is then taken up with AcOEt and water. Extraction is carried out with AcOEt and the extract is washed with water and then chromatographed on silica using an AcOEt/cyclohexane (50/50, v/v) as the eluent to give the expected product.

M.p.=176° C.

EXAMPLE 107

1-[4-(2-carboxyphenylcarboxamido)-2-methoxybenzenesulfonyl]-5-chloro-1,3-dihydro-3-spirocyclohexaneindol-2-one The preparation is carried out according to J. Heterocycl. Chem., 1974, 997–1000.

A mixture containing 0.2 g of the compound prepared in Example 2 with 0.5 ml of TEA and 160 mg of phthalic anhydride is stirred at 60° C. for 3 hours. The mixture is concentrated under vacuum and treated with normal hydrochloric acid. The precipitate formed is filtered off and treated with a 10% solution of sodium carbonate; a precipitate forms again the aqueous phase is decanted and the precipitate is treated with 10% AcOH. The precipitate is filtered off and then washed with 10% AcOH, followed by isopropyl ether and recrystallized from iso ether to give the expected product.

m=0.150 g
M.p.=157°–158° C.

EXAMPLE 108

1-[4-(Benzyloxymethylcarboxamido)-2-methoxybenzenesulfonyl]-5-chloro-1,3-dihydro-3-spirocyclohexaneindol-2-one This compound is prepared by the procedure described in Example 3 by reacting benzyloxyacetyl chloride with the compound prepared in Example 2.

M.p.=143° C. after recrystallization from iso ether.

EXAMPLE 109

5-Chloro-1,3-dihydro-1-[4-(hydroxymethylcarboxamido)-2-methoxybenzenesulfonyl]-3-spirocyclohexaneindol-2-one This compound is obtained by hydrogenating the compound prepared in the previous Example, under the pressure of a water column, in the presence of 5% palladium-on-charcoal in an EtOH/AcOEt mixture.

M.p.=202° C.

EXAMPLE 110

5-Chloro-1,3-dihydro-1-[4-(imidazol-1-ylphenylcarboxamido)-2-methoxybenzenesulfonyl]-3-spirocyclopentaneindol-2-one A) Ethyl 4-(imidazol-1-yl)benzoate A mixture containing 35 g of 4-fluorobenzoyl chloride in 50 ml of 100% ethanol is refluxed for 1.5 minutes. 35 g of the ethyl 4-fluorobenzoate obtained are mixed with 22 g of imidazole and 61 g of potassium carbonate in 35 ml of DMSO. The mixture is heated for 18 hours at 120°–130° C. and 500 ml of iced water are then added. A precipitate forms and the expected product crystallizes from iso ether.

M.p.=98° C.

B) (imidazol-1-yl)benzoyl chloride 5 g of the ester obtained in step A are refluxed for 2 hours in 20 ml of water and 20 ml of sodium hydroxide solution. The reaction medium is washed with ether and then acidified (pH 2) with concentrated hydrochloric acid. The precipitate formed is filtered off and then washed with ether. 5 g of the acid obtained are brought to the reflux temperature in 35 ml of thionyl chloride. The precipitate formed is filtered off and then washed with iso ether to give the expected acid chloride.

M.p.=243° C.

C) 5-Chloro-1,3-dihydro-1-[4-(imidazol-1-ylphenylcarboxamido)-2-methoxybenzenesulfonyl]-3-spirocyclopentaneindol-2-one A mixture containing 210 mg of the compound prepared in Example 2 and 200 mg of the acid chloride prepared in step B in 10 ml of DCM and 1.5 ml of TEA, is stirred at RT and then refluxed for 3 hours. The reaction medium is extracted with DCM and then washed with water and an aqueous solution of sodium hydroxide. After evaporation of the solvents, the residue is chromatographed on silica using a DCM/methanol mixture as the eluent. The expected product is recrystallized from iso ether.

m=0.010 g
M.p.=145° C.

EXAMPLE 111

5-Chloro-1,3-dihydro-1-[2-methoxy-4-(phenoxycarboxamido)benzenesulfonyl]-3-spirocyclohexaneindol-2-one This compound is prepared by reacting phenyl chloroformate with the compound prepared in Example 2.

M.p.=209° C. after recrystallization from iso ether.

EXAMPLE 112

5-Chloro-1,3-dihydro-1-[4-(N-methylureido)-2-methoxybenzenesulfonyl]-3-spirocyclohexaneindol-1-one 140 mg of the compound obtained in the previous Example are mixed with 5 ml of ethanol, 5 ml of DCM and 5 ml of a 33% solution of methylamine in ethanol. After one hour at RT, the solvents are driven off and the residue is then chromatographed on silica using a DCM/MeOH mixture as the eluent. The product obtained is recrystallized from iso ether.

M.p.=254° C.

EXAMPLE 113

5-Chloro-1,3-dihydro-1-(2-methoxy-4-ureidobenzenesulfonyl)-3-spirocyclohexaneindol-2-one A mixture containing 200 mg of the compound prepared in Example 111 with 5 ml of 20% aqueous ammonia, 5 ml of ethanol and 5 ml of DCM is stirred for 1 hour at RT. After filtration of the reaction medium and evaporation of the solvents, the expected product is crystallized from iso ether.

M.p.=228° C.

EXAMPLE 114

5-Chloro-1,3-dihydro-1-[4-(N-o-tolylureido))-2-methoxybenzenesulfonyl]-3-spirocyclohexaneindol-2-one A mixture containing 250 mg of the compound prepared in Example 2, 10 ml of xylene and 80 mg of orthotolyl isocyanate is refluxed for 18 hours. A white precipitate forms and is filtered off. The reaction medium is extracted with ether and the extract is washed with water and then chromatographed on silica using a DCM/MeOH mixture as eluent. The expected product crystallises from iso ether.

M.p.=182° C.

EXAMPLE 115

Benzyl [4-(5-methoxy-2-oxo-3-spirocyclohexaneindol-yl) sulfonyl-3-methoxybenzoate 60 mg of sodium hydride are poured in small portions into a mixture containing 500 mg of 3-spirocyclohexane-5-methoxyindol-2-one in 50 ml of THF. After 30 minutes at RT, 800 mg of benzyl 3-methoxy-4-chlorosulfonylbenzoate are added and the mixture is stirred for 2 hours at RT. The medium is concentrated and taken up in AcOEt and the mixture is washed with water, dried on sodium sulfate and concentrated. The residue is chromatographed on silica using DCM as the eluent.

NMR: (at 250 MHz in DMSO)

1.2–1.8 ppm: 10H: cyclohexyl
3.6 and 3.8 ppm: 2×3H: 2×OCH$_3$
5.4 ppm: 2H: CO$_2$—CH$_2$—C$_6$H$_5$
6.8–8.2 ppm: 11H: aromatic protons.

EXAMPLE 116

4-(3-Spirocyclohexane-5-methoxy-2-oxoindol-1-yl) sulfonyl-3-methoxy benzoic acid 600 mg of the compound prepared in the previous example are placed in 50 ml of AcOEt and hydrogenated at RT and atmospheric pressure in the presence of 140 mg of palladium-on-charcoal to give 310 mg of the expected acid which is recrystallized from a hexane/ethanol (70/30, v/v) mixture.

M.p.=210° C.

EXAMPLE 117

5-Chloro-1,3-dihydro-1-[4-(N-(ethoxycarbonylmethyl)-carbamoyl-2-methoxybenzenesulfonyl]-3-spirocyclohexane-indol-2-one 450 mg of ethyl glycinate hydrochloride in 20 mg of sodium methoxide are placed in methanol. 200 mg of the compound described in Example 57 in 50 ml of DCM are added and the mixture is stirred at RT for 48 hours. It is extracted with DCM and the extract is washed with water, dried, concentrated and then chromatographed on silica using a DCM/MeOH (99.5/0.5, v/w) mixture as the eluent.

M.p.=164° C.

EXAMPLE 118

1-(4-carbamoyl-2-methoxybenzenesulfonyl)-5-chloro-1,3-dihydro-3-spirocyclohexaneindol-2-one 300 mg of the compound described in example 60 are mixed with 5 ml of 30% aqueous ammonia solution, 10 ml of ethanol and 10 ml of DCM. After one hour at RT, the mixture is concentrated and extracted with DCM and the extract is washed with water, dried, concentrated and than chromatographed on silica using a DCM/MeOH (99/1, v/v) mixture as the eluent to give 109 mg of the expected product.

M.p.=160° C.

EXAMPLE 119

5-Chloro-1,3-dihydro-1-[2-methoxy-4-(N-(2-methoxycarbonylethyl)carbamoyl]-3-spirocyclohexaneindol-2-one A mixture containing 320 mg of the compound described in Example 57 and 2 g of methyl aminobispropionate in 30 ml of tetramethylbenzene is refluxed for 30 minutes. It is extracted with AcOEt and the extract is washed with a 1N solution of hydrochloric acid, dried over sodium sulfate and concentrated. The residue is chromatographed on silica using a DCM/MeOH (99/1, v/v) mixture as the eluent to give 100 mg of the expected product.

M.p.=147° C.

EXAMPLE 120

1-[4-(3-(N-Boc)aminoazetidin-1-ylcarbonyl)-2-methoxybenzenesulfonyl]-5-chloro-1,3-dihydro-3-spirocyclohexaneindol-2-one A mixture containing 300 mg of the compound prepared in Example 57, 900 mg of 3-(N-Boc)aminoazetidin, 1 ml of triethylamine, 10 ml of DCM and 10 ml of methanol is stirred at RT for one hour. It is concentrated and extracted with ethyl acetate and the extract is washed with a 1N solution of hydrochloric acid, dried over sodium sulfate and concentrated. The expected product is obtained after chromatography on silica using DCM/MeOH (99/1, v/v) as the eluent.

M.p.=136° C.

EXAMPLE 121

1-[4-(3-aminoazetidin-1-yl-carbonyl)-2-methoxybenzene sulfonyl]-5-chloro-1,3-dihydro-3-spirocyclohexaneindol-2-one A mixture containing 160 mg of the compound prepared in the previous Example and 3 ml of TFA in 10 ml of DCM is stirred for 30 minutes at RT. The reaction medium is concentrated and crystallised from iso ether and the crystals are filtered off and dried. The product obtained is dissolved in 10 ml of water and then 10 ml of 1N sodium hydroxide; the solution is extracted with DCM and the extract is washed with water, dried over sodium sulfate and concentrated. The expected product is obtained after chromatography on silica using a DCM/MeOH (96/4, v/v) mixture as the eluent.

M.p.=145° C.

EXAMPLE 122

5-Ethoxy-1,3-dihydro-1-[4-(3-dimethylaminopropoxy)-3-methoxybenzenesulfonyl]-3-spirohexaneindol-2-one hydrochloride A) 5-Ethoxy-1,3-dihydro-1-[4-(3-dimethylaminopropoxy)-3-methoxybenzenesulfonyl]-3-spirocyclohexaneindol-2-one A mixture containing 0.5 g of 5-ethoxy-1,3-dihydro-3-spirocyclohexaneindol-2-one, 5 ml of THF and 0.07 g of sodium hydride is stirred at 20° C. for 15 minutes, 1.65 g of 4-(3-bromopropoxy)-3-methoxybenzenesulfonylchloride are then added and the resulting mixture is stirred for 20 hours at RT. It is concentrated under vacuum and extracted with ether and the extract is washed with water and then a 10% solution of sodium carbonate. The expected product crystallizes from pentane and is then recrystallized from iso ether.

M.P.=114°–118° C.

B) 5-Ethoxy-1,3-dihydro-1-(4-(3-dimethylaminopropoxy)-3-methoxybenzenesulfonyl]-3-spirocyclohexaneindol-2-one hydrochloride The compound obtained in the previous step is mixed with 7.5 g of a 33% solution of dimethylamine in ethanol and placed in 10 ml of THF. After stirring for 3 hours, the mixture is concentrated under vacuum and taken up in 10 ml of water and the resulting mixture is extracted with ether. The ether phase is treated with 20 ml of 2 N hydrochloric acid, after which solid potassium carbonate is added to render the solution alkaline to pH 9. The oil which precipitates is extracted with DCM. The expected product crystallizes from ether.

M.P.=135°–138° C.

EXAMPLE 123

1-[4-Aminosulfonamido-2-methoxybenzenesulfonyl]-5-chloro-1,3-dihydro-3-Spirocyclohexaneindol-2-one 0.3 g of the compound prepared in Example 2 are placed in 4 ml of DCM in the presence of 0.5 g of TEA, then 0.3 g of aminosulfonyl chloride prepared according to Chem. Ber., 1958, 91, 1339–1341 is added. After stirring for 2 days at RT, the medium is concentrated under vacuum and extracted with ether and the extract washed with water. After drying, the residue is chromatographed on silica using DCM and then AcOEt as the eluent to give the expected product which crystallises from ether.

M.p.=205°–208° C.

EXAMPLES 124 AND 125

1-(4-Dimethylamino-2-methoxybenzenesulfonyl)-5-methoxy-1,3-dihydro-3-spirocyclohexaneindol-2-one and 1-(4-Methylamino-2-methoxybenzenesulfonyl)-5-methoxy-1,3-dihydro-3- spirocyclohexaneindol-2-one 500 mg of 1-(4-amino-2-methoxybenzenesulfonyl)-5-methoxy-1,3-dihydro-3-spirocyclohexaneindol-2-one are mixed with 1 ml of a 37% aqueous solution of formaldehyde in water, 10 ml of acetonitrile and 430 mg of sodium cyanoborohydride and 0.12 ml of acetic acid is then added. The temperature of the medium rises and the mixture is cooled in an ice bath. Two products of different polarity are formed in succession. 1 ml of an aqueous solution of formaldehyde, 300 mg of sodium cyanoborohydride and 0.12 ml of acetic acid are added to the medium. The mixture is stirred for 1 and a half hours, poured into iced water and then extracted with AcOEt. The extract is washed with water, dried and concentrated to give 2 products which are separated by chromatography on silica using a DCM/AcOEt (98/2, v/v) mixture as the eluent.

M.p.=210° C. (ex. 124)

M.p.=170° C. (ex. 125).

TABLE 5

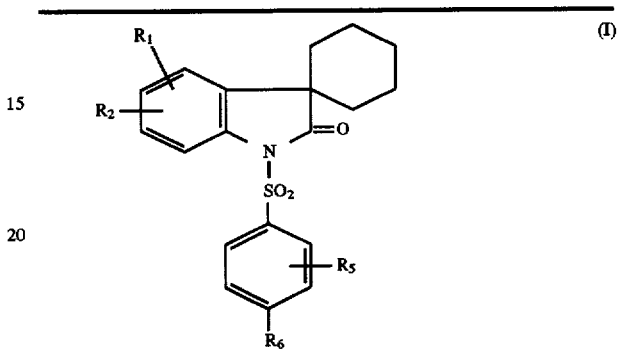

(I)

unless indicated otherwise, substituent $R_6$ is in position 4 and m=1.

| Ex | $R_1$ | $R_2$ | $R_5$ | $R_6$ | M.p. °C. |
|---|---|---|---|---|---|
| 126 | Cl | H | 2-MeO | 3-pyridyl-CONH— | 210 |
| 127 | Cl | H | 2-MeO | 4-MeO-C$_6$H$_4$-CONH— | 192 |
| 128 | Cl | H | 2-MeO | 2-CF$_3$-C$_6$H$_4$-CONH— | 188 |
| 129 | Cl | H | 2-MeO | 2-OMe-C$_6$H$_4$-CONH— | 146 |
| 130 | Cl | H | 2-MeO | 2-Me-C$_6$H$_4$-CH$_2$CONH— | 190 |
| 131 | Cl | H | 2-MeO | 2-OCOCH$_3$-C$_6$H$_4$-CONH— | 147 |
| 132 | Cl | H | 2-MeO | CH$_3$CONH— | 230 |

-continued

| Ex | R₁ | R₂ | R₅ | R₆ | M.p. °C. |
|---|---|---|---|---|---|
| 133 | Cl | H | 2-MeO | 2,6-diMe-C₆H₃-CONH— | 205 |
| 134 | Cl | H | 2-MeO | HO₂C(CH₂)₂—CONH— | 205 |
| 135 | Cl | H | H | 2,3-diMe-C₆H₃-CONH— | 180 |
| 136 | Cl | H | 2-MeO | 2-Cl-C₆H₄-CONH— | 189 |
| 137 | Cl | H | 2-MeO | 2-Et-C₆H₄-CONH— | 176 |
| 138 | MeO | H | 2-MeO | 2-Me-C₆H₄-CONH— | 245 |
| 139 | MeO | H | 2-MeO | 2-iPr-C₆H₄-CONH— | 194 |
| 140 | Cl | H | 2-MeO | 2-iPr-C₆H₄-CONH— | 141 |
| 141 | Cl | H | 2-MeO | 3,4-diMeO-C₆H₃-CONH— | 140 |
| 142 | Cl | H | 2-MeO | 2,4-diMe-C₆H₃-CONH— | 225 |
| 143 | MeO | H | 2-MeO | MeOCH₂CONH— | 161 |
| 144 | MeO | H | 2-MeO | tBuCH₂CONH— | 209 |
| 145 | EtO | H | 2-MeO | 2-Me-C₆H₄-CONH— | 223 |

-continued

| Ex | $R_1$ | $R_2$ | $R_5$ | $R_6$ | M.p. °C. |
|---|---|---|---|---|---|
| 146 | EtO | H | 2-MeO | Me$_2$N—CH$_2$CONH— | 136 |
| 147 | Cl | H | 2-MeO | Me$_2$N—CONH— | 226 |
| 148 | CH$_3$O | H | 2-MeO | Me$_2$N—CONH— | 190 |
| 149 | EtO | H | 2-MeO | Me$_2$N—CONH— | 192 |
| 150 | EtO | H | 2-MeO | MeEtN—CONH— | 160 |
| 151 | EtO | H | 2-MeO | Et$_2$N—CONH— | 168 |
| 152 | EtO | H | 2-MeO | MePrN—CONH— | 137 |
| 153 | Cl | H | 2-MeO | MeCONH—(piperidine)—N—CO | 157 |
| 154 | Cl | H | 2-MeO | Me$_2$N—(CH$_2$)$_2$—NHCO— | 163 |
| 155 | Cl | H | 2-MeO | Me$_2$N—CO— | 192 |
| 156 | Cl | H | 2-MeO | Me$_2$N—SO$_2$— | 231 |
| 157 | Cl | H | 2-MeO | H | 106 |
| 158 | Cl | H | 2-MeO | Me—N(piperazine)N—SO$_2$— | 226 |
| 159 | Cl | H | 2-MeO | MeOCO,Bz-HC—NHCO— | 117 |
| 160 | MeO | H | 2-MeO | O$_2$N— | 188 |
| 161 | Cl | H | 2-MeO | BzOCO— | RMN |

-continued

| Ex | R₁ | R₂ | R₅ | R₆ | M.p. °C. |
|---|---|---|---|---|---|
| 162 | Cl | H | 2-MeO | 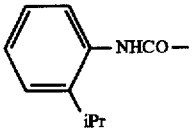 2-iPr-phenyl-NHCO— | 215 |
| 163 | MeO | H | 2-MeO | NH₂— | 188 |
| 164 | MeO | H | 2-MeO | MeO— | 172 |
| 165 | MeO | H | 2-MeO | 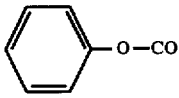 phenyl-O—CO— | 162 |
| 166 | MeO | H | 2-MeO | 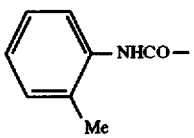 2-Me-phenyl-NHCO— | 198 |
| 167 | EtO | H | 2-MeO | H₂N— | 177 |
| 168 | MeO | 6-MeO | 2-MeO | MeO— | 183 |
| 169 | EtO | H | 2-MeO | 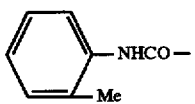 2-Me-phenyl-NHCO— | 150 |
| 170 | EtO | H | 2-MeO | BzOCO— | 135 |
| 171 | EtO | H | 2-MeO | HOOC— | RMN |
| 172 | EtO | H | 2-MeO | MeNHCO— | 239 |
| 173 | EtO | H | 2-MeO | MeO— | 131 |
| 174 | EtO | H | 3-MeO | MeO— | 127 |
| 175 | EtO | H | 2-MeO | Me₂N— | 167 |
| 176 | EtO | H | 3-MeO | 4,5-di-MeO | 130 |
| 177 | EtO | H | 2-MeO | 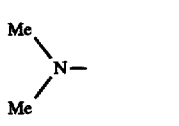 3-Me-pyridyl-NHCO— | 195 |
| 178 | EtO | H | 2-MeO | 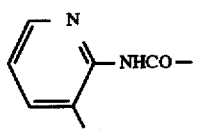 pyrazinyl-CH₂NHCO— | 168 |
| 179 | EtO | H | 2-MeO | N₂O | 160 |
| 180 | EtO | H | 2-Me | MeO | 176 |
| 181 | EtO | H | 3-MeO | CH₂=CH—CH₂O— | 130 |
| 182 | CF₃O | H | 2-MeO | MeO | 127 |
| 183 | EtO | H | 2-MeO | Me₂CHNHCO— | 171 |
| 184 | EtO | H | 2-MeO | EtOCOCH₂NHCO— | 203 |
| 185 | EtO | H | 2-MeO | 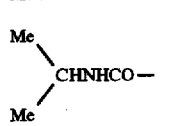 phenyl-O—CO—NH— | 181 |
| 186 | EtO | H | 2-MeO | 4,5-di-MeO | 136 |
| 187 | EtO | H | 2-Me | 4-MeO, 5-Cl | 129 |

-continued

| Ex | R₁ | R₂ | R₅ | R₆ | M.p. °C. |
|---|---|---|---|---|---|
| 188 | EtO | H | 2-MeO | Bz—N⟨piperidine⟩—NHCO— | 188 |
| 189 | EtO | H | 2-MeO | HO(CH₂)₂—NHCO— | 157 |
| 190 | EtO | H | 2-MeOCO | H | 117 |
| 191 | EtO | H | 2-MeO | Me₂N—(CH₂)₃—O—, HCl | 212 |
| 192 | EtO | H | 2-MeO | ⟨thiophene⟩—CONH— | 181 |
| 193 | EtO | H | 2-MeO | Et₂CH—CONH— | 206 |
| 194 | EtO | H | 2-MeO | BzOCOCH₂NHCO— | RMN |
| 195 | EtO | H | 2-MeO | ⟨2-Me-phenyl⟩-N(Me)—CO— | 144 |
| 196 | EtO | H | 2-MeO | ⟨phenyl⟩—OCO— | 152 |
| 197 | EtO | H | 2-MeO | Et₂N—CO— | 148 |
| 198 | EtO | H | 2-MeO | Et₂N—CS— | 128 |
| 199 | EtO | H | 2-MeO | CN—CH₂NH—CO— | 232 |
| 200 | EtO | H | 2-MeO | EtO₂C—CH₂—N(Me)—CO | RMN |
| 201 | EtO | H | 2-MeO | HO₂C—CH₂NH—CO— | 137 |
| 202 | Cl | H | 2-MeO | (Et)₂N—CO—NH— | 194 |
| 203 | EtO | H | 2-MeO | ⟨cyclohexyl⟩—CONH— | 214 |
| 204 | EtO | H | 2-MeO | H₂N(CH₂)₃O— | 136–140 |
| 205 | EtO | H | 2-MeO | (CH₃)₃N⁺(CH₂)₃O— I⁻ | 145–150 |
| 206 | C₆H₅O | H | 2-MeO | 4-MeO | 130 |
| 207 | EtO | H | 2-MeO | ⟨cyclohexyl⟩—CS—NH— | 210 |

-continued

| Ex | R₁ | R₂ | R₅ | R₆ | M.p. °C. |
|---|---|---|---|---|---|
| 208 | EtO | H | 2-MeO | Et\‌CH—CON—\‌/ \| \‌Et Me | 138 |
| 209 | EtO | H | 2-MeO | EtO—CH₂O— | 160 |

The NMR spectra are run in DMSO at 200 MHz.
NMR spectrum of Example 161
1.3–1.8 ppm: 10H: cyclohexyl
3.5 ppm: 3H: OCH₃
5.3 ppm: 2H: O—CH₂—C₆H₆—
7.2–8.2 ppm: 11H: aromatic protons
M spectrum of Example 171
1.15 ppm: 3H: CH₃
1.19–2 ppm: 10H: cyclohexyl
3.6 ppm: 3H: OCH₃
4 ppm : 2H: OCH₂—CH₃
6.7–8.2 ppm: 6H: aromatic protons.
NMR Spectrum of Example 200
1–2.2 ppm: 16H: cyclohexyl+2CH₃
3 ppm: 3H: NCH₃
4–4.4 ppm: 6H: aromatic protons
6.8–8.2 ppm: 6H: aromatic protons
A resolution of the signals is observed; this is associated with the amide isomerism.

EXAMPLE 210

1-(4-benzyloxy-2-methoxybenzenesulfonyl)-5-ethoxy-1,3-dihydro-3-spirocyclohexane A) Potassium 4-benzyloxy-2-methoxybenzenesulfonate This preparation is carried out according to K. Hofmann et al., Liebigs. Ann. Chem., 1982, 282–297.

10.5 g of 4-benzyloxy-2-methoxybenzene are mixed at 5° C. with 30 ml of DCM and 8 ml of trimethylsilyl chlorosulfonate are added for 15 minutes at a temperature between 5° and 10° C.; after stirring for 15 minutes, 50 g of ice are added. The mixture is washed with ethyl ether, treated with potassium hydrogencarbonate and then concentrated under vacuum. After drying, the mixture is taken up in 150 ml of methanol. The insoluble material is filtered off at the boil and the expected product then crystallizes at 5° C.

M.p.>300° C.

The structure of the compound is confirmed by the analysis of the NMR spectrum.

B) 4-benzyloxy-2-methoxybenzenesulfonyl chloride 2.8 g of the compound prepared in the previous Example are mixed with 30 ml of POCl₃ and the mixture is refluxed for 3 hours. It is concentrated under vacuum, treated with 20 g of ice and extracted with ethyl ether and the extract is washed with 30 ml of N sodium hydroxide and then water. The medium is concentrated and the oil obtained is triturated in 30 ml of iso ether. The expected product (0.7 g) crystallizes.

M.p.=95° C.

C) 1-(4-benzyloxy-2-methoxybenzenesulfonyl)-5-ethoxy-1,3-dihydro-3-spirocyclohexaneindol-2-one This compound is prepared by the usual procedure. It crystallizes from iso ether.

M.p.=135° C.

The structure of the compound is verified by analysis of the NMR spectrum in two dimensions (NOESY effect: Nuclear Overhauser Effect Spectroscopy).

The compound of the next Example is subsequently prepared by debenzylation.

EXAMPLE 211

5-Ethoxy-1,3-dihydro-1-(4-hydroxy-2-methoxybenzenesulfonyl)-3-spirocyclohexaneindol-2-one M.p.=209° C.

The compounds described in Table 6 below were also prepared by using the methods of the present invention.

TABLE 6

| Example | $R_1$ | $CR_3R_4$ | $R_5$ | M.p. °C. or NMR |
|---|---|---|---|---|
| 212 | $CH_3S-$ | 4,4-dimethylcyclohexane | MeO— | 145 |
| 213 | EtO— | 4,4-dimethylcyclohexane | OH— | NMR |
| 214 | EtO— | cycloheptane | $O_2N-$ | 125 |
| 215 | EtO— | cycloheptane | $H_2N-$ | 128 |
| 216 | EtO— | cycloheptane | $Et_2NCONH-$ | 179 |
| 217 | Cl— | 4,4-dimethylcyclohexane | $O_2N-$ | 169 |
| 218 | Cl— | 4,4-dimethylcyclohexane | $H_2N-$ | 222 |
| 219 | Cl— | 4,4-dimethylcyclohexane | $Et_2NCONH-$ | 201 |
| 220 | Cl— | cycloheptane | $O_2N-$ | 137 |
| 221 | Cl— | cycloheptane | $H_2N-$ | 184 |
| 222 | Cl— | cycloheptane | $Et_2NCONH-$ | 172 |
| 223 | Cl— | tetrahydropyran-4 | $O_2N-$ | 212 |
| 224 | Cl— | tetrahydropyran-4 | $H_2N-$ | 220 |
| 225 | Cl— | tetrahydropyran-4 | $Et_2NCONH-$ | 228 |
| 226 | EtO— | bicyclic structure | $O_2N-$ | 88 |
| 227 | EtO— | bicyclic structure | $H_2N-$ | 241 |
| 228 | EtO— | bicyclic structure | $Et_2NCONH-$ | 138 |
| 229 | EtO— | tetrahydropyran-4 | MeO— | 177 |
| 230 | F— | 4,4-dimethylcyclohexane | $O_2N-$ | 137 |
| 231 | F— | 4,4-dimethylcyclohexane | $H_2N-$ | 130 |
| 232 | F— | 4,4-dimethylcyclohexane | $Et_2NCONH-$ | 120 |
| 233 | $CF_3-$ | 4,4-dimethylcyclohexane | $O_2N-$ | 163 |
| 234 | $CF_3-$ | 4,4-dimethylcyclohexane | $H_2N-$ | 231 |
| 235 | $CF_3-$ | 4,4-dimethylcyclohexane | $Et_2NCONH-$ | 186 |
| 236 | Cl— | tetrahydrothiopyran | $O_2N-$ | 116 |
| 237 | Cl— | tetrahydrothiopyran | $H_2N-$ | 229 |
| 238 | EtO— | bicyclo [3.3.1] nonane | $O_2N-$ | 140 |
| 239 | EtO— | bicyclo [3.3.1] nonane | $H_2N-$ | 232 |
| 240 | EtO— | bicyclo [3.3.1] nonane | $Et_2NCONH-$ | 212 |
| 241 | EtO— | bicyclo [2.2.1] heptane | $O_2N-$ | NMR |
| 242 | EtO— | bicyclo [2.2.1] heptane | $H_2N-$ | 189 |
| 243 | EtO— | bicyclo [2.2.1] heptane | $Et_2NCONH-$ | 223 |
| 244 | EtO— | cyclohexane | MeS— | 126 |
| 245 | EtO— | cyclohexane | $CH_3NH-$ | 157 |
| 246 | EtO— | cyclohexane | $iPrN(CH_3)-$ | 109 |

TABLE 6-continued

| Example | R₁ | CR₃R₄ | R₅ | M.p. °C. or NMR |
|---|---|---|---|---|
| 247 | EtO— | cyclohexane | [2-CH₃-C₆H₄-CH₂]₂N— | 172 |
| 248 | Cl— | tetrahydrothiopyran | MeO— | 79 |
| 249 | Cl— | tetrahydrothiopyran | Et₂NCON— | 214 |
| 250 | EtO— | cyclohexane | 2-CH₃-C₆H₄-CH₂N— | 164 |
| 251 | EtO— | cyclohexane | iPrCON(CH₃)— | 138 |
| 252 | EtO— | cyclohexane | cyclohexyl-CONH— | 210 |
| 253 | EtO— | cyclohexane | Et₂NCH₂CONH— | 110 |
| 254 | EtO— | cyclohexane | EtOCOCH₂CONH— | 116 |
| 255 | EtO— | cyclohexane | EtOCONH— | 158 |
| 256 | EtO— | cyclohexane | EtNHCO— | 188 |
| 257 | EtO— | cyclohexane | nBuNHCO— | 213 |
| 258 | EtO— | cyclohexane | iBuNHCO— | 170 |
| 259 | EtO— | cyclohexane | tBuNHCO— | 248 |
| 260 | EtO— | cyclohexane | 4-(MeN)-cyclohexyl-NHCO— | 211 |
| 261 | EtO— | cyclohexane | Et₂N(CH₂)₂NHCO— | 130 |
| 262 | EtO— | cyclohexane | Et₂NCH₂C(Me)₂NHCO— | 128 |
| 263 | EtO— | cyclohexane | EtOCOC(Me)₂NHCO— | 124 |
| 264 | EtO— | cyclohexane | EtNHCS— | 180 |
| 265 | EtO— | cyclohexane | nBuNHCS— | 127 |
| 266 | EtO— | cyclohexane | MeNHCS— | 251 |
| 267 | EtO— | cyclohexane | EtOCOCH₂NHCO— | NMR |
| 268 | EtO— | cyclohexane | iBu—CH(COOCH₃)—NHCO— | 102 |
| 269 | EtO— | cyclohexane | EtOCOCH(CH₃)NHCO— | 94 |
| 270 | EtO— | 4,4-dimethylcyclohexane | Et₂NCONH— | 148 |
| 271 | EtO— | cyclohexane | iPrN(Et)CONH— | 179 |
| 272 | EtO— | cyclohexane | (iPr)₂NCONH— | 204 |
| 273 | EtO— | cyclohexane | (nPr)₂NCONH— | 155 |
| 274 | EtO— | cyclohexane | (Et)₂NCON(CH₃)— | 118 |

NMR at 200 MHz in DMSO—Example 213

10.8 ppm: s: 1H
7.7 ppm: d: 1H
7.45 ppm: d: 1H
7.05 ppm: s: 1H
6.85 ppm: d: 1H
6.45 ppm: s: 1H
6.5 ppm: d: 1H
4 ppm: q: 2H
3.5 ppm: s: 3H
1.2–1.7 ppm: m: 11H
1.05 ppm: s: 3H
0.95 ppm: s: 3H NMR at 200 MHz in DMSO—Example 267

6.7–8.2 ppm: m: 6H
3.8–4.3 ppm: m: 6H
3.6 ppm: s: 3H
0.7–2.1 ppm: m: 20H

NMR at 200 MHz in DMSO—Example 241

8.2 ppm: d: 1H
7.95 ppm: m: 2H
7.6 ppm: d: 1H
6.9 ppm: m: 2H
4 ppm: q: 2H
3.7 ppm: s: 3H
2.2 ppm: m: 4H
1.3 ppm: m: 9H

EXAMPLES 275 AND 276

5-Ethoxy-1,3-dihydro-1-[2-methoxy-4-(pyrrol-1-yl) benzenesulfonyl]-3-spirocyclohexaneindol-2-one
and
5-ethoxy-1,3-dihydro-1-[2-methoxy-4-(Δ3-pyrrolin-1-yl) benzenesulfonyl]-3-spirocyclohexaneindol-2-one A) 5-Ethoxy-1,3-dihydro-1-(2-methoxy-4-nitrobenzenesulfonyl)-3-spirocyclohexaneindo-2-one A solution of 15 g of 5-ethoxy-1,3-dihydro-3-spirocyclohexaneindol-2-one in 150 ml of THF is cooled in an ice bath to a temperature between 10° C. and 15° C. 2.4 g of sodium hydride as a 60% dispersion in oil are added over 2 hours and 18 g of 2-methoxy-4-nitrobenzenesulfonyl chloride are then introduced in portions over 30 minutes. After stirring for 18 hours at RT, the suspension obtained is poured into an iced solution of sodium chloride and then extracted with AcOEt. The organic phase is dried over sodium sulfate and evaporated to dryness and the residue is then crystallized from 200 ml of hot iso ether to give 23 g of the expected product. M.p.=160° C.

This compound is also obtained by following the procedure described below.

A') 5-Ethoxy-1,3-dihydro-1-(2-methoxy-4-nitrobenzenesulfonyl)-3-spirocyclohexaneindol-2-one A solution of 15 g of 5-ethoxy-1,3-dihydro-3-spirocyclohexaneindol-2-one in 300 ml of THF is cooled to about −50° C. and 7.2 g of potassium tert-butylate are added. The mixture is stirred, the temperature being allowed to rise to about 0° C., and then cooled to −50° C. and a solution of 16.2 g of 2-methoxy-4-nitro benzenesulfonyl chloride in THF is added. The mixture is stirred for 1 hour at RT, 100 ml of water are added and the solvent is evaporated off under vacuum. The aqueous phase is extracted with DCM and dried over magnesium sulfate and the solvent is evaporated off under vacuum to give the expected product after crystallization from hot iso ether.

The following nitro derivatives are prepared by the latter procedure starting from the appropriate 1,3-dihydroindol-2-ones:

| R₁ | CR₃R₄ | M.p. °C. or NMR |
|---|---|---|
| Cl— | 4,4-dimethylcyclohexane | 169 |
| EtO— | 4,4-dimethylcyclohexane | 110 |
| F— | 4,4-dimethylcyclohexane | 137 |
| CF₃ | 4,4-dimethylcyclohexane | |
| Cl— | cycloheptane | 137 |
| EtO— | cycloheptane | 125 |
| Cl— | tetrahydropyran-4 | 212 |
| Cl— | tetrahydrothiopyran-4 | 116 |
| EtO— | (bicyclic structure) | 88 |
| EtO— | (bicyclic structure) | 140 |
| EtO— | (bicyclic structure) | NMR* |

*NMR spectrum at 200 MHz in DMSO:
1.3 ppm: t: 3H
1.3–1.5 ppm: mt: 6H
2.2 ppm: mt: 4H
3.7 ppm: s: 3H
4.0 ppm: q: 2H
7.0 ppm: mt: 2H
7.6 ppm: d: 1H
7.9 ppm: mt: 2H
8.2 ppm: d: 1H B) 1-(4-Amino-2-methoxybenzenesulfonyl)-5-ethoxy-1, 3-dihydro-3-spirocyclohexaneindol-2-one A suspension containing 20 g of the compound obtained in the previous step, 20 g of iron powder, 70 ml of water and 70 ml of 96° alcohol is brought to the reflux point; a solution of 7 ml of concentrated hydrochloric acid in 35 ml of water is added over 30 minutes. After 4 hours under reflux, 15 ml of sodium hydroxide solution are added and the mixture is then extracted with DCM. The organic phase is filtered on CéliteR and then dried over sodium sulfate. The residue is crystallized from 100 ml of a hot iso ether/AcOEt mixture (80/20; v/v) to give 15.8 g of the expected product. M.p.= 177° C.

This compound is also obtained by following the procedure described below.

B') 1-(4-Amino-2-methoxybenzenesulfonyl)-5-ethoxy-1,3-dihydro-3-spirocyclohexaneindol-2-one A solution of 0.5 g of the compound obtained in step A) in 10 ml of EtOH is cooled to about 5° C. and 0.8 ml of concentrated HCl and 0.4 g of tin powder are added. The mixture is heated at 40° C. for 45 minutes and the solvent is evaporated off under vacuum. The residue is neutralized by the addition of NaOH, extracted with AcOEt, dried over magnesium sulfate and filtered on CéliteR and the filtrate is evaporated under vacuum. The residue is chromatographed on silica using a DCM/MeOH mixture (99/1; v/v) as the eluent to give the expected product.

The following anilines are also prepared by the latter procedure:

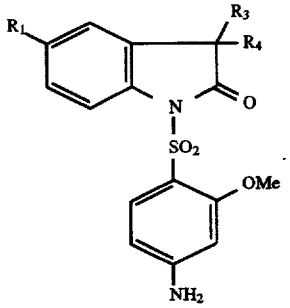

| $R_1$ | $CR_3R_4$ | M.p. °C. |
|---|---|---|
| Cl— | 4,4-dimethylcyclohexane | 222 |
| EtO— | 4,4-dimethylcyclohexane | 230 |
| F— | 4,4-dimethylcyclohexane | 130 |
| $CF_3$— | 4,4-dimethylcyclohexane | |
| Cl— | cycloheptane | 184 |
| EtO— | cycloheptane | 128 |
| Cl— | 4-tetrahydropyran | 220 |
| Cl— | 4-tetrahydrothiopyran | 229 |
| EtO— | 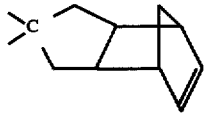 | 241 |
| EtO— | 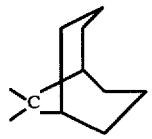 | 232 |
| EtO— | 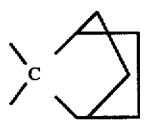 | 189 |

B") The compound obtained in step B) above can also be prepared from the corresponding nitro derivative by hydrogenation in the presence of 10% palladium-on-charcoal for 2 hours at 50° C. under a pressure of 1 bar.

C) 5-Ethoxy-1,3-dihydro-1-[2-methoxy-4-(pyrrol-1-yl)-benzenesulfonyl]-3-spirocyclohexaneindol-2-one and 5-ethoxy-1,3-dihydro-1-[2-methoxy-4-(Δ3-pyrrolin-1-yl)-benzenesulfonyl]-3-spirocyclohexaneindol-2-one A mixture containing 500 mg of the compound prepared in step B), 10 ml of DMF, 0.3 g of sodium carbonate and 300 mg of cis-1,4-dichlorobut-2-ene is refluxed for 4 hours. The reaction mixture is poured into a water/ice mixture and then extracted with AcOEt and washed with water; the solvent is evaporated off and the residue obtained is then chromatographed on silica using a DCM/heptane mixture (95/5; v/v) and then pure DCM as the eluent. 70 mg of the less polar product (compound of Example 275), m.p.=174° C., are collected, followed by 60 mg of the more polar product (compound of Example 276), m.p.=170° C.

The compounds described in the Tables of steps A) and B) above can be used to prepare compounds according to the invention which are analogous to that obtained in step C).

EXAMPLE 277

5-Ethoxy-1,3-dihydro-1-[2-methoxy-4-(pyrrolidin-1-yl)benzenesulfonyl]-3-spirocyclohexaneindol-2-one 450 mg of the compound obtained in Example 276 are placed in 25 ml of 95° EtOH and 25 ml of AcOEt, in the presence of 150 mg of 5% palladium-on-charcoal, and are hydrogenated for 4 hours at 35° C. under a pressure of 40 bar. The catalyst is filtered off and the filtrate is evaporated to dryness. The expected product crystallizes from iso ether. m=110 mg. M.p.=185° C.

EXAMPLE 278

5-Ethoxy-1,3-dihydro-1-[4-(isoindolin-2-yl)-2-methoxybenzenesulfonyl]-3-spirocyclohexaneindol-2-one A mixture containing 500 mg of the compound prepared in Example 275 step B), 10 ml of DMF, 0.5 ml of TEA and 310 mg of α,α'-dibromoorthoxylene is refluxed for 2 hours. The reaction medium is poured into a water/ice mixture, extracted with AcOEt, dried over sodium sulfate and evaporated to dryness. The residue is chromatographed on silica using DCM and then DCM/AcOEt (95/5; v/v) as the eluent to give the expected product, which is crystallized from iso ether. m=170 mg. M.p.=190° C.

EXAMPLE 279

5-Ethoxy-1,3-dihydro-1-[2-methoxy-4-((3-methyl-thien-2-yl)carboxamido)benzenesulfonyl]-3-spirocyclohexaneindol-2-one A mixture containing 500 mg of the compound prepared in Example 275 step B), 10 ml of DCM, 2 ml of pyridine and 250 mg of 3-methylthiophene-2-carboxylic acid chloride is stirred for 3 hours at RT. The medium is washed with 1N hydrochloric acid and then with water. It is dried over sodium sulfate and then evaporated to dryness. The residue is chromatographed on silica using DCM as the eluent. The expected product recrystallizes from iso ether. m=0.21 g. M.p.=174° C.

EXAMPLE 280

1-[4-(N-Benzylcarbamoyl)-2-methoxybenzenesulfonyl]-5-ethoxy-1,3-dihydro-3-spirocyclohexaneindol-2-one A) Benzyl 3-methoxy-4-[(5-ethoxy-2,3-dihydro-2-oxo-3-spirocyclohexaneindol-1-yl)sulfonyl]benzoate 1.4 g of sodium hydride are added in small portions to a solution of 11.8 g of 5-ethoxy-1,3-dihydro-3-spirocyclohexaneindol-2-one in 100 ml of THF. After stirring for 30 minutes at RT, 17 g of benzyl 4-chlorosulfonyl-3-methoxybenzoate are added and stirring is maintained at

71

RT for 1 hour. The reaction medium is poured into 400 ml of a water/alcohol mixture (50/50; v/v). The precipitate formed is filtered off, dried and then recrystallized from alcohol.

m=22.65 g. M.p.=135° C.

B) 3-Methoxy-4-[(5-ethoxy-2,3-dihydro-2-oxo-3-spirocyclohexaneindol-1-yl)sulfonyl]benzoic acid 2.5 g of 10% palladium-on-charcoal in oil are added to a solution of 22.65 g of the benzyl ester prepared in the previous step in 600 ml of AcOEt and the mixture is then hydrogenated for 2 hours at 40° C. under atmospheric pressure. The insoluble material is filtered off and the medium is then concentrated. The expected product crystallizes from pentane.

m=18.3 g. M.p.=181° C.

C) 3-Methoxy-4-[(5-ethoxy-2,3-dihydro-2-oxo-3-spirocyclohexaneindol-1-yl)sulfonyl]benzoyl chloride A solution of 2.3 g of the above acid in 20 ml of thionyl chloride is refluxed for 3 hours. The reaction medium is concentrated to dryness and the product is used in the crude form, as a solution in DCM, in the next step.

D) 1-[4-(N-Benzylcarbamoyl)-2-methoxybenzenesulfonyl]-5-ethoxy-1,3-dihydro-3-spirocyclohexaneindol-2-one A mixture containing 500 mg of the compound prepared in the previous step and 200 mg of benzylamine in 20 ml of DCM and 0.5 ml of TEA is stirred at RT for 30 minutes. It is washed with a 1N solution of HCl, dried over sodium sulfate and concentrated. The expected product crystallizes from iso ether.

m=440 mg. M.p.=196° C.

The compound of Example 280 does not belong to the compounds of formula (I) according to the invention, but the intermediate obtained in step C) is used to prepare the compound of Example 282.

The procedure described in Example 280 step D) is also used, together with the appropriate amines, to prepare the compounds of Examples 318–328.

EXAMPLE 281

1-[4-(2-Carbamoylpyrrolidin-1-ylcarbonyl)-2-methoxybenzenesulfonyl]-5-chloro-1,3-dihydro-3-spiro-5 cyclohexaneindol-2-one A) Phenyl 4-[(5-chloro-2,3-dihydro-2-oxo-3-spirocyclohexaneindol-1-yl)sulfonyl]-3-methoxybenzoate A mixture containing 1 g of 5-chloro-1,3-dihydro-3-spirocyclohexaneindol-2-one, 50 ml of THF and 115 mg of sodium hydride is stirred for 30 minutes at RT under nitrogen. 1.5 g of 2-methoxy-4-phenoxycarbonylbenzenesulfonyl chloride are introduced and stirring is maintained for 20 hours at RT. The reaction medium is concentrated under vacuum and the residue is taken up with 30 ml of water and extracted with AcOEt. The organic phase is washed, dried and concentrated under vacuum. The product obtained is purified by chromatography on silica using an iso ether/hexane mixture (40/60; v/v) as the eluent to give 1.4 g of the expected compound. M.p.=165° C.

B) 1-[4-(2-Carbamoylpyrrolidin-1-ylcarbonyl)-2-methoxybenzenesulfonyl]-5-chloro-1,3-dihydro-3-spirocyclohexaneindol-2-one A mixture containing 300 mg of the compound prepared in the previous step, 500 mg of (L)-prolinamide hydrochloride, 1 ml of TEA and 20 ml of prehnitene is refluxed for 1 hour. After cooling, the reaction medium is taken up with AcOEt, washed with a 1N solution of HCl and with water and then dried over sodium sulfate and concentrated. The residue is chromatographed on silica using a DCM/MeOH mixture (98/2; v/v) as the eluent to give 0.09 g of the expected product. M.p.=142° C.

EXAMPLE 282

5-Ethoxy-1,3-dihydro-1-[2-methoxy-4-(2-methoxycarbonylpyrrolidin-1-ylcarbonyl)benzenesulfonyl]-3-spirocyclohexaneindol-2-one 500 mg of the hydrochloride of the methyl ester of (L)-proline, 0.5 ml of TEA and 20 ml of DCM are added to 500 mg of 3-methoxy-4-[(5-ethoxy-2,3-dihydro-2-oxo-3-spirocyclohexaneindol-1-yl)sulfonyl]benzoyl chloride, prepared in Example 6 step C). After stirring for one hour at RT, the mixture is washed with 1N HCl, dried and concentrated. The residue is chromatographed on silica using a DCM/MeOH mixture (98/2; v/v) as the eluent to give 300 mg of the expected product, which is characterized by its NMR spectrum.

NMR at 200 MHz in DMSO (2.5 ppm):

1.25 ppm: t: 3H
1.3–2.35 ppm: m: 14H
3.1–3.7 ppm: m: 8H
3.8 ppm: q: 2H
4.35 ppm: mt: 1H
6.7–8 ppm: m: 6H

EXAMPLE 283

1-[4-(N'-Cyclopentylureido)-2-methoxybenzenesulfonyl]-5-ethoxy-1,3-dihydro-3-spirocyclohexaneindol-2-one A) 5-Ethoxy-1,3-dihydro-1-(2-methoxy-4-phenoxycarboxamidobenzenesulfonyl)-3-spirocyclohexaneindol-2-one A mixture containing 2 g of 1-(4-amino-2-methoxybenzenesulfonyl)-5-ethoxy-1,3-dihydro-3-spirocyclohexaneindol-2-one (prepared in Example 275 step B)), 3.6 ml of phenyl chloroformate and 120 ml of ether is cooled to a temperature below 5° C. 960 mg of sodium hydroxide in 16 ml of water are added and the temperature is allowed to rise for 24 hours, with stirring. The precipitate is filtered off and washed with water and then with ether. The residue is chromatographed on silica using DCM as the eluent to give the expected product. M.p.=181° C.

B) 1-[4-(N'-Cyclopentylureido)-2-methoxybenzenesulfonyl]-5-ethoxy-1,3-dihydro-3-spirocyclohexaneindol-2-one 2 g of the compound prepared in the previous step are dissolved in 40 ml of 100° EtOH and 30 ml of DCM. 2 ml of cyclopentylamine are added and the mixture is stirred for 18 hours at RT. The alcohol is evaporated off under vacuum and the residue is then chromatographed on silica using a DCM/AcOEt mixture (95/5; v/v) as the eluent to give 1.8 g of the expected product, which crystallizes from iso ether. M.p.=195° C.

EXAMPLE 284

5-Chloro-1,3-dihydro-1-[4-(N',N'-diethylureido)-2-methoxybenzenesulfonyl]-3-spiro-(tetrahydrothiopyran-4-yl-1-oxide)indol-2-one This is prepared in the same manner as in Example 283 (steps A) and B)).

A) 5-Chloro-1,3-dihydro-1-[4-(N',N'-diethylureido)-2-methoxybenzenesulfonyl]-3-spiro(tetrahydrothiopyran-4-yl)indol-2-one, m.p.=214° C., from 5-chloro-1,3-dihydro-1-[4-amino-2-methoxybenzenesulfonyl]-3-spiro-(tetrahydrothiopyran-4-yl)indol-2-one, m.p.=229° C.

B) 5-Chloro-1,3-dihydro-1-[4-(N',N'-diethylureido)-2-methoxybenzenesulfonyl]-3-spiro(tetrahydrothiopyran-4-yl-1-oxide)indol-2-one A mixture of 0.45 g of the compound prepared in step A) and 0.2 g of sodium periodate in 3 ml of methanol and 2 ml of water is stirred for 24 hours at RT. The precipitate is filtered off and the methanol is evaporated off from the filtrate under reduced pressure. The residue is extracted with DCM and dried over magnesium sulfate and the solvent is evaporated off. The residue is chromatographed on a silica column using a DCM/methanol mixture (98/2; v/v) as the eluent and 0.4 g of the expected product is isolated.

M.p.=217° C.

EXAMPLE 285

5-Chloro-1,3-dihydro-1-[4-(N',N'-diethyl ureido)-2-methoxybenzenesulfonyl]-3-spiro(tetrahydro thiopyran-4-yl-1,1-dioxyde)indol-2-one A mixture of 0.45 g of the compound of Example 284 and 0.5 g of metachloroperbenzoic acid in 10 ml of DCM is stirred at RT for 4 hours. 12 ml of a saturated aqueous solution of sodium bicarbonate are then added and the organic phase is decanted, washed with water, dried and evaporated under reduced pressure. The residue is recrystallized from a mixture of cyclohexane and ethyl acetate (7/3; v/v) to give 0.35 g of the expected product. M.p.=211° C.

EXAMPLE 286

1-[4-(N'-Cyclopentylthioureido)-2-methoxybenzenesulfonyl]-5-ethoxy-1,3-dihydro-3-spirocyclohexaneindol-2-one The compound obtained in Example 283 is placed in 50 ml of toluene in the presence of 1.5 g of Lawesson's reagent. The mixture is refluxed for 24 hours. The toluene is driven off and the residue is then chromatographed on silica using pure DCM and then a DCM/AcOEt mixture (ranging up to 90/10; v/v) as the eluent to give the expected product, which crystallizes from iso ether. M.p.=197° C.

EXAMPLE 287

1-[4-(3-(N-Boc-amino)azetidin-1-ylcarboxamido)-5-methoxybenzenesulfonyl]-2-ethoxy-1,3-dihydro-3-spirocyclohexaneindol-2-one A) 1-Benzhydryl-3-(N-Boc-amino)azetidine A mixture containing 5 g of 3-amino-1-benzhydrylazetidine and 5 g of (Boc)$_2$O in 130 ml of dioxane and 4 ml of TEA is stirred at RT for 2 hours. The dioxane is evaporated off and the residue is taken up with AcOEt and washed with water. It is dried over sodium sulfate and then evaporated to dryness. The expected product crystallizes from iso ether. m=6 g.

B) 3-(N-Boc-amino)azetidine hydrochloride

A mixture containing 6 g of the compound prepared in the previous step, 300 ml of 95° EtOH, 700 mg of palladium hydroxide and 3 ml of concentrated HCl is prepared. It is hydrogenated for 2 hours at 35°–40° C. under a pressure of 2 bar. The catalyst is filtered off and the filtrate is evaporated to dryness. The expected product crystallizes from iso ether m=3.4 g.

C) 1-[4-(3-(N-Boc-amino)azetidin-1-ylcarboxamido)-5-methoxybenzenesulfonyl]-2-ethoxy-1,3-dihydro-3-spirocyclohexaneindol-2-one A mixture containing 500 mg of the compound prepared in Example 283 step A), 20 ml of 100° alcohol, 15 ml of DCM, 250 mg of the compound prepared in step B) and 0.5 ml of TEA is stirred for 24 hours at RT. The solvents are evaporated off and the residue is then chromatographed on a silica column using a DCM/AcOEt mixture (95/5; v/v) as the eluent. The expected product crystallizes from iso ether.

m=200 mg. M.p.=156° C.

EXAMPLE 288

1-[4-(N'-Carboxymethyl-N'-methylureido)-2-methoxybenzenesulfonyl]-5-ethoxy-1,3-dihydro-3-spirocyclohexaneindol-2-one A mixture containing 500 mg of the compound prepared in Example 283 step A), 20 ml of 100° EtOH, 15 ml of DCM, 1.5 g of sarcosine and 2 ml of triethylamine is prepared. After stirring for 24 hours at RT, the solvents are evaporated off, the residue is then taken up with hot AcOEt and the insoluble material is filtered off. The filtrate is evaporated to dryness and the residue is then chromatographed on silica using pure DCM and then a DCM/MeOH mixture (85/15; v/v) as the eluent to give the expected product, which is characterized by its NMR spectrum at 200 MHz in DMSO (2.5 ppm):

1.3 ppm: t: 3H 1.4–2.1 ppm: m: 10H 2.95 ppm: s: 3H 3.5 ppm: s: 3H 3.9 ppm: s: 2H 4 ppm: q: 2H 6.7–7.9 ppm: m: 6H 9.45 ppm: bs: 1H

EXAMPLE 289

5-Ethoxy-1,3-dihydro-1-[2-methoxy-4-(1-methyl-2,4-dioxoimidazolin-3-yl) benzenesulfonyl]-3-spirocyclohexaneindol-2-one On heating at 100° C. for 24 hours under vacuum, the product obtained in the previous Example is cyclized to give 230 mg of the expected product.

M.p.=200° C.

EXAMPLE 290

1-[4-(N',N'-Diethylthioureido)-2-methoxybenzene sulfonyl]-5-ethoxy-1,3-dihydro-3-spirocyclohexaneindol-2-one A) 5-Ethoxy-1,3-dihydro-1-(2-methoxy-4-phenoxythiocarboxamidobenzenesulfonyl)-3-spirocyclohexaneindol-2-one A mixture containing 500 mg of the compound obtained in Example 283 step A), 900 mg of phenoxythiocarbonyl chloride, 30 ml of ether, 8 ml of water, 120 mg of sodium hydroxide and 20 ml of DCM is prepared. After stirring for 24 hours at RT, the solvents are evaporated off and the residue is then chromatographed on silica using DCM as the eluent. The expected product crystallizes from iso ether. m=140 mg. M.p.=157° C.

B) 1-[4-(N',N'-Diethylthioureido)-2-methoxybenzenesulfonyl]-5-ethoxy-1,3-dihydro-3-spirocyclohexaneindol-2-one A mixture containing 140 mg of the compound prepared in step A), 20 ml of 100° EtOH, 5 ml of DCM and 1 ml of diethylamine is stirred at RT for 18 hours. The solvents are evaporated off and the residue is then chromatographed on a silica column using pure DCM and then a DCM/AcOEt mixture (up to 90/10; v/v) as the eluent. The expected product crystallizes from ether. m=105 mg. M.p.=167° C.

EXAMPLE 291

5-Ethoxy-1,3-dihydro-1-(2-methoxy-4-guanidinobenzenesulfonyl)-3-spirocyclohexaneindol-2-one A mixture containing 500 mg of the compound prepared in Example 275 step B), 125 mg of cyanamide, 7 ml of AcOEt, 1 ml of EtOH and 0.2 ml of a 20% solution of hydrochloric acid in EtOH is refluxed for 1 hour. The solvents are evaporated off and the residue is then chromatographed on a silica column using DCM and then MeOH as the eluent. The product isolated solidifies in ether. A 2N solution of NaHCO₃ is added and the base formed is then extracted with AcOEt; the extract is evaporated to dryness and the expected product solidifies in iso ether. m=0.055 g. M.p.=235° C.

EXAMPLE 292

5-Ethoxy-1,3-dihydro-1-[2-methoxy-4-(N-methylcarbamoylmethoxy)benzenesulfonyl]-3-spirocyclohexaneindol-2-one A) Potassium 2-methoxy-4-(ethoxycarbonylmethoxy) Phenylsulfonate 10 g of ethyl (3-methoxyphenoxy)acetate and 30 ml of DCM are mixed at 0° C. and 7.5 ml of trimethylsilylsulfonyl chloride in 30 ml of DCM are added over 20 minutes. The temperature is allowed to rise to RT, with stirring, 30 g of ice are added after 2 hours and the mixture is stirred again. After decantation, the aqueous phase is washed with ether, and potassium carbonate is added in a sufficient amount to bring the pH to 7. The white precipitate which forms is filtered off and then washed with acetone and ether to give 3.1 g of the expected product, which is characterized by its NMR spectrum.

B) 2-Methoxy-4-(ethoxycarbonylmethoxy) phenylsulfonyl chloride 3.1 g of the compound obtained in the previous step in 30 ml of phosphorus oxychloride are refluxed for 3 hours. The medium is concentrated under vacuum and then taken up with ice. It is extracted with ethyl acetate, washed with water, with N sodium hydroxide and then with water again, dried over sodium sulfate and concentrated under vacuum. The expected product crystallizes from iso ether. m=2.5 g. M.p.=89° C.

C) Ethyl 3-methoxy-4-[(5-ethoxy-2,3-dihydro-2-oxo-3-spirocyclohexaneindol-1-yl)sulfonyl]phenoxyacetate A mixture containing 0.5 g of 5-ethoxy-1,3-dihydro-3-spirocyclohexaneindol-2-one, 5 ml of THF and 60 mg of sodium hydride is prepared. After stirring for 15 minutes at 15° C., 0.66 g of the compound prepared in the previous step is added. Stirring is maintained for 15 minutes and the medium is then concentrated under vacuum. It is extracted with ether and washed with water and the expected product is then crystallized from iso ether. m=0.85 g. M.p.=160° C.

D) 5-Ethoxy-1,3-dihydro-1-[2-methoxy-4-(N-methylcarbamoylmethoxy)benzenesulfonyl]-3-spirocyclohexaneindol-2-one A mixture containing 0.5 g of the compound prepared in the previous step, 15 ml of a 33% solution of methylamine in MeOH and 15 ml of EtOH is stirred for 4 days at RT. It is concentrated under vacuum and the residue is then chromatographed on silica. The column is washed with DCM and then eluted with AcOEt to give the expected product. m=0.1 g. M.p.=192°–195° C.

EXAMPLE 293

5-Ethoxy-1,3-dihydro-1-[2-methoxy-4-(N-methyl-N-(2-methylallyl)amino)benzenesulfonyl]-3-spirocyclohexaneindol-2-one A) 5-Ethoxy-1,3-dihydro-1-[2-methoxy-4-(N-methylamino)-benzenesulfonyl]-3-spirocyclohexaneindol-2-one 2 g of the compound prepared in Example 275 step B), cooled in an ice bath to 10° C., are dissolved in 6 ml of a 37% aqueous solution of formaldehyde and 40 ml of acetonitrile. 1.7 g of 85% pure sodium cyanoboro-hydride and then 0.5 ml of acetic acid are added and the mixture is stirred at RT for 24 hours. The acetonitrile is evaporated off and the residue is taken up with water and AcOEt. The organic phase is decanted, dried and then chromatographed twice in succession on silica using a DCM/heptane mixture (85/15; v/v), then pure DCM and finally a DCM/AcOEt mixture (98/2; v/v) as the eluent to give the expected compound. m=0.36 g. M.p.=157° C.

B) 5-Ethoxy-1,3-dihydro-1-[2-methoxy-4-(N-methyl-N-(2-methylallyl)amino)benzenesulfonyl]-3-spirocyclohexaneindol-2-one A mixture containing 500 mg of the compound obtained in the previous step, 10 ml of DMF, 0.5 ml of diethylamine and 0.5 ml of 3-chloro-2-methylpropene is refluxed for 10 hours. The reaction medium is poured into a water/ice mixture and then extracted with AcOEt, washed with water and chromatographed on silica using DCM as the eluent. The expected compound crystallizes from pentane. m=190 mg. M.p.=118° C.

The compounds (I) according to the invention described in Table 7 below were prepared by following the procedures described in the previous Examples.

TABLE 7

| Example | R₁ | CR₃R₄ | R₆ | M.p. °C. |
|---|---|---|---|---|
| 294 (a) | Cl— | cyclohexane | (2,5-dihydropyrrol-1-yl) N— | 179 |
| 295 (a) | EtO— | 4,4-dimethyl cyclohexane | (2,5-dihydropyrrol-1-yl) N— | 167 |
| 296 (b) | Cl— | cyclohexane | EtOCOCH₂NHCONH— | 167 |
| 297 (b) | Cl— | cyclohexane | cyclohexyl-N(Me)-CONH— | 139 |
| 298 (c) | EtO— | cyclohexane | cyclopentyl-N(Me)-CONH— | 150 |
| 299 (c) | EtO— | cyclohexane | Me—N(piperazine)N—CONH— | 197 |
| 300 (c) | EtO— | cyclohexane | MeON(Me)CONH— | 177 |
| 301 (c) | EtO— | cyclohexane | MeNH(CH₂)₂N(Me)CONH— | 170 hydrochloride monohydrate |
| 302 (c) | EtO— | cyclohexane | HON(Me)CONH— | 185 |
| 303 (c) | EtO— | cyclohexane | HOCH₂CH₂N(Me)CONH— | 128 |
| 304 (c) | EtO— | cyclohexane | (pyrrolidin-1-yl)N—CONH— | 139 |
| 305 (c) | EtO— | cyclohexane | (piperidin-1-yl)N—CONH— | 210 |
| 306 (c) | EtO— | cyclohexane | (morpholin-4-yl)O⟨⟩N—CONH— | 190 |

TABLE 7-continued

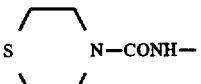

| Example | R₁ | CR₃R₄ | R₆ | M.p. °C. |
|---|---|---|---|---|
| 307 (c) | EtO— | cyclohexane | 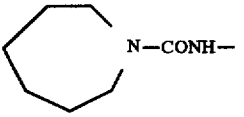 S⟨ ⟩N—CONH— | 212 |
| 308 (c) | EtO— | cyclohexane | 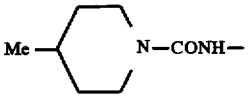 N—CONH— | 179 |
| 309 (c) | EtO— | cyclohexane | Me⟨ ⟩N—CONH— | 146 |
| 310 (c) | EtO— | cyclohexane | 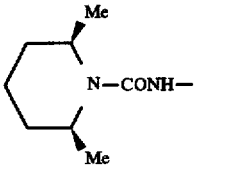 Me, Me N—CONH— | 198 |
| 311 (c) | EtO— | cyclohexane | MeN(CH₂)₂NCONH—<br>  |        |<br>  Me    Et | 208 hydrochloride monohydrate |
| 312 (c) | EtO— | cyclohexane | Ph⟨ ⟩N—CONH— | 195 |
| 313 (c) | EtO— | cyclohexane | MeN(CH₂)₂NCONH—<br>  |        |<br>  Me    Me | 200 fumarate |
| 314 (c) | EtO— | cyclohexane | 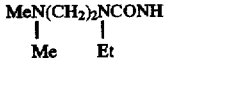 (CH₂)₂NCONH<br>           |<br>          Me | 159 |
| 315 (d) | Cl— | 4,4-dimethyl-cyclohexane | S<br>||<br>Et₂NCNH— | 179 |
| 316 (d) | EtO— | 4,4-dimethyl-cyclohexane | S<br>||<br>Et₂NCNH— | 146 |
| 317 | EtO— | cyclohexane | 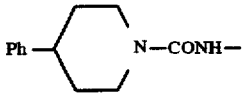 —CH₂NHCO— CF₃ | 173 |

TABLE 7-continued

[Structure: indolin-2-one with R1 at 5-position, R3 and R4 at 3-position, N-SO2-(2-methoxy-4-R6-phenyl)]

| Example | R₁ | CR₃R₄ | R₆ | M.p. °C. |
|---|---|---|---|---|
| 318 (e) | EtO— | cyclohexane | (tetrahydrofuran-2-yl)CH₂NHCO— | 189 |
| 319 (e) | EtO— | cyclohexane | CF₃CH₂NHCO— | 210 |
| 320 (e) | EtO— | cyclohexane | cyclopentyl-NHCO— | 196 |
| 321 (e) | EtO— | cyclohexane | cyclohexyl-NHCO— | 155 |
| 322 (e) | EtO— | cyclohexane | (piperidin-4-yl)N—NHCO— | 204 |
| 323 (e) | EtO— | cyclohexane | adamantyl-CH₂NHCO— | 143 |
| 324 (e) | EtO— | cyclohexane | EtO(CH₂)₂NHCO— | 166 |
| 325 (e) | EtO— | cyclohexane | H₂NCOCH₂NHCO— | 245 |
| 326 (e) | EtO— | cyclohexane | Et₂N—COCH₂NHCO— | 161 |
| 327 (e) | EtO— | cyclohexane | (Et₂N—COCH₂)₂NCO— | 141 |
| 328 (e) | EtO— | cyclohexane | NC—C(Me)₂NHCO— | 198 |
| 329 (f) | EtO— | cyclohexane | Et₂NC(NH)NH— | 137 hydrochloride hemihydrate |
| 330 (g) | Cl— | C[(CH₂)₂O-(tetrahydropyran-2-yl)]₂ | CH₃O— | 136 |
| 331 (1)(b) | EtO— | cyclohexane with OCH₂OCH₃ | Et₂NCONH— | 88 |
| 332 (1)(h) | EtO— | cyclohexane with OH | Et₂NCONH— | 130 |

(a) This compound is prepared by the procedure described in EXAMPLE 276 step C), the reaction being carried out under an inert atmosphere using triethylamine as the base.

(b) This compound is prepared by the procedures described in EXAMPLE 283 step A) and then step B) using the appropriate amino derivatives or nitrogen heterocycles.

(c) This compound is prepared by the procedure described in EXAMPLE 283 step B) using the appropriate amino derivatives or nitrogen heterocycles.

(d) This compound is prepared by the procedures described in EXAMPLE 290 step A) and then step B).

(e) This compound is prepared by the procedure described in EXAMPLE 280 step D) using the appropriate amines.

(f) This compound is prepared by the procedure described in EXAMPLE 291 using N,N-diethylcyanamide.

(g) This compound is prepared by the procedure described in EXAMPLE 275 step A) using 2,4-dimethoxybenzenesulfonyl chloride and the appropriate indol-2-one.

(h) This compound is prepared by the procedure described in EXAMPLE 342 starting from the compound obtained in EXAMPLE 331 (mixture of isomers).

(l) mixture of isomers

EXAMPLE 333

5-Ethoxy-1-[4-(N',N'-diethylureido)-2-methoxybenzenesulfonyl]-1,3-dihydro-3-spiro(4-oxocyclohexane)-indol-2-one 0.25 hydrate A mixture of 0.3 g of the compound obtained in EXAMPLE 342, 0.3 g of pyridinium chlorochromate and 1.5 ml of DCM is stirred for 16 hours at RT. 10 ml of water are added to the reaction mixture, the DCM is evaporated off under vacuum, the residue is extracted with AcOEt and dried over magnesium sulfate and the solvent is concentrated under vacuum. The residue is chromatographed on silica using a DCM/MeOH mixture (98/2; v/v) as the eluent to give 0.26 g of the expected product. M.p.=100° C.

EXAMPLE 334

5-Fluoro-1,3-dihydro-1-[2-methoxy-4-(Δ3-Pyrrolin-1-yl)benzenesulfonyl]-3-spiro(4,4-dimethylcyclohexane)indol-2-one This compound is prepared by the procedure described in EXAMPLE 2 step C), the reaction being carried out under an inert atmosphere using triethylamine as the base.

EXAMPLE 335

5-Chloro-3,3-dihydroxyethyl-1,3-dihydro-1-(2,4-dimethoxybenzenesulfonyl)indol-2-one This compound is prepared by the method described in J. Org. Chem., 1977, 42, 3772. 0.037 g of pyridinium toluenesulfonate in 12 ml of ethanol is added to 0.92 g of the compound of Example 330 described in Table 7 above, and the mixture is heated at about 55° C. for 3 hours. The solvent is evaporated off under reduced pressure and the residue is chromatographed on a silica column using DCM as the eluent. The expected product is isolated and crystallized from a hot cyclohexane/ethyl acetate mixture (50/50; v/v). M.p.=166° C.

EXAMPLES 336 AND 337

5-Ethoxy-1,3-dihydro-1-(2-methoxy-4-nitrobenzenesulfonyl)-3-spiro[4-(methoxymethoxy)cyclohexane]-indol-2-one, the less polar isomer and the more polar isomer These compounds are prepared by the procedure described in EXAMPLE 275 step A') starting from 5-ethoxy-1,3-dihydro-3-spiro[4-(methoxymethoxy)-cyclohexane]-indol-2-one. They are chromatographed on silica using a cyclohexane/AcOEt mixture (95/5; v/v) as the eluent. The two isomers are separated into the less polar isomer: compound of EXAMPLE 336, m.p.=127° C.;

the more polar isomer: compound of EXAMPLE 337, m.p.=118° C.

EXAMPLES 338 AND 339

1-(4-Amino-2-methoxybenzenesulfonyl)-5-ethoxy-1,3-dihydro-3-spiro[4-(methoxymethoxy)cyclohexane]-indol-2-one, the less polar isomer and the more polar isomer These compounds are prepared by the procedure described in EXAMPLE 275 step B") starting from the mixture of compounds obtained in EXAMPLES 336 and 337 before chromatography. They are chromatographed on silica using a cyclohexane/AcOEt mixture (95/5; v/v) as the eluent. The two isomers are separated into the less polar isomer: compound of EXAMPLE 338, m.p.=103° C.;

the more polar isomer: compound of EXAMPLE 339, m.p.=111° C.

EXAMPLE 340

5-Ethoxy-1-[4-(N',N'-diethylureido)-2-methoxybenzenesulfonyl]-1,3-dihydro-3-spiro[4-(methoxy-methoxy)-cyclohexane]indol-2-one, the less polar isomer This compound is prepared by the procedure described in EXAMPLE 283 step A) and then step B) starting from the compound obtained in EXAMPLE 338 and using diethylamine in the 2nd step. The expected product is obtained after recrystallization from a cyclohexane/AcOEt mixture. M.p.=160° C.

EXAMPLE 341

5-Ethoxy-1-[4-(N',N'-diethylureido)-2-methoxybenzenesulfonyl]-1,3-dihydro-3-spiro[4-(methoxymethoxy)cyclohexane]indol-2-one, the more polar isomer This compound is prepared by the procedure described in EXAMPLE 283 step A) and then step B) starting from the compound obtained in EXAMPLE 339 and using diethylamine in the 2nd step. The expected product is obtained after recrystallization from a cyclohexane/AcOEt mixture. M.p.=137° C.

EXAMPLE 342

5-Ethoxy-1-[4-(N',N'-diethylureido)-2-methoxybenzenesulfonyl]-1,3-dihydro-3-spiro(4-hydroxycyclohexane)indol-2-one monohydrate, the less polar isomer A solution of 2.2 g of the compound obtained in EXAMPLE 340 in 6 ml of MeOH and 1.2 ml of concentrated HCl is heated at 50° C. for 30 minutes. 10 ml of water are added to the reaction mixture, extraction is carried out with AcOEt, the extract is dried over magnesium sulfate and the solvent is evaporated off under vacuum. The residue is chromatographed on silica using a DCM/MeOH mixture

EXAMPLE 343

5-Ethoxy-1-[4-(N',N'-diethylureido)-2-methoxybenzenesulfonyl]-1,3-dihydro-3-spiro(4-hydroxycyclohexane)indol-2-one monohydrate, the more polar isomer This compound is prepared by the procedure described in EXAMPLE 342 starting from the compound obtained in EXAMPLE 341. The expected product is obtained after recrystallization from a cyclohexane/AcOEt mixture. M.p.=144° C.

EXAMPLE 344

5-Ethoxy-1,3-dihydro-1-(2-methoxy-4-nitrobenzenesulfonyl)-3-spiro(4-methoxycyclohexane)indol-2-one, the more polar isomer This compound is prepared by the procedure described in EXAMPLE 275 step A') starting from the more polar isomer of 5-ethoxy-1,3-dihydro-3-spiro(4-methoxy-cyclohexane)indol-2-one (compound of Preparation 17). The expected product is obtained.

M.p.=141° C.

EXAMPLE 345

1-(4-Amino-2-methoxybenzenesulfonyl)-5-ethoxy-1,3-dihydro-3-spiro(4-methoxycyclohexane)indol-2-one, the more polar isomer This compound is prepared by the procedure described in EXAMPLE 275 step B") starting from the compound obtained in EXAMPLE 344. M.p.=199° C.

EXAMPLE 346

5-Ethoxy-1-[4-(N',N'-diethylureido)-2-methoxybenzenesulfonyl]-1,3-dihydro-3-spiro(4-methoxycyclohexane)indol-2-one, the less polar isomer A) 5-Ethoxy-1,3-dihydro-1-(2-methoxy-4-nitrobenzenesulfonyl)-3-spiro(4-methoxycyclohexane)indol-2-one, the less polar isomer This compound is prepared by the procedure described in EXAMPLE 275 step A') starting from the compound obtained in Preparation 16 (the less polar isomer).

B) 1-(4-Amino-2-methoxybenzenesulfonyl)-5-ethoxy-1,3-dihydro-3-spiro(4-methoxycyclohexane)indol-2-one, the less polar isomer This compound is prepared by the procedure described in EXAMPLE 275 step B") starting from the compound obtained in the previous step.

C) 5-Ethoxy-1-[4-(N',N'-diethylureido)-2-methoxybenzenesulfonyl]-1,3-dihydro-3-spiro(4-methoxycyclohexane)indol-2-one, the less polar isomer This compound is prepared by the procedure described in EXAMPLE 283 step A) and then step B) starting from the compound obtained in the previous step and using diethylamine. M.p.=118° C.

EXAMPLE 347

5-Ethoxy-1-[4-(N',N'-diethylureido)-2-methoxybenzenesulfonyl]-1,3-dihydro-3-spiro(4-methoxycyclohexane)indol-2-one, the more polar isomer This compound is prepared by the procedure described in EXAMPLE 283 step A) and then step B) starting from the compound obtained in EXAMPLE 345 and using diethylamine in the 2nd step. The expected product is obtained after recrystallization from a cyclohexane/AcOEt mixture. M.p.=164° C.

EXAMPLE 348

5-Ethoxy-1,3-dihydro-1-(2-methoxy-4-nitrobenzenesulfonyl)-3-spiro(4-hydroxycyclohexane)indol-2-one, the more polar isomer A mixture of 2.2 g of the compound obtained in EXAMPLE 337 and 1.2 ml of concentrated HCl in 6 ml of MeOH is heated at 50° C. for 1 hour. 10 ml of water are added to the reaction mixture and the precipitate formed is filtered off, washed with water and dried under vacuum at 50° C. to give 1.3 g of the expected product. M.p.=135° C.

EXAMPLE 349

5-Ethoxy-1-[4-(N',N'-diethylureido)-2-methoxybenzenesulfonyl]-1,3-dihydro-3-spiro(4-ethoxycyclohexane)indol-2-one A) 5-Ethoxy-1,3-dihydro-1-(2-methoxy-4-nitrobenzene sulfonyl)-3-spiro(4-ethoxycyclohexane)indol-2-one A solution of 0.25 g of 5-ethoxy-1,3-dihydro-1-(2-methoxy-4-nitrobenzenesulfonyl)-3-spiro(4-hydroxycyclohexane)indol-2-one (prepared by the procedure described in EXAMPLE 348 starting from the mixture of isomers obtained in EXAMPLES 336 and 337 before chromatography), 0.6 ml of 2,6-di-tert-butylpyridine and 0.37 ml of ethyl trifluoromethanesulfonate in DCM is stirred for 6 hours at 40° C. 5 ml of 5N HCl are added to the reaction mixture, extraction is carried out with AcOEt, the organic phase is washed three times with 0.5N HCl and with a saturated solution of NaCl and dried over magnesium sulfate and the solvent is evaporated off under vacuum to give 0.5 g of the expected product in the form of an oil, which is used as such in the next step.

B) 1-(4-Amino-2-methoxybenzenesulfonyl)-5-ethoxy-1,3-dihydro-3-spiro(4-ethoxycyclohexane)indol-2-one This compound is prepared by the procedure described in EXAMPLE 275 step B') by chemical reduction of the compound obtained in the previous step. It is chromatographed on silica using a DCM/MeOH mixture (99/1; v/v) as the eluent to give the expected product.

M.p.=110° C.

C) 5-Ethoxy-1,3-dihydro-1-(2-methoxy-4-phenoxycarboxamidobenzenesulfonyl)-3-spiro(4-ethoxycyclohexane)-indol-2-one This compound is prepared by the procedure described in EXAMPLE 283 step A) starting from the compound obtained in the previous step. This gives the expected product, which is used as such in the next step.

D) 5-Ethoxy-1-[4-(N',N'-diethylureido)-2-methoxybenzenesulfonyl]-1,3-dihydro-3-spiro(4-ethoxycyclohexane)indol-2-one This compound is prepared by the procedure described in EXAMPLE 283 seep B) starting from the compound obtained in the previous step and diethylamine. The expected product is obtained.

M.p.=121° C.

EXAMPLE 350

5-Ethoxy-1-[4-(N',N'-diethylureido)-2-methoxybenzenesulfonyl]-1,3-dihydro-3-spiro[4-(2-methoxyethoxy)cyclohexane]indol-2-one A) 5-Ethoxy-1,3-dihydro-1-(2-methoxy-4-nitrobenzenesulfonyl)-3-spiro[4-(2-methoxyethoxy)cyclohexane]-indol-2-one A mixture of 0.2 g of 5-ethoxy-1,3-dihydro-1-(2-methoxy-4-nitrobenzenesulfonyl)-3-spiro(4-hydroxycyclohexane)indol-2-one, 2 g of 1-iodo-2-methoxyethane, 0.9 ml of 2,6-di-tert-butylpyridine and 2.15 g of silver trifluoromethanesulfonate in 17 ml of $CCl_4$ and 8 ml of DCM is stirred for 24 hours at RT. 100 ml of 0.1N HCl are added to the reaction mixture, the solvents are evaporated off under vacuum, the residue is extracted with AcOEt and dried over magnesium sulfate and the solvent is evaporated off under vacuum. The residue is chromatographed on silica using cyclohexane as the eluent to give 0.36 g of the expected product, which is used as such in the next step.

B) 1-(4-Amino-2-methoxybenzenesulfonyl)-5-ethoxy-1,3-dihydro-3-spiro[4-(2-methoxyethoxy)cyclohexane]indol-2-one This compound is prepared by the procedure described in EXAMPLE 275 step B') by reduction of the compound obtained in the previous step. The expected product is obtained. M.p=118° C.

C) 5-Ethoxy-1,3-dihydro-1-(2-methoxy-4-phenoxycarboxamidobenzenesulfonyl)-3-spiro[4-(2-methoxyethoxy)-cyclohexane]indol-2-one This compound is prepared by the procedure described in EXAMPLE 283 step A) starting from the compound obtained in the previous step. This gives the expected product, which is used as such in the next step.

D) 5-Ethoxy-1-[4-(N',N'-diethylureido)-2-methoxybenzenesulfonyl]-1,3-dihydro-3-spiro[4-(1-methoxyethoxy)cyclohexane]indol-2-one This compound is prepared by the procedure described in EXAMPLE 9 step B) starting from the compound obtained in the previous step and diethylamine. The expected product is obtained.

M.p.=98° C.

EXAMPLE 351

5-Ethoxy-1-[4-(N',N'-diethylureido)-2-methoxybenzenesulfonyl]-1,3-dihydro-3-spiro(4-n-propoxycyclohexane)indol-2-one This compound is prepared by the procedures described in EXAMPLE 349 step A) starting from 5-ethoxy-1,3-dihydro-1-(2-methoxy-4-nitrobenzenesulfonyl)-3-spiro(4-hydroxycyclohexane)indol-2-one and 1-iodopropane in benzene, and then steps B), C) and D). The expected product is obtained. M.p.=115° C.

EXAMPLE 352

5-Ethoxy-1-[4-(N',N'-diethylureido)-2-methoxybenzenesulfonyl]-1,3-dihydro-3-spiro(4-isopropoxycyclohexane)indol-2-one hemihydrate This compound is prepared by the procedures described in EXAMPLE 350 step A) starting from 5-ethoxy-1,3-dihydro-1-(2-methoxy-4-nitrobenzenesulfonyl)-3-spiro(4-hydroxycyclohexane)indol-2-one and 2-iodopropane in benzene, and then steps B), C) and D). The expected product is obtained. M.p=130° C.

EXAMPLE 353

5-Ethoxy-1-[4-(N',N'-diethylureido)-2-methoxybenzenesulfonyl]-1,3-dihydro-3-spiro[4-(2-tert-butoxyethoxy)cyclohexane]indol-2-one This compound is prepared by the procedures described in EXAMPLE 350 step A) starting from 5-ethoxy-1,3-dihydro-1-(2-methoxy-4-nitrobenzenesulfonyl)-3-spiro(4-hydroxycyclohexane)indol-2-one and 1-iodo-2-tert-butoxyethane, and then steps B), C) and D). The expected product is obtained. M.p.=103° C.

EXAMPLE 354

5-Ethoxy-1-[4-(N',N'-diethylureido)-2-methoxybenzenesulfonyl]-1,3-dihydro-3-spiro[4-(2-hydroxyethoxy)cyclohexane]indol-2-one A mixture of 0.35 g of the compound obtained in EXAMPLE 353 and 4 ml of trifluoroacetic acid in 15 ml of DCM is stirred for 2 hours at RT. 40 ml of a saturated solution of $NaHCO_3$ are added, the mixture is decanted, the organic phase is washed with water and dried over magnesium sulfate and the solvent is evaporated off under vacuum. The residue is chromatographed on silica using a DCM/MeOH mixture (90/10; v/v) as the eluent to give the expected product. M.p.=109° C.

EXAMPLE 355

5-Ethoxy-1-[4-(N',N'-diethylureido)-2-methoxybenzenesulfonyl]-1,3-dihydro-3-spiro(4-formyloxycyclohexane)indol-2-one, the more polar isomer A mixture of 0.25 g of the compound obtained in EXAMPLE 343, 0.18 g of cesium carbonate, 0.45 ml of dimethyl sulfate and 12 ml of DMF is heated at 40° C. for 12 hours. 10 ml of water are added, the reaction mixture is extracted with AcOEt, the organic phase is washed with water and dried over magnesium sulfate and the solvent is evaporated off under vacuum. The residue is chromatographed on silica using DCM as the eluent to give 0.2 g of the expected product after recrystallization from a cyclohexane/AcOEt mixture.

M.p.=155° C.

EXAMPLE 356

5-Ethoxy-1-[4-(N',N'-diethylureido)-2-methoxybenzenesulfonyl]-1,3-dihydro-3-spiro(4-acetoxycyclohexane)indol-2-one, the more polar isomer A mixture of 3 g of the compound obtained in EXAMPLE 343, 0.75 g of 4-dimethylaminopyridine, 3 ml of acetic anhydride and 5 ml of DCM is heated at 40° C. for 5 hours. Water is added to the reaction mixture, ex traction is carried out with DCM, the extract is washed with water and dried over magnesium sulfate and the solvent is evaporated off under vacuum. The residue is chromatographed on silica using a DCM/cyclohexane mixture as the eluent to give the expected product after recrystallization from iso ether. M.p.=140° C.

EXAMPLE 357

5-Ethoxy-1,3-dihydro-1-(2,4-dimethoxybenzenesulfonyl)-3-spiro(8,9-dihydroxytricyclo[5.2.1.0$^{2,6}$]-decan-4-yl)indol-2-one A) 5-Ethoxy-1,3-dihydro-1-(2,4-dimethoxybenzenesulfonyl)-3-spiro(8,9-epoxytricyclo[5.2.1.0$^{2,6}$]decan-4-yl)indol-2-one A mixture of 0.3 g of 5-ethoxy-1,3-dihydro-1-(2,4-dimethoxybenzenesulfonyl)-3-spiro(tricyclo-[5.2.1.0$^{2,6}$]dec-8-en-4-yl)indol-2-one and 0.2 g of metachloroperbenzoic acid in 20 ml of DCM is stirred for 3 hours at RT. 15 ml of a saturated solution of NaHCO$_3$ are added, the mixture is decanted, extraction is carried out with DCM, the extract is dried over magnesium sulfate and the solvent is evaporated off under vacuum. The residue is chromatographed on silica using DCM as the eluent to give 0.25 g of the expected product after recrystallization from an acetone/DCM mixture. M.p.=263° C.

B) 5-Ethoxy-1,3-dihydro-1-(2,4-dimethoxybenzenesulfonyl)-3-spiro(8,9-dihydroxytricyclo[5.2.1.0$^{2,6}$]decan-4-yl)indol-2-one A mixture of 0.2 g of the compound obtained in the previous step, 20 ml of water, 2 ml of concentrated sulfuric acid and 20 ml of THF is refluxed for 8 hours. The reaction mixture is neutralized by the addition of a saturated solution of NaHCO$_3$, the solvent is evaporated off under vacuum, the residue is extracted with DCM and dried over magnesium sulfate and the solvent is evaporated off under vacuum. The residue is chromatographed on silica using a DCM/MeOH mixture (99/1; v/v) as the eluent to give 0.17 g of the expected product. M.p.=150° C.

What is claimed is:

1. A compound of the formula:

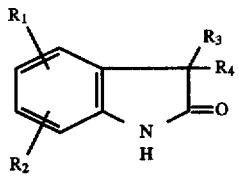

(II)' in which

R$_1$ and R$_2$ are each independently a hydrogen, a hydroxy, a C$_1$–C$_4$-ω-halogenoalkoxy, a halogen, a C$_1$–C$_4$-alkyl, a trifluoromethyl, a C$_1$–C$_7$-alkoxy, a C$_1$–C$_4$-polyhalogenoalkoxy, a C$_2$–C$_4$-ω-hydroxyalkoxy, an ω-methoxyalkoxy in which the alkyl is C$_2$–C$_4$, a C$_2$–C$_4$-ω-aminoalkoxy which is free or substituted by one or two C$_1$–C$_4$-alkyls, a C$_3$–C$_7$-cycloalkoxy, a cycloalkylmethoxy in which the cycloalkyl is C$_3$–C$_7$, a phenoxy, a benzyloxy, a C$_1$–C$_4$-alkylthio, a phenylthio, a nitro, an amino which is free or substituted by one or two C$_1$–C$_4$-alkyls, a cyano, a C$_1$–C$_4$-acyl, a C$_1$–C$_4$-acyloxy, a C$_1$–C$_4$-alkylsulfonamido, a phenylsulfonamido, a C$_1$–C$_4$-alkylamido, a C$_1$–C$_4$-alkoxycarbonylamino or a ureido which is unsubstituted or substituted by a phenol or by one or two C$_1$–C$_4$-alkyls; and R$_3$ and R$_4$ together form a group —(CH$_2$)$_p$X(CH$_2$)$_q$— in which p and q are integers whose sum can vary from 3 to 6 and X is oxygen or sulfur.

2. A compound of formula (II)":

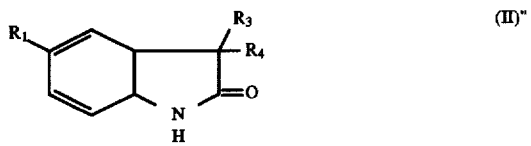

(II)"

in which:

R$_1$ is a hydroxy, a C$_1$–C$_4$-ω-halogenoalkoxy, a halogen, a C$_1$–C$_4$-alkyl, a trifluoromethyl, a C$_1$–C$_7$-alkoxy, a C$_1$–C$_4$-polyhalogenoalkoxy, a C$_2$–C$_4$-ω-hydroxyalkoxy, an ω-methoxyalkoxy in which the alkyl is C$_2$–C$_4$, a C$_2$–C$_4$-ω-aminoalkoxy which is free or substituted by one or two C$_1$–C$_4$ alkyls, a C$_3$–C$_7$-cycloalkoxy, a cycloalkylmethoxy in which the cycloalkyl is C$_3$–C$_7$; a phenoxy; a benzyloxy; a C$_1$–C$_4$-alkylthio; a phenylthio; a nitro; an amino which is free or substituted by one or two C$_1$–C$_4$-alkyls; a cyano; a C$_1$–C$_4$-acyl; a C$_1$–C$_4$-acyloxy; a C$_1$–C$_4$-alkylsulfonamido; a phenylsulfonamido; a C$_1$–C$_4$-alkylamido; a C$_1$–C$_4$-alkoxycarbonylamino; or a ureido which is unsubstituted or substituted by a phenyl or by one or two C$_1$–C$_4$-alkyls;

R$_3$ and R$_4$ together form a group —(CH$_2$)$_p$X(CH$_2$)$_q$;

p and q are each an integer, it being possible for their sum to vary from 3 to 6; and X is oxygen or sulfur.

3. A compound according to claim 2 in which R$_1$ is ethoxy.

* * * * *